United States Patent [19]

Kuo et al.

[11] Patent Number: 5,045,455
[45] Date of Patent: Sep. 3, 1991

[54] FACTOR VIII:C CDNA CLONING AND EXPRESSION

[75] Inventors: George Kuo; Frank Masiarz, both of San Francisco; Martha Truett, Oakland; Pablo Valenzuela, San Francisco, all of Calif.; Mirella E. Rasmussen, Copenhagen, Denmark; Jennifer M. Favaloro, Victoria, Australia; Daniel Caput; Rae L. Burke, both of San Francisco, Calif.; Carol Pachl, Oakland, Calif.

[73] Assignee: Chiron Corporation, Emeryville, Calif.

[21] Appl. No.: 538,691

[22] Filed: Jun. 14, 1990

Related U.S. Application Data

[63] Continuation of Ser. No. 757,095, Jul. 19, 1985, abandoned, which is a continuation-in-part of Ser. No. 689,274, Jan. 7, 1985, Pat. No. 4,716,117, which is a continuation-in-part of Ser. No. 664,919, Oct. 26, 1984, abandoned, which is a continuation-in-part of Ser. No. 570,062, Jan. 12, 1984, Pat. No. 5,004,804.

[51] Int. Cl.$^5$ ............... C12N 15/03; C12N 15/06; C12N 1/21; C12N 5/10; C12N 15/12; C12P 21/02; C07H 15/12

[52] U.S. Cl. ............... 435/69.6; 435/69.1; 435/172.3; 435/252.3; 435/252.33; 435/240.2; 435/320.1; 435/91; 536/27; 935/11; 935/27; 935/29; 935/56; 935/60; 935/70; 935/73; 935/32

[58] Field of Search ............ 435/69.1, 69.6, 70.1, 435/70.3, 172.3, 252.3, 252.33, 240.2, 320, 91, 320.1; 536/27

[56] References Cited

U.S. PATENT DOCUMENTS

| | | | |
|---|---|---|---|
| 4,361,509 | 11/1982 | Zimmerman et al. | 260/112 B |
| 4,419,446 | 12/1983 | Howley et al. | 435/68 |
| 4,649,132 | 3/1987 | Zimmerman et al. | 514/12 |
| 4,657,894 | 4/1987 | Zimmerman et al. | 514/21 |
| 4,757,006 | 7/1988 | Toole, Jr. et al. | 435/70 |

FOREIGN PATENT DOCUMENTS

| | | |
|---|---|---|
| 53519 | 3/1984 | Denmark. |
| 083483 | 7/1983 | European Pat. Off. |
| 123945 | 11/1984 | European Pat. Off. |
| 157556 | 10/1985 | European Pat. Off. |
| 160457 | 11/1985 | European Pat. Off. |
| 182372 | 5/1986 | European Pat. Off. |
| 8404541 | 11/1984 | PCT Int'l Appl. |
| 8501961 | 5/1985 | PCT Int'l Appl. |

OTHER PUBLICATIONS

Bock et al, Nucleic Acids Research, vol. 10, pp. 8113–8125 (1982).

Jaye et al, Nucleic Acid Research, vol. 11, pp. 2325–2335, Apr. 25, 1983.

Ginsburg et al., (1985) Science 228:1401–1406.

Kurachi et al., (1982) Proc. Natl. Acad. Sci. U.S.A. 79:6461–6464.

(List continued on next page.)

Primary Examiner—Elizabeth C. Weimar
Assistant Examiner—Christopher S. F. Low
Attorney, Agent, or Firm—Robert P. Blackburn; Grant D. Green

[57] ABSTRACT

Methods and compositions are provided for recombinant DNA production of Factor VIIIC and truncated derivatives thereof. Based on amino acid sequences, probes are developed for isolating messenger RNA, cDNA and/or chromosomal DNA encoding for Factor VIIIC. The Factor VIIIC gene in its entirety, a fragment thereof, or a cDNA is then used for expression of Factor VIIIC in a host.

The bacteriophage λFVIII23D containing the 14.43kb EcoRI fragment was deposited at the A.T.C.C. on Jan. 4, 1984 and given Accession No. 40094. Also, the vector pSVF8-200 was deposited at the A.T.C.C. on July 17, 1985 and given Accession No. 40190.

16 Claims, 11 Drawing Sheets

OTHER PUBLICATIONS

Maniatis et al., *Molecular Cloning: A Laboratory Manual*, pp. 224–228 (1982).
Bloom (1983) Nature 303:474–475.
Muller et al., (1981) Blood 58:1000–1006.
Muller et al., (1982) Chemical Abstracts vol. 96, No. 5, p. 480 (Abstract No. 33095v).
Maddox (1983) Nature 306:528.
Rotblat et al., (1984) Biological Abstracts 77:4443 (Abstract No. 40713).
Rotblat et al., (1983) J. Lab. Clin. & Med. 101:736–746.
Hybritech Data Sheet (Catalogue #0432) (1982).
Fulcher et al., (1983) Blood 61:807–809.
Fulcher et al., (1983) Chemical Abstracts vol. 98, No. 21, p. 450 (Abstract No. 176896j).
Fass et al., (1982) Blood 59:594–600.
Kaufman et al., (1982) Molecular and Cellular Biology 2:1304–1319.
Fay et al., (1982) Proc. Natl. Acad. Sci. 79:7200–7204.
Choo et al., (1982) Nature 299:178–180.
Chan et al., (1984) Chemical Abstracts vol. 100, p. 214 (Abstract No. 63605e).
Rotblat et al., (1985) Biochemistry 24: 4294–4300.
Fulcher et al. (1982) Proc. Natl. Acad. Sci. U.S.A. 79:1648–1652.
Tuddenham et al. (1979) J. of Lab. Clin. Med. 93:40–53.
Austen (1979) British J. Menatology 43:669–674.
Weinstein et al. (1981) Proc. Natl. Acad. Sci. U.S.A. 78:5137–5141.
Kuo et al., Abstracts for IX Int. Cong. Thrombosis & Hemostasis, (Copenhagen, Jul. 1983).
Gitschier et al. (1984) Nature 312:326–330.
Wood et al. (1984) Nature 312:330–337.
Vehar et al. (1984) Nature 312:337–342.
Toole et al. (1984) Nature 312:342–347.

FIG.1A

```
-----------|----|---------------|-----|---|---|----|----|------------
          sacI                ecorI    hindIII   ecorI
                                  afl11    nde1    stu1
                                     bcl1         spe1
                                                  bal1

----|------|----|----|----------------|----|----------------|----|----
  sspI   bstXI                      sspI                  sspI  bglII
        hind111                            xmn1
        pvu11

---|----|---------------|----|---|----|----|--------|-|--|-|-
  kpn1                bstXI   hindIII    tthIII1-1    stu1
   pvu11                        ecor1              bstXI
    bamh1                                          tthIII1-2
                                                    pst1

----|----------|----|---|----|---|--------|----------
   mstII      aha111   bstXI  ndeI       mstII
              sac1       aha111  apa1
                          bsm1

----|---------|---|----|----------|---------|---|---|----|-
   xmn1      ava3                bglII      bcII    xmnI
    nde1      sph1                                    bal1
    nde1      ecor5
    sca1      xmn1

------|-------------------------|---------|---|-
     bstXI                     pstI      stu1  ndeI
      bamh1

|----------|---|---------------|---|--|---|--------------|----
           pstI               bsmI  xmn1              sspI
stu1       aha111              bgl1  apa1
                                      bal1

-|---------|---|-----|---|---|-----|----|---|----|--|---|----|--
 aha111  mstII  xmn1  xbaI  balI           pstI   stu1  aha11
  sph1    bstXI  bal1  ecor1              pvu11       hpa1
                      mstII                  xmn1      bcl1
                       pst1

------------------------|----|----|----------|---------|-------|-
                       hindIII              bamhI      bamh1
                        bal1
                        ssp1
                         nco1

-----|--------|----
    tthIII1=2
     hpa1
```

```
  1 GCTTAGTGCTGAGCACATCCAGTGGGTAAAGTTCCTTAAAATGCTCTGCAAAGAAATTGG      F8-102
    CGAATCACGACTCGTGTAGGTCACCCATTTCAAGGAATTTTACGAGACGTTTCTTTAACC

61 GACTTTTCATTAAATCAGAAATTTTACTTTTTTCCCCTCCTGGGAGCTAAAGATATTTTA
    CTGAAAAGTAATTTAGTCTTTAAAATGAAAAAAGGGGAGGACCCTCGATTTCTATAAAAT

MetGlnIle
121 GAGAAGAATTAACCTTTTGCTTCTCCAGTTGAACATTTGTAGCAATAAGTCATGCAAATA
    CTCTTCTTAATTGGAAAACGAAGAGGTCAACTTGTAAACATCGTTATTCAGTACGTTTAT

GluLeuSerThrCysPhePheLeuCysLeuLeuArgPheCysPheSerAlaThrArgArg
181 GAGCTCTCCACCTGCTTCTTTCTGTGCCTTTTGCGATTCTGCTTTAGTGCCACCAGAAGA
    CTCGAGAGGTGGACGAAGAAAGACACGGAAAACGCTAAGACGAAATCACGGTGGTCTTCT 181 sac1,
```

FIG.1B

```
         TyrTyrLeuGlyAlaValGluLeuSerTrpAspTyrMetGlnSerAspLeuGlyGluLeu
241      TACTACCTGGGTGCAGTGGAACTGTCATGGGACTATATGCAAAGTGATCTCGGTGAGCTG
         ATGATGGACCCACGTCACCTTGACAGTACCCTGATATACGTTTCACTAGAGCCACTCGAC

ProValAspAlaArgPheProProArgValProLysSerPheProPheAsnThrSerVal
301      CCTGTGGACGCAAGATTTCCTCCTAGAGTGCCAAAATCTTTTCCATTCAACACCTCAGTC
         GGACACCTGCGTTCTAAAGGAGGATCTCACGGTTTTAGAAAAGGTAAGTTGTGGAGTCAG

ValTyrLysLysThrLeuPheValGluPheThrAspHisLeuPheAsnIleAlaLysPro
361      GTGTACAAAAAGACTCTGTTTGTAGAATTCACGGATCACCTTTTCAACATCGCTAAGCCA
         CACATGTTTTTCTGAGACAAACATCTTAAGTGCCTAGTGGAAAAGTTGTAGCGATTCGGT 385 ecor1, ArgProProTrpMetGlyLeuLeuGlyProThrIleGlnAlaGluValTyrAspThrVal
421      AGGCCACCCTGGATGGGTCTGCTAGGTCCTACCATCCAGGCTGAGGTTTATGATACAGTG
         TCCGGTGGGACCTACCCAGACGATCCAGGATGGTAGGTCCGACTCCAAATACTATGTCAC ValIleThrLeuLysAsnMetAlaSerHisProValSerLeuHisAlaValGlyValSer
481      GTCATTACACTTAAGAACATGGCTTCCCATCCTGTCAGTCTTCATGCTGTTGGTGTATCC
         CAGTAATGTGAATTCTTGTACCGAAGGGTAGGACAGTCAGAAGTACGACAACCACATAGG 490 afl11, TyrTrpLysAlaSerGluGlyAlaGluTyrAspAspGlnThrSerGlnArgGluLysGlu
541      TACTGGAAAGCTTCTGAGGGAGCTGAATATGATGATCAGACCAGTCAAAGGGAGAAAGAA
         ATGACCTTTCGAAGACTCCCTCGACTTATACTACTAGTCTGGTCAGTTTCCCTCTTTCTT 548 hind111, 573 bcl1, AspAspLysValPheProGlyGlySerHisThrTyrValTrpGlnValLeuLysGluAsn
601      GATGATAAAGTCTTCCCTGGTGGAAGCCATACATATGTCTGGCAGGTCCTGAAAGAGAAT
         CTACTATTTCAGAAGGGACCACCTTCGGTATGTATACAGACCGTCCAGGACTTTCTCTTA 632 nde1, GlyProMetAlaSerAspProLeuCysLeuThrTyrSerTyrLeuSerHisValAspLeu
661      GGTCCAATGGCCTCTGACCCACTGTGCCTTACCTACTCATATCTTTCTCATGTGGACCTG
         CCAGGTTACCGGAGACTGGGTGACACGGAATGGATGAGTATAGAAAGAGTACACCTGGAC ValLysAspLeuAsnSerGlyLeuIleGlyAlaLeuLeuValCysArgGluGlySerLeu
721      GTAAAAGACTTGAATTCAGGCCTCATTGGAGCCCTACTAGTATGTAGAGAAGGGAGTCTG
         CATTTTCTGAACTTAAGTCCGGAGTAACCTCGGGATGATCATACATCTCTTCCCTCAGAC 732 ecor1, 738 stu1, 756 spe1, 779 bal1, AlaLysGluLysThrGlnThrLeuHisLysPheIleLeuLeuPheAlaValPheAspGlu
781      GCCAAGGAAAAGACACAGACCTTGCACAAATTTATACTACTTTTTGCTGTATTTGATGAA
         CGGTTCCTTTTCTGTGTCTGGAACGTGTTTAAATATGATGAAAAACGACATAAACTACTT GlyLysSerTrpHisSerGluThrLysAsnSerLeuMetGlnAspArgAspAlaAlaSer
841      GGGAAAAGTTGGCACTCAGAAACAAAGAACTCCTTGATGCAGGATAGGGATGCTGCATCT
         CCCTTTTCAACCGTGAGTCTTTGTTTCTTGAGGAACTACGTCCTATCCCTACGACGTAGA AlaArgAlaTrpProLysMetHisThrValAsnGlyTyrValAsnArgSerLeuProGly
901      GCTCGGGCCTGGCCTAAAATGCACACAGTCAATGGTTATGTAAACAGGTCTCTGCCAGGT
         CGAGCCCGGACCGGATTTTACGTGTGTCAGTTACCAATACATTTGTCCAGAGACGGTCCA LeuIleGlyCysHisArgLysSerValTyrTrpHisValIleGlyMetGlyThrThrPro
961      CTGATTGGATGCCACAGGAAATCAGTCTATTGGCATGTGATTGGAATGGGCACCACTCCT
         GACTAACCTACGGTGTCCTTTAGTCAGATAACCGTACACTAACCTTACCCGTGGTGAGGA GluValHisSerIlePheLeuGluGlyHisThrPheLeuValArgAsnHisArgGlnAla
1021     GAAGTGCACTCAATATTCCTCGAAGGTCACACATTTCTTGTGAGGAACCATCGCCAGGCG
         CTTCACGTGAGTTATAAGGAGCTTCCAGTGTGTAAAGAACACTCCTTGGTAGCGGTCCGC 1032 ssp1, SerLeuGluIleSerProIleThrPheLeuThrAlaGlnThrLeuLeuMetAspLeuGly
1081     TCCTTGGAAATCTCGCCAATAACTTTCCTTACTGCTCAAACACTCTTGATGGACCTTGGA
         AGGAACCTTTAGAGCGGTTATTGAAAGGAATGACGAGTTTGTGAGAACTACCTGGAACCT GlnPheLeuLeuPheCysHisIleSerSerHisGlnHisAspGlyMetGluAlaTyrVal
1141     CAGTTTCTACTGTTTTGTCATATCTCTTCCCACCAACATGATGGCATGGAAGCTTATGTC
         GTCAAAGATGACAAAACAGTATAGAGAAGGGTGGTTGTACTACCGTACCTTCGAATACAG 1173 bstXI, 1190 hind111, LysValAspSerCysProGluGluProGlnLeuArgMetLysAsnAsnGluGluAlaGlu
1201     AAAGTAGACAGCTGTCCAGAGGAACCCCAACTACGAATGAAAAATAATGAAGAAGCGGAA
         TTTCATCTGTCGACAGGTCTCCTTGGGGTTGATGCTTACTTTTTATTACTTCTTCGCCTT 1209 pvu11,
```

FIG. IC

```
             AspTyrAspAspAspLeuThrAspSerGluMetAspValValArgPheAspAspAsn
1261         GACTATGATGATGATCTTACTGATTCTGAAATGGATGTGGTCAGGTTTGATGATGACAAC
             CTGATACTACTACTAGAATGACTAAGACTTTACCTACACCAGTCCAAACTACTACTGTTG

SerProSerPheIleGlnIleArgSerValAlaLysLysHisProLysThrTrpValHis
1321         TCTCCTTCCTTTATCCAAATTCGCTCAGTTGCCAAGAAGCATCCTAAAACTTGGGTACAT
             AGAGGAAGGAAATAGGTTTAAGCGAGTCAACGGTTCTTCGTAGGATTTTGAACCCATGTA

TyrIleAlaAlaGluGluGluAspTrpAspTyrAlaProLeuValLeuAlaProAspAsp
1381         TACATTGCTGCTGAAGAGGAGGACTGGGACTATGCTCCCTTAGTCCTCGCCCCCGATGAC
             ATGTAACGACGACTTCTCCTCCTGACCCTGATACGAGGGAATCAGGAGCGGGGCTACTG

ArgSerTyrLysSerGlnTyrLeuAsnAsnGlyProGlnArgIleGlyArgLysTyrLys
1441         AGAAGTTATAAAAGTCAATATTTGAACAATGGCCCTCAGCGGATTGGTAGGAAGTACAAA
             TCTTCAATATTTTCAGTTATAAACTTGTTACCGGGAGTCGCCTAACCATCCTTCATGTTT 1457 ssp1, LysValArgPheMetAlaTyrThrAspGluThrPheLysThrArgGluAlaIleGlnHis
1501         AAAGTCCGATTTATGGCATACACAGATGAAACCTTTAAGACTCGTGAAGCTATTCAGCAT
             TTTCAGGCTAAATACCGTATGTGTCTACTTTGGAAATTCTGAGCACTTCGATAAGTCGTA 1546 xmn1, GluSerGlyIleLeuGlyProLeuLeuTyrGlyGluValGlyAspThrLeuLeuIleIle
1561         GAATCAGGAATCTTGGGACCTTTACTTTATGGGGAAGTTGGAGACACACTGTTGATTATA
             CTTAGTCCTTAGAACCCTGGAAATGAAATACCCCTTCAACCTCTGTGTGACAACTAATAT PheLysAsnGlnAlaSerArgProTyrAsnIleTyrProHisGlyIleThrAspValArg
1621         TTTAAGAATCAAGCAAGCAGACCATATAACATCTACCCTCACGGAATCACTGATGTCCGT
             AAATTCTTAGTTCGTTCGTCTGGTATATTGTAGATGGGAGTGCCTTAGTGACTACAGGCA ProLeuTyrSerArgArgLeuProLysGlyValLysHisLeuLysAspPheProIleLeu
1681         CCTTTGTATTCAAGGAGATTACCAAAAGGTGTAAAACATTTGAAGGATTTTCCAATTCTG
             GGAAACATAAGTTCCTCTAATGGTTTTCCACATTTTGTAAACTTCCTAAAAGGTTAAGAC ProGlyGluIlePheLysTyrLysTrpThrValThrValGluAspGlyProThrLysSer
1741         CCAGGAGAAATATTCAAATATAAATGGACAGTGACTGTAGAAGATGGGCCAACTAAATCA
             GGTCCTCTTTATAAGTTTATATTTACCTGTCACTGACATCTTCTACCCGGTTGATTTAGT 1749 ssp1, AspProArgCysLeuThrArgTyrTyrSerSerPheValAsnMetGluArgAspLeuAla
1801         GATCCTCGGTGCCTGACCCGCTATTACTCTAGTTTCGTTAATATGGAGAGAGATCTAGCT
             CTAGGAGCCACGGACTGGGCGATAATGAGATCAAAGCAATTATACCTCTCTCTAGATCGA 1851 bgl11, SerGlyLeuIleGlyProLeuLeuIleCysTyrLysGluSerValAspGlnArgGlyAsn
1861         TCAGGACTCATTGGCCCTCTCCTCATCTGCTACAAAGAATCTGTAGATCAAAGAGGAAAC
             AGTCCTGAGTAACCGGGAGAGGAGTAGACGATGTTTCTTAGACATCTAGTTTCTCCTTTG GlnIleMetSerAspLysArgAsnValIleLeuPheSerValPheAspGluAsnArgSer
1921         CAGATAATGTCAGACAAGAGGAATGTCATCCTGTTTTCTGTATTTGATGAGAACCGAAGC
             GTCTATTACAGTCTGTTCTCCTTACAGTAGGACAAAAGACATAAACTACTCTTGGCTTCG TrpTyrLeuThrGluAsnIleGlnArgPheLeuProAsnProAlaGlyValGlnLeuGlu
1981         TGGTACCTCACAGAGAATATACAACGCTTTCTCCCCAATCCAGCTGGAGTGCAGCTTGAG
             ACCATGGAGTGTCTCTTATATGTTGCGAAAGAGGGGTTAGGTCGACCTCACGTCGAACTC 1982 kpn1, 2021 pvu11, 2040 bamh1, AspProGluPheGlnAlaSerAsnIleMetHisSerIleAsnGlyTyrValPheAspSer
2041         GATCCAGAGTTCCAAGCCTCCAACATCATGCACAGCATCAATGGCTATGTTTTTGATAGT
             CTAGGTCTCAAGGTTCGGAGGTTGTAGTACGTGTCGTAGTTACCGATACAAAAACTATCA LeuGlnLeuSerValCysLeuHisGluValAlaTyrTrpTyrIleLeuSerIleGlyAla
2101         TTGCAGTTGTCAGTTTGTTTGCATGAGGTGGCATACTGGTACATTCTAAGCATTGGAGCA
             AACGTCAACAGTCAAACAAACGTACTCCACCGTATGACCATGTAAGATTCGTAACCTCGT GlnThrAspPheLeuSerValPhePheSerGlyTyrThrPheLysHisLysMetValTyr
2161         CAGACTGACTTCCTTTCTGTCTTTCTTCTCTGGATATACCTTCAAACACAAAATGGTCTAT
             GTCTGACTGAAGGAAAGACAGAAGAAGAGACCTATATGGAAGTTTGTGTTTTACCAGATA GluAspThrLeuThrLeuPheProPheSerGlyGluThrValPheMetSerMetGluAsn
2221         GAAGACACACTCACCCTATTCCCATTCTCAGGAGAAACTGTCTTCATGTCGATGGAAAAC
             CTTCTGTGTGAGTGGGATAAGGGTAAGAGTCCTCTTTGACAGAAGTACAGCTACCTTTTG ProGlyLeuTrpIleLeuGlyCysHisAsnSerAspPheArgAsnArgGlyMetThrAla
2281         CCAGGTCTATGGATTCTGGGGTGCCACAACTCAGACTTTCGGAACAGAGGCATGACCGCC
             GGTCCAGATACCTAAGACCCCACGGTGTTGAGTCTGAAAGCCTTGTCTCCGTACTGGCGG 2281 bstXI,
```

FIG.ID

```
       LeuLeuLysValSerSerCysAspLysAsnThrGlyAspTyrTyrGluAspSerTyrGlu
2341   TTACTGAAGGTTTCTAGTTGTGACAAGAACACTGGTGATTATTACGAGGACAGTTATGAA
       AATGACTTCCAAAGATCAACACTGTTCTTGTGACCACTAATAATGCTCCTGTCAATACTT

AspIleSerAlaTyrLeuLeuSerLysAsnAsnAlaIleGluProArgSerPheSerGln
2401   GATATTTCAGCATACTTGCTGAGTAAAAACAATGCCATTGAACCAAGAAGCTTCTCCCAG
       CTATAAAGTCGTATGAACGACTCATTTTTGTTACGGTAACTTGGTTCTTCGAAGAGGGTC 2448 hind111, 2460 ecor1, AsnSerArgHisProSerThrArgGlnLysGlnPheAsnAlaThrThrIleProGluAsn
2461   AATTCAAGACACCCTAGCACTAGGCAAAAGCAATTTAATGCCACCACAATTCCAGAAAAT
       TTAAGTTCTGTGGGATCGTGATCCGTTTTCGTTAAATTACGGTGGTGTTAAGGTCTTTTA AspIleGluLysThrAspProTrpPheAlaHisArgThrProMetProLysIleGlnAsn
2521   GACATAGAGAAGACTGACCCTTGGTTTGCACACAGAACACCTATGCCTAAAATACAAAAT
       CTGTATCTCTTCTGACTGGGAACCAAACGTGTGTCTTGTGGATACGGATTTTATGTTTTA ValSerSerSerAspLeuLeuMetLeuLeuArgGlnSerProThrProHisGlyLeuSer
2581   GTCTCCTCTAGTGATTTGTTGATGCTCTTGCGACAGAGTCCTACTCCACATGGGCTATCC
       CAGAGGAGATCACTAAACAACTACGAGAACGCTGTCTCAGGATGAGGTGTACCCGATAGG 2612 tthIII1, LeuSerAspLeuGlnGluAlaLysTyrGluThrPheSerAspAspProSerProGlyAla
2641   TTATCTGATCTCCAAGAAGCCAAATATGAGACTTTTTCTGATGATCCATCACCTGGAGCA
       AATAGACTAGAGGTTCTTCGGTTTATACTCTGAAAAAGACTACTAGGTAGTGGACCTCGT IleAspSerAsnAsnSerLeuSerGluMetThrHisPheArgProGlnLeuHisHisSer
2701   ATAGACAGTAATAACAGCCTGTCTGAAATGACACACTTCAGGCCACAGCTCCATCACAGT
       TATCTGTCATTATTGTCGGACAGACTTTACTGTGTGAAGTCCGGTGTCGAGGTAGTGTCA 2751 bstXI, GlyAspMetValPheThrProGluSerGlyLeuGlnLeuArgLeuAsnGluLysLeuGly
2761   GGGGACATGGTATTTACCCCTGAGTCAGGCCTCCAATTAAGGATTAAATGAGAAACTGGGG
       CCCCTGTACCATAAATGGGGACTCAGTCCGGAGGTTAATTCTAATTTACTCTTTGACCCC 2780 tthIII1, 2787 stu1, ThrThrAlaAlaThrGluLeuLysLysLeuAspPheLysValSerSerThrSerAsnAsn
2821   ACAACTGCAGCAACAGAGTTGAAGAAACTTGATTTCAAAGTTTCTAGTACATCAAATAAT
       TGTTGACGTCGTTGTCTCAACTTCTTTGAACTAAAGTTTCAAAGATCATGTAGTTTATTA 2825 pst1, LeuIleSerThrIleProSerAspAsnLeuAlaAlaGlyThrAspAsnThrSerSerLeu
2881   CTGATTTCAACAATTCCATCAGACAATTTGGCAGCAGGTACTGATAATACAAGTTCCTTA
       GACTAAAGTTGTTAAGGTAGTCTGTTAAACCGTCGTCCATGACTATTATGTTCAAGGAAT 2936 mstII, GlyProProSerMetProValHisTyrAspSerGlnLeuAspThrThrLeuPheGlyLys
2941   GGACCCCCAAGTATGCCAGTTCATTATGATAGTCAATTAGATACCACTCTATTTGGCAAA
       CCTGGGGGTTCATACGGTCAAGTAATACTATCAGTTAATCTATGGTGAGATAAACCGTTT LysSerSerProLeuThrGluSerGlyGlyProLeuSerLeuSerGluGluAsnAsnAsp
3001   AAGTCATCTCCCCTTACTGAGTCTGGTGGACCTCTGAGCTTGAGTGAAGAAAATAATGAT
       TTCAGTAGAGGGGAATGACTCAGACCACCTGGAGACTCGAACTCACTTCTTTTATTACTA SerLysLeuLeuGluSerGlyLeuMetAsnSerGlnGluSerSerTrpGlyLysAsnVal
3061   TCAAAGTTGTTAGAATCAGGTTTAATGAATAGCCAAGAAAGTTCATGGGGAAAAAATGTA
       AGTTTCAACAATCTTAGTCCAAATTACTTATCGGTTCTTTCAAGTACCCCTTTTTTACAT SerSerThrGluSerGlyArgLeuPheLysGlyLysArgAlaHisGlyProAlaLeuLeu
3121   TCGTCAACAGAGAGTGGTAGGTTATTTAAAGGGAAAAGAGCTCATGGACCTGCTTTGTTG
       AGCAGTTGTCTCTCACCATCCAATAAATTTCCCTTTTCTCGAGTACCTGGACGAAACAAC 3145 aha111, 3158 sac1, ThrLysAspAsnAlaLeuPheLysValSerIleSerLeuLeuLysThrAsnLysThrSer
3181   ACTAAAGATAATGCCTTATTCAAAGTTAGCATCTCTTTGTTAAAGACAAACAAAACTTCC
       TGATTTCTATTACGGAATAAGTTTCAATCGTAGAGAAACAATTTCTGTTTGTTTTGAAGG AsnAsnSerAlaThrAsnArgLysThrHisIleAspGlyProSerLeuLeuIleGluAsn
3241   AATAATTCAGCAACTAATAGAAAGACTCACATTGATGGCCCATCATTATTAATTGAGAAT
       TTATTAAGTCGTTGATTATCTTTCTGAGTGTAACTACCGGGTAGTAATAATTAACTCTTA SerProSerValTrpGlnAsnIleLeuGluSerAspThrGluPheLysLysValThrPro
3301   AGTCCATCAGTCTGGCAAAATATATTAGAAAGTGACACTGAGTTTAAAAAAGTGACACCT
       TCAGGTAGTCAGACCGTTTTATATAATCTTTCACTGTGACTCAAATTTTTTCACTGTGGA 3304 bstXI, 3343 aha111,
```

FIG. IE

```
        LeuIleHisAspArgMetLeuMetAspLysAsnAlaThrAlaLeuArgLeuAsnHisMet
3361    TTGATTCATGACAGAATGCTTATGGACAAAAATGCTACAGCTTTGAGGCTAAATCATATG
        AACTAAGTACTGTCTTACGAATACCTGTTTTTACGATGTCGAAACTCCGATTTAGTATAC 3374 bsm1, 3415 nde1, SerAsnLysThrThrSerSerLysAsnMetGluMetValGlnGlnLysLysGluGlyPro
3421    TCAAATAAAACTACTTCATCAAAAAACATGGAAATGGTCCAACAGAAAAAAGAGGGCCCC
        AGTTTATTTTGATGAAGTAGTTTTTTGTACCTTTACCAGGTTGTCTTTTTTCTCCCGGGG 3474 apa1, IleProProAspAlaGlnAsnProAspMetSerPhePheLysMetLeuPheLeuProGlu
3481    ATTCCACCAGATGCACAAAATCCAGATATGTCGTTCTTTAAGATGCTATTCTTGCCAGAA
        TAAGGTGGTCTACGTGTTTTAGGTCTATACAGCAAGAAATTCTACGATAAGAACGGTCTT SerAlaArgTrpIleGlnArgThrHisGlyLysAsnSerLeuAsnSerGlyGlnGlyPro
3541    TCAGCAAGGTGGATACAAAGGACTCATGGAAAGAACTCTCTGAACTCTGGGCAAGGCCCC
        AGTCGTTCCACCTATGTTTCCTGAGTACCTTTCTTGAGAGACTTGAGACCCGTTCCGGGG SerProLysGlnLeuValSerLeuGlyProGluLysSerValGluGlyGlnAsnPheLeu
3601    AGTCCAAAGCAATTAGTATCCTTAGGACCAGAAAAATCTGTGGAAGGTCAGAATTTCTTG
        TCAGGTTTCGTTAATCATAGGAATCCTGGTCTTTTTAGACACCTTCCAGTCTTAAAGAAC 3620 mstII, SerGluLysAsnLysValValValGlyLysGlyGluPheThrLysAspValGlyLeuLys
3661    TCTGAGAAAAACAAAGTGGTAGTAGGAAAGGGTGAATTTACAAAGGACGTAGGACTCAAA
        AGACTCTTTTTGTTTCACCATCATCCTTTCCCACTTAAATGTTTCCTGCATCCTGAGTTT GluMetValPheProSerSerArgAsnLeuPheLeuThrAsnLeuAspAsnLeuHisGlu
3721    GAGATGGTTTTTCCAAGCAGCAGAAACCTATTTCTTACTAACTTGGATAATTTACATGAA
        CTCTACCAAAAAGGTTCGTCGTCTTTGGATAAAGAATGATTGAACCTATTAAATGTACTT AsnAsnThrHisAsnGlnGluLysLysIleGlnGluGluIleGluLysLysGluThrLeu
3781    AATAATACACACAATCAAGAAAAAAAAATTCAGGAAGAAATAGAAAAGAAGGAAACATTA
        TTATTATGTGTGTTAGTTCTTTTTTTTTAAGTCCTTCTTTATCTTTTCTTCCTTTGTAAT IleGlnGluAsnValValLeuProGlnIleHisThrValThrGlyThrLysAsnPheMet
3841    ATCCAAGAGAATGTAGTTTTGCCTCAGATACATACAGTGACTGGCACTAAGAATTTCATG
        TAGGTTCTCTTACATCAAAACGGAGTCTATGTATGTCACTGACCGTGATTCTTAAAGTAC LysAsnLeuPheLeuLeuSerThrArgGlnAsnValGluGlySerTyrAspGlyAlaTyr
3901    AAGAACCTTTTTCTTACTGAGCACTAGGCAAAATGTAGAAGGTTCATATGACGGGGCATAT
        TTCTTGGAAAAGAATGACTCGTGATCCGTTTTACATCTTCCAAGTATACTGCCCCGTATA 3903 xmn1, 3944 nde1, 3956 nde1, AlaProValLeuGlnAspPheArgSerLeuAsnAspSerThrAsnArgThrLysLysHis
3961    GCTCCAGTACTTCAAGATTTTAGGTCATTAAATGATTCAACAAATAGAACAAAGAAACAC
        CGAGGTCATGAAGTTCTAAAATCCAGTAATTTACTAAGTTGTTTATCTTGTTTCTTTGTG 3966 sca1, ThrAlaHisPheSerLysLysGlyGluGluGluAsnLeuGluGlyLeuGlyAsnGlnThr
4021    ACAGCTCATTTCTCAAAAAAAGGGGAGGAAGAAAACTTGGAAGGCTTTGGGAAATCAAACC
        TGTCGAGTAAAGAGTTTTTTTCCCCTCCTTCTTTTGAACCTTCCGAACCCTTTAGTTTGG LysGlnIleValGluLysTyrAlaCysThrThrArgIleSerProAsnThrSerGlnGln
4081    AAGCAAATTGTAGAGAAATATGCATGCACCACAAGGATATCTCCTAATACAAGCCAGCAG
        TTCGTTTAACATCTCTTTATACGTACGTGGTGTTCCTATAGAGGATTATGTTCGGTCGTC 4100 ava3, 4102 sph1, 4116 ecor5, AsnPheValThrGlnArgSerLysArgAlaLeuLysGlnPheArgLeuProLeuGluGlu
4141    AATTTTGTCACGCAACGTAGTAAGAGAGCTTTGAAACAATTCAGACTCCCACTAGAAGAA    F8-100
        TTAAAACAGTGCGTTGCATCATTCTCTCGAAACTTTGTTAAGTCTGAGGGTGATCTTCTT 4173 xmn1, ThrGluLeuGluLysArgIleIleValAspAspThrSerThrGlnTrpSerLysAsnMet
4201    ACAGAACTTGAAAAAAGGATAATTGTGGATGACACCTCAACCCAGTGGTCCAAAAACATG
        TGTCTTGAACTTTTTTCCTATTAACACCTACTGTGGAGTTGGGTCACCAGGTTTTTGTAC LysHisLeuThrProSerThrLeuThrGlnIleAspTyrAsnGluLysGluLysGlyAla
4261    AAACATTTGACCCCGAGCACCCTCACACAGATAGACTACAATGAGAAGGAGAAAGGGGCC
        TTTGTAAACTGGGGCTCGTGGGAGTGTGTCTATCTGATGTTACTCTTCCTCTTTCCCCGG IleThrGlnSerProLeuSerAspCysLeuThrArgSerHisSerIleProGlnAlaAsn
4321    ATTACTCAGTCTCCCTTATCAGATTGCCTTACGAGGAGTCATAGCATCCCTCAAGCAAAT
        TAATGAGTCAGAGGGAATAGTCTAACGGAATGCTCCTCAGTATCGTAGGGAGTTCGTTTA
``` internal primer for cDNA synthesis

FIG.1F

```
       ArgSerProLeuProIleAlaLysValSerSerPheProSerIleArgProIleTyrLeu
 4381  AGATCTCCATTACCCATTGCAAAGGTATCATCATTTCCATCTATTAGACCTATATATCTG
       TCTAGAGGTAATGGGTAACGTTTCCATAGTAGTAAAGGTAGATAATCTGGATATATAGAC 4381 bgl11, ThrArgValLeuPheGlnAspAsnSerSerHisLeuProAlaAlaSerTyrArgLysLys
 4441  ACCAGGGTCCTATTCCAAGACAACTCTTCTCATCTTCCAGCAGCATCTTATAGAAAGAAA
       TGGTCCCAGGATAAGGTTCTGTTGAGAAGAGTAGAAGGTCGTCGTAGAATATCTTTCTTT AspSerGlyValGlnGluSerSerHisPheLeuGlnGlyAlaLysLysAsnAsnLeuSer
 4501  GATTCTGGGGTCCAAGAAAGCAGTCATTTCTTACAAGGAGCCAAAAAAAATAACCTTTCT
       CTAAGACCCCAGGTTCTTTCGTCAGTAAAGAATGTTCCTCGGTTTTTTTATTGGAAAGA LeuAlaIleLeuThrLeuGluMetThrGlyAspGlnArgGluValGlySerLeuGlyThr
 4561  TTAGCCATTCTAACCTTGGAGATGACTGGTGATCAAAGAGAGGTTGGCTCCCTGGGGACA
       AATCGGTAAGATTGGAACCTCTACTGACCACTAGTTTCTCTCCAACCGAGGGACCCCTGT 4590 bcl1, SerAlaThrAsnSerValThrTyrLysLysValGluAsnThrValLeuProLysProAsp
 4621  AGTGCCACAAATTCAGTCACATACAAGAAAGTTGAGAACACTGTTCTCCCGAAACCAGAC
       TCACGGTGTTTAAGTCAGTGTATGTTCTTTCAACTCTTGTGACAAGAGGGCTTTGGTCTG LeuProLysThrSerGlyLysValGluLeuLeuProLysValHisIleTyrGlnLysAsp
 4681  TTGCCCAAAACATCTGGCAAAGTTGAATTGCTTCCAAAAGTTCACATTTATCAGAAGGAC
       AACGGGTTTTGTAGACCGTTTCAACTTAACGAAGGTTTTCAAGTGTAAATAGTCTTCCTG 4705 xmn1, LeuPheProThrGluThrSerAsnGlySerProGlyHisLeuAspLeuValGluGlySer
 4741  CTATTCCCTACGGAAACTAGCAATGGGTCTCCTGGCCATCTGGATCTCGTGGAAGGGAGC
       GATAAGGGATGCCTTTGATCGTTACCCAGAGGACCGGTAGACCTAGAGCACCTTCCCTCG 4773 bal1, LeuLeuGlnGlyThrGluGlyAlaIleLysTrpAsnGluAlaAsnArgProGlyLysVal
 4801  CTTCTTCAGGGAACAGAGGGAGCGATTAAGTGGAATGAAGCAAACAGACCTGGAAAAGTT
       GAAGAAGTCCCTTGTCTCCCTCGCTAATTCACCTTACTTCGTTTGTCTGGACCTTTTCAA ProPheLeuArgValAlaThrGluSerSerAlaLysThrProSerLysLeuLeuAspPro
 4861  CCCTTTCTGAGAGTAGCAACAGAAAGCTCTGCAAAGACTCCCTCCAAGCTATTGGATCCT
       GGGAAAGACTCTCATCGTTGTCTTTCGAGACGTTTCTGAGGGAGGTTCGATAACCTAGGA 4904 bstXI, 4914 bamh1, LeuAlaTrpAspAsnHisTyrGlyThrGlnIleProLysGluGluTrpLysSerGlnGlu
 4921  CTTGCTTGGGATAACCACTATGGTACTCAGATACCAAAAGAAGAGTGGAAATCCAAGAG
       GAACGAACCCTATTGGTGATACCATGAGTCTATGGTTTTCTTCTCACCTTTAGGGTTCTC LysSerProGluLysThrAlaPheLysLysLysAspThrIleLeuSerLeuAsnAlaCys
 4981  AAGTCACCAGAAAAAACAGCTTTTAAGAAAAAGGATACCATTTTGTCCCTGAACGCTTGT
       TTCAGTGGTCTTTTTTGTCGAAAATTCTTTTTCCTATGGTAAAACAGGGACTTGCGAACA GluSerAsnHisAlaIleAlaAlaIleAsnGluGlyGlnAsnLysProGluIleGluVal
 5041  GAAAGCAATCATGCAATAGCAGCAATAAATGAGGGACAAAATAAGCCCGAAATAGAAGTC
       CTTTCGTTAGTACGTTATCGTCGTTATTTACTCCCTGTTTTATTCGGGCTTTATCTTCAG ThrTrpAlaLysGlnGlyArgThrGluArgLeuCysSerGlnAsnProProValLeuLys
 5101  ACCTGGGCAAAGCAAGGTAGGACTGAAAGGCTGTGCTCTCAAAACCCACCAGTCTTGAAA
       TGGACCCGTTTCGTTCCATCCTGACTTTCCGACACGAGAGTTTTGGGTGGTCAGAACTTT ArgHisGlnArgGluIleThrArgThrThrLeuGlnSerAspGlnGluGluIleAspTyr
 5161  CGCCATCAACGGGAAATAACTCGTACTACTCTTCAGTCAGATCAAGAGGAAATTGACTAT
       GCGGTAGTTGCCCTTTATTGAGCATGATGAGAAGTCAGTCTAGTTCTCCTTTAACTGATA AspAspThrIleSerValGluMetLysLysGluAspPheAspIleTyrAspGluAspGlu
 5221  GATGATACCATATCAGTTGAAATGAAGAAGGAAGATTTTGACATTTATGATGAGGATGAA
       CTACTATGGTATAGTCAACTTTACTTCTTCCTTCTAAAACTGTAAATACTACTCCTACTT AsnGlnSerProArgSerPheGlnLysLysThrArgHisTyrPheIleAlaAlaValGlu
 5281  AATCAGAGCCCCCGCAGCTTTCAAAAGAAAACACGACACTATTTTATTGCTGCAGTGGAG
       TTAGTCTCGGGGGCGTCGAAAGTTTTCTTTTGTGCTGTGATAAAATAACGACGTCACCTC 5330 pst1, ArgLeuTrpAspTyrGlyMetSerSerSerProHisValLeuArgAsnArgAlaGlnSer
 5341  AGGCTCTGGGATTATGGGATGAGTAGCTCCCCACATGTTCTAAGAAACAGGGCTCAGAGT
       TCCGAGACCCTAATACCCTACTCATCGAGGGGTGTACAAGATTCTTTGTCCCGAGTCTCA GlySerValProGlnPheLysLysValValPheGlnGluPheThrAspGlySerPheThr
 5401  GGCAGTGTCCCTCAGTTCAAGAAAGTTGTTTTCCAGGAATTTACTGATGGCTCCTTTACT
       CCGTCACAGGGAGTCAAGTTCTTTCAACAAAAGGTCCTTAAATGACTACCGAGGAAATGA
```

FIG.1G

```
       GlnProLeuTyrArgGlyGluLeuAsnGluHisLeuGlyLeuLeuGlyProTyrIleArg
5461   CAGCCCTTATACCGTGGAGAACTAAATGAACATTTGGGACTCCTGGGGCCATATATAAGA
       GTCGGGAATATGGCACCTCTTGATTTACTTGTAAACCCTGAGGACCCCGGTATATATTCT

AlaGluValGluAspAsnIleMetValThrPheArgAsnGlnAlaSerArgProTyrSer
5521   GCAGAAGTTGAAGATAATATCATGGTAACTTTCAGAAATCAGGCCTCTCGTCCCTATTCC
       CGTCTTCAACTTCTATTATAGTACCATTGAAAGTCTTTAGTCCGGAGAGCAGGGATAAGG 5561 stu1, PheTyrSerSerLeuIleSerTyrGluGluAspGlnArgGlnGlyAlaGluProArgLys
5581   TTCTATTCTAGCCTTATTTCTTATGAGGAAGATCAGAGGCAAGGAGCAGAACCTAGAAAA
       AAGATAAGATCGGAATAAAGAATACTCCTTCTAGTCTCCGTTCCTCGTCTTGGATCTTTT AsnPheValLysProAsnGluThrLysThrTyrPheTrpLysValGlnHisHisMetAla
5641   AACTTTGTCAAGCCTAATGAAACCAAAACTTACTTTTGGAAAGTGCAACATCATATGGCA
       TTGAAACAGTTCGGATTACTTTGGTTTTGAATGAAAACCTTTCACGTTGTAGTATACCGT 5692 nde1, ProThrLysAspGluPheAspCysLysAlaTrpAlaTyrPheSerAspValAspLeuGlu
5701   CCCACTAAAGATGAGTTTGACTGCAAAGCCTGGGCTTATTTCTCTGATGTTGACCTGGAA
       GGGTGATTTCTACTCAAACTGACGTTTCGGACCCGAATAAAGAGACTACAACTGGACCTT LysAspValHisSerGlyLeuIleGlyProLeuLeuValCysHisThrAsnThrLeuAsn
5761   AAAGATGTGCACTCAGGCCTGATTGGACCCCTTCTGGTCTGCCACACTAACACACTGAAC
       TTTCTACACGTGAGTCCGGACTAACCTGGGGAAGACCAGACGGTGTGATTGTGTGACTTG 5775 stu1, ProAlaHisGlyArgGlnValThrValGlnGluPheAlaLeuPhePheThrIlePheAsp
5821   CCTGCTCATGGGAGACAAGTGACAGTACAGGAATTTGCTCTGTTTTTCACCATCTTTGAT
       GGACGAGTACCCTCTGTTCACTGTCATGTCCTTAAACGAGACAAAAAGTGGTAGAAACTA GluThrLysSerTrpTyrPheThrGluAsnMetGluArgAsnCysArgAlaProCysAsn
5881   GAGACCAAAAGCTGGTACTTCACTGAAAATATGGAAAGAAACTGCAGGGCTCCCTGCAAT
       CTCTGGTTTTCGACCATGAAGTGACTTTTATACCTTTCTTTGACGTCCCGAGGGACGTTA 5922 pst1, IleGlnMetGluAspProThrPheLysGluAsnTyrArgPheHisAlaIleAsnGlyTyr
5941   ATCCAGATGGAAGATCCCACTTTTAAAGAGAATTATCGCTTCCATGCAATCAATGGCTAC
       TAGGTCTACCTTCTAGGGTGAAAATTTCTCTTAATAGCGAAGGTACGTTAGTTACCGATG 5962 aha111, IleMetAspThrLeuProGlyLeuValMetAlaGlnAspGlnArgIleArgTrpTyrLeu
6001   ATAATGGATACACTACCTGGCTTAGTAATGGCTCAGGATCAAAGGATTCGATGGTATCTG
       TATTACCTATGTGATGGACCGAATCATTACCGAGTCCTAGTTTCCTAAGCTACCATAGAC LeuSerMetGlySerAsnGluAsnIleHisSerIleHisPheSerGlyHisValPheThr
6061   CTCAGCATGGGCAGCAATGAAAACATCCATTCTATTCATTTCAGTGGACATGTGTTCACT
       GAGTCGTACCCGTCGTTACTTTTGTAGGTAAGATAAGTAAAGTCACCTGTACACAAGTGA ValArgLysLysGluGluTyrLysMetAlaLeuTyrAsnLeuTyrProGlyValPheGlu
6121   GTACGAAAAAAGGAGGAGTATAAAATGGCACTGTACAATCTCTATCCAGGTGTTTTTGAG
       CATGCTTTTTTTCTCCTCATATTTTACCGTGACATGTTAGAGATAGGTCCACAAAAACTC ThrValGluMetLeuProSerLysAlaGlyIleTrpArgValGluCysLeuIleGlyGlu
6181   ACAGTGGAAATGTTACCATCCAAAGCTGGAATTTGGCGGGTGGAATGCCTTATTGGCGAG
       TGTCACCTTTACAATGGTAGGTTTCGACCTTAAACCGCCCACCTTACGGAATAACCGCTC 6223 bsm1,  6227 bgl1, HisLeuHisAlaGlyMetSerThrLeuPheLeuValTyrSerAsnLysCysGlnThrPro
6241   CATCTACATGCTGGGATGAGCACACTTTTTCTGGTGTACAGCAATAAGTGTCAGACTCCC
       GTAGATGTACGACCCTACTCGTGTGAAAAAGACCACATGTCGTTATTCACAGTCTGAGGG LeuGlyMetAlaSerGlyHisIleArgAspPheGlnIleThrAlaSerGlyGlnTyrGly
6301   CTGGGAATGGCTTCTGGACACATTAGAGATTTTCAGATTACAGCTTCAGGACAATATGGA
       GACCCTTACCGAAGACCTGTGTAATCTCTAAAAGTCTAATGTCGAAGTCCTGTTATACCT 6305 xmn1, GlnTrpAlaProLysLeuAlaArgLeuHisTyrSerGlySerIleAsnAlaTrpSerThr
6361   CAGTGGGCCCCCAAAGCTGGCCAGACTTCATTATTCCGGATCAATCAATGCCTGGAGCACC
       GTCACCCGGGGTTTCGACCGGTCTGAAGTAATAAGGCCTAGTTAGTTACGGACCTCGTGG 6365 apa1,  6377 bal1, LysGluProPheSerTrpIleLysValAspLeuLeuAlaProMetIleIleHisGlyIle
6421   AAGGAGCCCTTTTCTTGGATCAAGGTGGATCTGTTGGCACCAATGATTATTCACGGCATC
       TTCCTCGGGAAAAGAACCTAGTTCCACCTAGACAACCGTGGTTACTAATAAGTGCCGTAG
```

FIG.IH

```
            LysThrGlnGlyAlaArgGlnLysPheSerSerLeuTyrIleSerGlnPheIleIleMet
6481        AAGACCCAGGGTGCCCGTCAGAAGTTCTCCAGCCTCTACATCTCTCAGTTTATCATCATG
            TTCTGGGTCCCACGGGCAGTCTTCAAGAGGTCGGAGATGTAGAGAGTCAAATAGTAGTAC

TyrSerLeuAspGlyLysLysTrpGlnThrTyrArgGlyAsnSerThrGlyThrLeuMet
6541        TATAGTCTTGATGGGAAGAAGTGGCAGACTTATCGAGGAAATTCCACTGGAACCTTAATG
            ATATCAGAACTACCCTTCTTCACCGTCTGAATAGCTCCTTTAAGGTGACCTTGGAATTAC

ValPhePheGlyAsnValAspSerSerGlyIleLysHisAsnIlePheAsnProProIle
6601        GTCTTCTTTGGCAATGTGGATTCATCTGGGATAAAACACAATATTTTTAACCCTCCAATT
            CAGAAGAAACCGTTACACCTAAGTAGACCCTATTTTGTGTTATAAAAATTGGGAGGTTAA 6640 sspl, IleAlaArgTyrIleArgLeuHisProThrHisTyrSerIleArgSerThrLeuArgMet
6661        ATTGCTCGATACATCCGTTTGCACCCAACTCATTATAGCATTCGCAGCACTCTTCGCATG
            TAACGAGCTATGTAGGCAAACGTGGGTTGAGTAATATCGTAAGCGTCGTGAGAAGCGTAC GluLeuMetGlyCysAspLeuAsnSerCysSerMetProLeuGlyMetGluSerLysAla
6721        GAGTTGATGGGCTGTGATTTAAATAGTTGCAGCATGCCATTGGGAATGGAGAGTAAAGCA
            CTCAACTACCCGACACTAAATTTATCAACGTCGTACGGTAACCCTTACCTCTCATTTCGT 6738 aha111, 6752 sph1, IleSerAspAlaGlnIleThrAlaSerSerTyrPheThrAsnMetPheAlaThrTrpSer
6781        ATATCAGATGCACAGATTACTGCTTCATCCTACTTTACCAATATGTTTGCCACCTGGTCT
            TATAGTCTACGTGTCTAATGACGAAGTAGGATGAAATGGTTATACAAACGGTGGACCAGA ProSerLysAlaArgLeuHisLeuGlnGlyArgSerAsnAlaTrpArgProGlnValAsn
6841        CCTTCAAAAGCTCGACTTCACCTCCAAGGGAGGAGTAATGCCTGGAGACCTCAGGTGAAT
            GGAAGTTTTCGAGCTGAAGTGGAGGTTCCCTCCTCATTACGGACCTCTGGAGTCCACTTA 6889 mstII, AsnProLysGluTrpLeuGlnValAspPheGlnLysThrMetLysValThrGlyValThr
6901        AATCCAAAAGAGTGGCTGCAAGTGGACTTCCAGAAGACAATGAAAGTCACAGGAGTAACT
            TTAGGTTTTCTCACCGACGTTCACCTGAAGGTCTTCTGTTACTTTCAGTGTCCTCATTGA 6904 bstXI, ThrGlnGlyValLysSerLeuLeuThrSerMetTyrValLysGluPheLeuIleSerSer
6961        ACTCAGGGAGTAAAATCTCTGCTTACCAGCATGTATGTGAAGGAGTTCCTCATCTCCAGC
            TGAGTCCCTCATTTTAGAGACGAATGGTCGTACATACACTTCCTCAAGGAGTAGAGGTCG 6999 xmn1, SerGlnAspGlyHisGlnTrpThrLeuPhePheGlnAsnGlyLysValLysValPheGln
7021        AGTCAAGATGGCCATCAGTGGACTCTCTTTTTTCAGAATGGCAAAGTAAAGGTTTTTCAG
            TCAGTTCTACCGGTAGTCACCTGAGAGAAAAAAGTCTTACCGTTTCATTTCCAAAAAGTC 7029 bal1, GlyAsnGlnAspSerPheThrProValValAsnSerLeuAspProProLeuLeuThrArg
7081        GGAAATCAAGACTCCTTCACACCTGTGGTGAACTCTCTAGACCCACCGTTACTGACTCGC
            CCTTTAGTTCTGAGGAAGTGTGGACACCACTTGAGAGATCTGGGTGGCAATGACTGAGCG 7116 xba1, TyrLeuArgIleHisProGlnSerTrpValHisGlnIleAlaLeuArgMetGluValLeu
7141        TACCTTCGAATTCACCCCCAGAGTTGGGTGCACCAGATTGCCCTGAGGATGGAGGTTCTG
            ATGGAAGCTTAAGTGGGGGTCTCAACCCACGTGGTCTAACGGGACTCCTACCTCCAAGAC 7148 ecor1, 7182 mstII, GlyCysGluAlaGlnAspLeuTyrOP
7201        GGCTGCGAGGCACAGGACCTCTACTGAGGGTGGCCACTGCAGCACCTGCCACTGCCGTCA
            CCGACGCTCCGTGTCCTGGAGATGACTCCCACCGGTGACGTCGTGGACGGTGACGGCAGT 7231 bal1, 7237 pst1, 7261        CCTCTCCCTCCTCAGCTCCAGGGCAGTGTCCCTCCCTGGCTTGCCTTCTACCTTTGTGCT
            GGAGAGGGAGGAGTCGAGGTCCCGTCACAGGGAGGGACCGAACGGAAGATGGAAACACGA 7321        AAATCCTAGCAGACACTGCCTTGAAGCCTCCTGAATTAACTATCATCAGTCCTGCATTTC
            TTTAGGATCGTCTGTGACGGAACTTCGGAGGACTTAATTGATAGTAGTCAGGACGTAAAG 7381        TTTGGTGGGGGGCCAGGAGGGTGCATCCAATTTAACTTAACTCTTACCTATTTTCTGCAG
            AAACCACCCCCGGTCCTCCCACGTAGGTTAAATTGAATTGAGAATGGATAAAAGACGTC 7435 pst1, 7438 pvu11,
```

FIG. II

```
7441  CTGCTCCCAGATTACTCCTTCCTTCCAATATAACTAGGCAAAAAGAAGTGAGGAGAAACC
      GACGAGGGTCTAATGAGGAAGGAAGGTTATATTGATCCGTTTTTCTTCACTCCTCTTTGG

7501  TGCATGAAAGCATTCTTCCCTGAAAAGTTAGGCCTCTCAGAGTCACCACTTCCTCTGTTG
      ACGTACTTTCGTAAGAAGGGACTTTTCAATCCGGAGAGTCTCAGTGGTGAAGGAGACAAC
```
7506 xmn1, 7530 stu1,
```
7561  TAGAAAAACTATGTGATGAAACTTTGAAAAAGATATTTATGATGTTAACATTTCAGGTTA
      ATCTTTTTGATACACTACTTTGAAACTTTTTCTATAAATACTACAATTGTAAAGTCCAAT
```
7604 hpa1,
```
7621  AGCCTCATACGTTTAAAATAAAACTCTCAGTTGTTTATTATCCTGATCAAGCATGGAACA
      TCGGAGTATGCAAATTTTATTTTGAGAGTCAACAAATAATAGGACTAGTTCGTACCTTGT
```
7632 aha111, 7664 bcl1,
```
7681  AAGCATGTTTCAGGATCAGATCAATACAATCTTGGAGTCAAAAGGCAAATCATTTGGACA
      TTCGTACAAAGTCCTAGTCTAGTTATGTTAGAACCTCAGTTTTCCGTTTAGTAAACCTGT 7741  ATCTGCAAAATGGAGAGAATACAATAACTACTACAGTAAAGTCTGTTTCTGCTTCCTTAC
      TAGACGTTTTACCTCTCTTATGTTATTGATGATGTCATTTCAGACAAAGACGAAGGAATG 7801  ACATAGATATAATTATGTTATTTAGTCATTATGAGGGGCACATTCTTATCTCCAAAACTA
      TGTATCTATATTAATACAATAAATCAGTAATACTCCCGTGTAAGAATAGAGGTTTTGAT 7861  GCATTCTTAAACTGAGAATTATAGATGGGGTTCAAGAATCCCTAAGTCCCCTGAAATTAT
      CGTAAGAATTTGACTCTTAATATCTACCCCAAGTTCTTAGGGATTCAGGGGACTTTAATA 7921  ATAAGGCATTCTGTATAAATGCAAATGTGCATTTTTCTGACGAGTGTCCATAGATATAAA
      TATTCCGTAAGACATATTTACGTTTACACGTAAAAAGACTGCTCACAGGTATCTATATTT 7981  GCCATTTGGTCTTAATTCTGACCAATAAAAAAATAAGTCAGGAGGATGCAATTGTTGAAA
      CGGTAAACCAGAATTAAGACTGGTTATTTTTTATTCAGTCCTCCTACGTTAACAACTTT
```
8039 hind111,
```
8041  GCTTTGAAATAAAATAACAATGTCTTCTTGAAATTTGTGATGGCCAAGAAAGAAAATGAT
      CGAAACTTTATTTTATTGTTACAGAAGAACTTTAAACACTACCGGTTCTTTCTTTTACTA
```
8081 ba11,
```
8101  GATGACATTAGGCTTCTAAAGGACATACATTTAATATTTCTGTGGAAATATGAGGAAAAT
      CTACTGTAATCCGAAGATTTCCTGTATGTAAATTATAAAGACACCTTTATACTCCTTTTA
```
8133 ssp1,
```
8161  CCATGGTTATCTGAGATAGGAGATACAAACTTTGTAATTCTAATAATGCACTCAGTTTAC
      GGTACCAATAGACTCTATCCTCTATGTTTGAAACATTAAGATTATTACGTGAGTCAAATG
```
8161 nco1,
```
8221  TCTCTCCCTCTACTAATTTCCTGCTGAAAATAACACAACAAAAATGTAACAGGGGAAATT
      AGAGAGGGAGATGATTAAAGGACGACTTTTATTGTGTTGTTTTACATTGTCCCCTTTAA 8281  ATATACCGTGACTGAAAACTAGAGTCCTACTTACATAGTTGAAATATCAAGGAGGTCAGA
      TATATGGCACTGACTTTTGATCTCAGGATGAATGTATCAACTTTATAGTTCCTCCAGTCT 8341  AGAAAATTGGACTGGTGAAAACAGAAAAAACACTCCAGTCTGCCATATCACCACACAATA
      TCTTTTAACCTGACCACTTTTGTCTTTTTGTGAGGTCAGACGGTATAGTGGTGTGTTAT 8401  GGATCCCCCTTCTTGCCCTCCACCCCCATAAGATTGTGAAGGGTTTACTGCTCCTTCCAT
      CCTAGGGGGAAGAACGGGAGGTGGGGGTATTCTAACACTTCCCAAATGACGAGGAAGGTA
```
8401 bamh1,

FIG.IJ

```
8461  CTGCCTGACCCCTTCACTATGACTACACAGAATCTCCTGATAGTAAAGGGGGCTGGAGGC
      GACGGACTGGGGAAGTGATACTGATGTGTCTTAGAGGACTATCATTTCCCCCGACCTCCG

8521  AAGGATAAGTTATAGAGCAGTTGGAGGAAGCATCCAAAGATTGCAACCCAGGGCAAATGG
      TTCCTATTCAATATCTCGTCAACCTCCTTCGTAGGTTTCTAACGTTGGGTCCCGTTTACC

8581  AAAACAGGAGATCCTAATATGAAAGAAAAATGGATCCCAATCTGAGAAAAGGCAAAAGAA
      TTTTGTCCTCTAGGATTATACTTTCTTTTTACCTAGGGTTAGACTCTTTTCCGTTTTCTT 8612 bamh1, 8641  TGGCTACTTTTTTCTATGCTGGAGTATTTTCTAATAATCCTGCTTGACCCTTATCTGACC
      ACCGATGAAAAAGATACGACCTCATAAAAGATTATTAGGACGAACTGGGAATAGACTGG 8701  TCTTTGGAAACTATAACATAGCTGTCACAGTATAGTCACAATCCACAAATGATGCAGGTG
      AGAAACCTTTGATATTGTATCGACAGTGTCATATCAGTGTTAGGTGTTTACTACGTCCAC 8722 tthIII1, 8761  CAAATGGTTTATAGCCCTGTGAAGTTCTTAAAGTTTAGAGGCTAACTTACAGAAATGAAT
      GTTTACCAAATATCGGGACACTTCAAGAATTTCAAATCTCCGATTGAATGTCTTTACTTA 8821  AAGTTGTTTTGTTTTATAGCCCGGTAGAGGAGTTAACCCCAAAGGTGATATGGTTTTATT
      TTCAACAAAACAAAATATCGGGCCATCTCCTCAATTGGGGTTTCCACTATACCAAAATAA 8852 hpa1, 8881  TCCTGTTATGTTTAACTTGATAATCTTATTTTGGCATTCTTTTCCCATTGACTATATACA
      AGGACAATACAAATTGAACTATTAGAATAAAACCGTAAGAAAAGGGTAACTGATATATGT 8941  TCTCTATTTCTCAAATGTTCATGGAACTAGCTCTTTTATTTTCCTGCTGGTTTCTTCAGT
      AGAGATAAAGAGTTTACAAGTACCTTGATCGAGAAAATAAAAGGACGACCAAAGAAGTCA 9001  AATGAGTTAAATAAAACATTGACACATACAAAAAAAAAAAAAAAAAAAAAAAAAAAAAAA
      TTACTCAATTTATTTTGTAACTGTGTATGTTTTTTTTTTTTTTTTTTTTTTTTTTTTTTT

9061  A
      T
```

FACTOR VIII:C CDNA CLONING AND EXPRESSION

CROSS-REFERENCE TO RELATED APPLICATIONS

The present application is a continuation of application Ser. No. 06/757,095, filed July 19, 1985, now abandoned, which is a continuation-in-part of application Ser. No. 06/689,274, filed Jan. 7, 1985, now U.S. Pat. No. 4,716,117, which is a continuation-in-part application Ser. No. 06/664,919, filed Oct. 26, 1984, now abandoned, which is a continuation-in-part of application Ser. No. 06/570,062, filed Jan. 12, 1984, now U.S. Pat. No. 5,004,804.

BACKGROUND OF THE INVENTION

1. Field of the Invention

Factor VIIIC is a plasma protein that participates in the intrinsic pathway of blood coagulation It is absent or defective in individuals with the hereditary X chromosome-linked recessive bleeding disorder hemophilia A. Great difficulty has been encountered in isolating Factor VIIIC due to its extremely low concentration in plasma and the fact that it appears to be an intermediate or final degradation product of a larger protein precursor. Therefore, efforts to isolate Factor VIIIC have led to complex mixtures of significant heterogeneity and varying molecular weights.

One of the approaches which has found broad application to the production of physiologically active proteins involves the isolation of the protein of interest in purified form. The protein of interest provides invaluable aid in the development of a recombinant DNA capability for the production of the protein. By having the protein of interest, one may prepare monoclonal antibodies which are specific for the protein and can be used to establish the production of the protein in lysates, expression from messenger RNA in oocytes, or from a cDNA gene in unicellular microorganisms. In addition, by amino acid sequencing, one can develop probes, employing codons coding for the particular amino acid sequence, for hybridization to messenger RNA, chromosomal DNA or cDNA and, therefore, provide for the detection, isolation and expression of the relevant gene or message and the production of the desired product in high yield in one or more hosts.

2. Description of Relevant Literature

U.S. Pat. No. 4,361,509 and references cited therein describe purification of Factor VIIIC. See also Fulcher and Zimmerman, *Proc. Natl. Acad. Sci. USA* (1982) 79:1648–1652. Tuddenham et al., *J. of Lab. Clinical Medicine* (1979) 93:40–53 describes purification of Factor VIIIC using polyclonal antibodies. Austen, *British J. Hematology* (1979) 43:669–674 describes the use of aminohexyl-Sepharose for Factor VIIIC purification. Weinstein et al., *Proc. Natl. Acad. Sci. USA* (1981) 78:5137–5141 describes a study of the effect of thrombin on Factor VIIIC. See also Kuo et al., Abstracts for IX International Congress of Thrombosis and Hemostasis, (Copenhagen; July, 1983).

SUMMARY OF THE INVENTION

Methods and compositions are provided for the preparation of human Factor VIIIC, precursors and subunits thereof, by production in an expression system, such as a microorganism or mammalian tissue culture. The method involves isolating pure Factor VIIIC, subunits and fragments thereof and determining their physiological relationship, particularly employing thrombin digestion. At least a portion of each of the related series of polypeptides is sequenced and the sequences employed for developing complex probes. Genomic DNA fragments are probed for homologous sequences and hybridizing fragments isolated and further manipulated to provide a DNA fragment encoding a complete subunit or fragment, essentially free from structural genes present in the normal human chromosome. This fragment may be used for isolating mature mRNA, from which cDNA may be obtained. The DNA sequence may then be further manipulated for insertion into an expression vector and the expression vector employed for introduction into a compatible host for expression of the polypeptide.

BRIEF DESCRIPTION OF THE FIGURES

FIG. 1 provides the nucleotide sequence and putative corresponding amino acid sequence of a full-length cDNA clone exhibiting human Factor VIIIC activity.

DESCRIPTION OF THE SPECIFIC EMBODIMENTS

Figure 2:
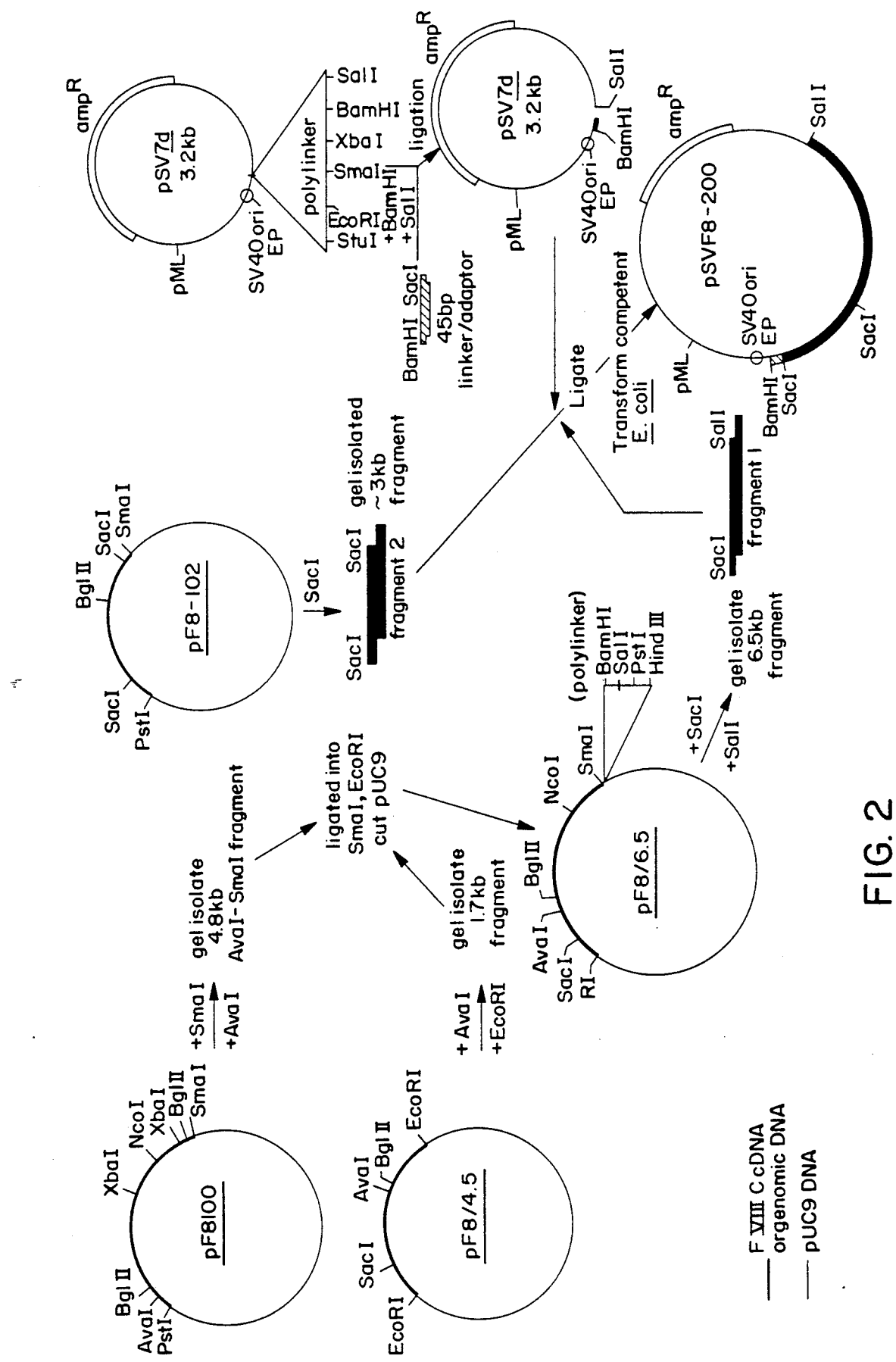
FIG. 2 illustrates the construction of the full-length cDNA encoding human Factor VIIIC in a mammalian expression vector.

Human Factor VIIIC fragments and subunits are provided in substantially pure form. In addition, methods and compositions are provided for the expression of Factor VIIIC subunits and fragments for producing Factor VIIIC as a precursor or in its active form or providing individual subunits for use in combination with naturally available subunits. The subunits and fragments have one or more biological properties associated with Factor VIIIC, such as epitopic sites, coagulation activity, and immunogenicity, so as to be used for producing antibodies which find use as reagents, particularly labeled reagents in immunoassays.

Human Factor VIIIC is a complex protein which can be isolated in substantially pure form exhibiting an apparent molecular weight of about 460 kd on SDS polyacrylamide gel electrophoresis. Upon electrophoresis under denaturing conditions, a large number of fragments result of varying molecular weights: 240, 160, 140, 115, 92.5, 80 and 77 kd, the latter two being found to migrate as a doublet. Analysis of the fragments by chemical and protease cleavage (including thrombin) and by employing antibodies to follow immunogenic relationships and cleavage patterns to follow structural relationships, demonstrates that the 92.5 kd polypeptide is related to the 240, 160, 140 and 115 polypeptides and from the N-terminal region of the non-reduced protein, while the 77/80 doublet is from the C-Terminal end of the protein. It is further found that the 77/80 kd doublet is converted by thrombin to a 67/70 kd doublet, while the 92.5 kd polypeptide is cleaved by thrombin, directly or indirectly, into two polypeptides of about 40 and 52.5 kd (which can be further cleaved as well). It is found that the electrophoretically isolated 77/80 kd doublet polypeptides have their N-termini blocked, while the 67/70 kd doublet polypeptides do not.

It is further found that the locus for Factor VIIIC involves exons with large introns, where exons involve various domains associated with Factor VIIIC. Thus, individual exons can be isolated which make up specific subunits, or portions thereof, of the Factor VIIIC complex. By identifying specific amino acid sequences involved with Factor VIIIC subunits and portions thereof, one can selectively isolate the exons from genomic DNA and use the exons by themselves, in combination, or joined by synthetic DNA pieces to provide for sequences encoding for polypeptide subunits of Factor VIIIC or fragments thereof.

Conveniently, the Factor VIIIC genomic DNA sequences containing both exons and introns may be inserted into an expression vector appropriate for transcription and translation in mammalian cells to provide for both substantial quantities of properly spliced messenger RNA suitable for cDNA cloning and production of Factor VIIIC subunits or fragments. In addition, the DNA sequences isolated from the genome can be used for hybridizing to natural messenger RNA (mRNA) encoding for Factor VIIIC. The mRNA may then be used to prepare cDNA encoding Factor VIIIC. The cDNA sequences commonly less than about 10 kb, preferably less than about 7 kb, may be employed for expression by insertion into an appropriate expression vector having the necessary regulatory signals for transcription and translation. The Factor VIIIC gene expression vector (an expression vector carrying one or more genes encoding for all or a portion of Factor VIIIC, precursor, subunits or fragments thereof) may be introduced into a compatible host and the host grown for expression of Factor VIIIC. By appropriate choice of hosts, the Factor VIIIC DNA may be inserted downstream from secretory leader and processing signals, so that the product will be secreted from the host and processed to provide for the complete polypeptide. As appropriate, the polypeptide may be further processed to introduce functionalities or substituents present on the naturally occurring polypeptide.

In the first stage of the subject invention, highly purified Factor VIIIC is obtained and characterized. Purified Factor VIIIC can be obtained from commercially available human anti-hemophilic factor (AHF), which is prepared from fresh, normal human plasma as a cryoprecipitate and represents about a 40-fold enrichment. The Factor VIIIC is further concentrated and purified by dissolving the anti-hemophilic factor into an appropriate buffer, e.g., saline imidazole-lysine-HCl, pH 7.4, followed by chromatography on an affinity column having either polyclonal or monoclonal antibodies to Factor VIIIC or Factor VIIIR. Conveniently, the antibodies are covalently bonded to a Sepharose support. Factor VIIIC may be eluted from the column employing a combination of a relatively high concentration of calcium ion in combination with glycerol. The fractions obtained from the column may then be dialysed with an appropriate buffer, as described above, containing a low concentration of calcium ion and may then be further purified employing an aminohexyl-Sepharose column eluted with a high calcium or sodium chloride concentration buffer. Additional chromatographic steps, e.g., gelatin Sepharose, HPLC, ion exchange on dextran sulfate or Mono Q, affinity columns using lectins or antibodies to Factor VIIIC, provide additional purification. Particularly, the use of dextran sulfate removes trace contamination, e.g., fibrinogen, fibronectin, IgG, from the preparation, so as to leave a product substantially free of foreign proteins. Activity of the fractions from the columns may be monitored for either or both biological and antigenic activity using coagulation assay (commercially available kits) and antibodies specific for Factor VIIIC. Based on the concentration of Factor VIII in plasma, purifications of about 200,000-fold may be achieved by the above-described method.

Characterization of Factor VIIIC

Gel filtration indicates that Factor VIIIC behaves as a complex with an apparent molecular weight of about 460 kd. Using SDS-gel electrophoresis (denaturing conditions) seven individual polypeptides can be isolated of differing molecular weight. The fragments as defined by their molecular weight are 240, 160, 140, 115, 92.5, 80 and 77 kd. These fragments were characterized in the following ways.

The first study involved employing inhibitor antibodies isolated from hemophilic patients, the antibodies being designated as Z and E. Both antibodies reacted with the 77/80 kd doublet. The E antibody reacted strongly with the 240 kd polypeptide and weakly with several bands between the doublet and the 240 kd polypeptide. The Z antibody also reacted weakly with the 240 kd polypeptide.

In immunoprecipitation experiments, the E antibody precipitates the 77/80 kd doublet as well as the high molecular weight species of 160, 140, 115 and 92.5 kd, with the doublet among the stronger bands. Inclusion of EGTA results in the loss of the bands other than the doublet indicating that the 92.5 kd species is associated with the 77 kd and/or 80 kd species in a complex mediated by a $Ca^{++}$ bridge.

In the next study, monoclonal antibodies were prepared, which both inhibit Factor VIIIC mediated coagulation activity and react with components of the complex: Class I reacting with the 77/80 kd doublet and 240 kd polypeptides; Class III reacting with the 160, 140, 115 and 92.5 kd polypeptides. Immunoprecipitation of thrombin-digested Factor VIIIC with Class I antibodies indicates that the resulting 70/67 kd doublet is derived from the 77/80 kd doublet present in Factor VIIIC. The Class III monoclonals indicated that the 160, 140 and 115 kd peptides are precursors of the 92.5 kd peptide. A 40 kd peptide cleavage product of 92.5 kd peptide was also bound by the Class III antibodies. An ELISA assay using monoclonal antibodies in the presence and absence of EGTA confirms the $Ca^{++}$ bridge association between the 92.5 kd and 77 kd and/or 80 kd components of the Factor VIIIC complex.

Both the human inhibitor and monoclonal antibodies may be used in immunosorbent column procedures to obtain Factor VIIIC or using EGTA, to resolve its constituent components, the 92.5 kd and 77/80 kd species.

The next study involved thrombin degradation of purified Factor VIIIC material at pH 6.8 or 7.4. Aliquots were assayed for coagulation activity and TCA precipitated for gel analysis. Coagulation activity was shown to increase with time and then decrease coincidently with an increase and decrease in the amount of the 92.5 kd species. Thrombin treatment of the purified Factor VIIIC material for short periods of time (5–15 min) enhances the amount of 92.5 kd species, while the 77/80 kd doublet is partially converted to a 67/70 kd doublet. When long thrombin digestion times are employed, e.g., one hour, the 92.5 kd protein is degraded and two new peptides of 40 and 52.5 kd appear, with the 40 kd peptide retaining immunogenic characteristics of the 92.5 kd species. The 52.5 kd peptide is shown to be a cleavage product by chemical and enzymatic degradation patterns and products analogous to the 92.5 kd species.

In the next study individual Factor VIIIC subunits and precursors (e.g., 240, 77/80, 92.5 kd species) were isolated by preparative SDS gel electrophoresis and a time course thrombin digestion of the isolated polypeptides was then performed. The 240 kd fragment isolated from a preparative gel produced 160, 140, 115, and 92.5 kd bands. The 80 kd and 77 kd fragments produced a 70 kd and 67 kd fragment, respectively.

A Factor VIIIC complex is derived containing the 77 kd and/or 80 kd species and 92.5 kd polypeptide as a calcium-bridged complex in highly purified form. The purity of Factor VIIIC material (the complex and precursor species) is usually greater than 80%, often greater than 90%, and may be 98% or higher based on total protein, and that of the complex at least 20%, more usually 30% based on total protein, following the anti-Factor VIIIR immunosorbent and aminohexyl Sepharose columns. The use of additional chromatographic steps, e.g., dextran sulfate, increases the level of purity to at least 90% and usually greater for the Factor VIIIC material (complex plus precursor). The purity of Factor VIIIC components, 92.5 kd species and the 77/80 kd doublet, isolated by preparative SDS gel electrophoresis is usually at least 98%. As indicated above, the complex can be obtained using monoclonal antibodies specific for a member of the doublet, or for the 92.5 kd polypeptide. The complex may then be separated from the antibody using a denaturing or chaiotropic solvent, e.g., aqueous urea or thiocyanate, respectively.

Preparation of Probes

A partial amino acid sequence of the N-terminus of the 67 and 70 kd polypeptides is as follows:

```
 1   2   3   4   5   6   7   8   9  10  11
 ?  Phe Gln Lys Lys Thr Arg His Tys Phe Ile 12  13  14  15  16  17  18  19  20  21  22
Ala Ala Val Glu Arg Leu Trp Asp Tyr Gly Met
```

Based on this sequence, probes for the 67/70 kd doublet (and thus the 77/80 kd doublet from which it is derived) may be prepared having the following sequences:

```
Probe 1:  3' GTA ATA AAA YAA CGX CGX CA 5'   (X = G.C.A.T)
(non-coding)    G   G   G
                            T Probe 2:  3' AAA GTT TTC TTC TGX T CT GT 5'
(non-coding)    G   C   T   T       C
                                  GCX Probe 3:  5' GAA CGX TTA TGG GAT TAT GGX ATG 3'
(coding)        G AGA   G               C   C
                G CTX Probe 4:  3' TCT GTA ATG AAA TAG CGA CGA CAC CTT TCT GAC ACC CTA ATG CCG TAC 5'
(non-coding)    C   G       G       G   G       C   C               G
```

The N-terminus amino acid sequence of the 52.5 kd protein is substantially as follows:

```
 1   2   3   4   5   6   7   8   9  10  11  12  13
Ala Thr Arg Arg Tyr Tyr Leu Gly Ala Val Glu Leu Ser 14  15  16  17  18  19  20  21  22  23  24  25  26
Trp Asp Tyr Met Gln Ser Asp  ?  Gly Glu Leu Pro Val
```

Based on this amino acid sequence, a probe for the 52.5 kd protein may be prepared based on the coding strand as follows:

```
5'-GCA ACT AGA AGA TAT TAT TTG GGG GCA GTT GAA TTG TCA TGG GAT TAT-3'
        A   G   G           A   A   A           A   T
```

The amino acid sequences of three fragments of the 77/80 kd proteins are as follows:

```
 1   2   3   4   5   6   7   8   9  10  11  12
Tyr Ala Ala Thr Ser Gln Val Leu Leu Pro Ser Lys 1   2   3   4   5   6   7   8   9  10
Val Thr Gly Val Thr Thr Gln Gly Val Lys 1   2   3   4   5   6   7   8   9  10  11  12
Met Glu Val Leu Gly Cys Glu Ala Gln Asp Leu Tyr
```

Based on these sequences respectively, probes may be prepared based on the non-coding strands as follows:

```
Probe 1:  3'-ATA CGT CGT TGA AGT GTT CAA AAC AAC GG-5'
                 T       A       T   T   T Probe 2:  3'-CAA TGA CCT CAA TGA TGA GTT CCT CAA TTT-5'
                 T   T       T   T   T           T Probe 3:  3'-TAC CTT CAA AAC CCT ACG CTT CGT GTT CTA AAC ATA-5'
                 T   T                                   T
```

Sequences of these peptides and preparation of the corresponding probes are described in detail in the Experimental section hereinafter.

Isolation of DNA

The above probes can be used for the detection and isolation of either genomic DNA or messenger RNA. Cloning genomic DNA involves cleavage of the genomic DNA with one or more restriction enzymes to obtain a partial digest and size selection of fragments of about 10–25 kb. The restriction digests should be incomplete so that there will be overlapping fragments cloned. These fragments may be cloned in the appropriate vector to produce a "library" of clones in microorganisms, e.g., bacteria, such as E. coli. Various vectors may be employed, including plasmids or viruses, such as pBR322, lambda, charon 4A, EMBL-4, or the like.

The DNA is screened with the enzymatically radiolabeled probes described above and homologous sequences detected. Those sequences which hybridize with one or more of the probes may be recloned and again rehybridized one or more times.

One or more restriction enzymes different from the original restriction enzyme(s) employed may then be used to provide for smaller fragments, generally ranging from about 1-10 kb, more usually from about 1-6 kb. These fragments may then be subcloned and screened to identify positive fragments. The synthetic probes can then be used as primers for sequencing of the DNA fragments. Fragments which may be most conveniently sequenced are those which include a sequence complementary to one or more of the above-identified probes, where the homologous sequence is from about 5 bases and up to not more than about 500 bases from the 5'-terminus. Other fragments of interest include those at the termini of the original cloned fragment since these will be represented in other clones in the library and thus used to "walk" along the chromosome until the entire desired gene is recovered.

After sequencing the DNA fragment, based on the determined sequence, the fragment will be further manipulated. Based on the sequence, one can identify an open reading frame including the determined amino acid sequence. By determining restriction sites, one can further reduce the size of the fragment, without loss of coding sequences, although removal of a short sequence at the N-terminus is permissible, since this can be replaced by using appropriate adapters. Where restriction sites are not readily available at appropriate positions, the DNA fragment may be modified by Bal31 resection for varying times, the resulting fragments cloned, and the 5'-termini determined by various techniques. Conveniently, one can provide for a recognition site of a particular restriction enzyme by appropriate selection of the 3'-bases to which the resected fragment is joined. In this way, one can screen the resulting clones for the predetermined restriction site, which will indicate the presence of a fragment resected to the desired site.

Desirably exons or fragments thereof, usually of at least 50 bp, more usually of at least about 100 bp, even about 250 bp or more, may be denatured and used as probes for mRNA from human cells, particularly cells producing mRNA for Factor VIIIC. By isolating hybridizing mRNA, the mRNA may be screened by translation in oocytes or a reticulocyte lysate and production of Factor VIIIC detected by antibodies to Factor VIIIC or coagulation activity based on binding to Factor VIIIC subunits. The mRNA may then be reverse transcribed, using, for example, AMV reverse transcriptase. Various methods can be used for converting ss cDNA to ds cDNA, using the reverse transcriptase or DNA polymerase I (Klenow fragment) to produce the second strand, followed by removal of the terminal loop, as appropriate, with a nuclease, e.g., $S_1$ nuclease. Where an incomplete copy is obtained, the messenger may be "walked" or primed cDNA synthesis may be used until the 5'-coding sequence of the mRNA has been copied and a DNA sequence encoding for the entire coding region of the mRNA is obtained.

Based on the above procedures, DNA sequences coding for the polypeptide precursor(s) to Factor VIIIC or major fragments thereof may be used for expression, or smaller fragments coding for specific subunits of Factor VIIIC, e.g., 92.5 kd, 80 kd or 77 kd, may be employed.

For the precursor polypeptide, (proFactor VIIIC), the gene may be blunt-ended at one or both ends and inserted into an expression vector having complementary ends, or may be cleaved downstream from the 5'-coding terminus and joined to an adapter for appropriate insertion into the vector.

Fragments having the proper N-terminus, which may be at the coding sequence for the 70 kd or 80 kd polypeptide or may have a 5'-terminus downstream from the initial base, usually not more than about 30 bases downstream, more usually not more than about 20 bases downstream, may then be inserted into an appropriate vector using adapters, as appropriate.

Various vectors may be employed for providing extrachromosomal elements, depending upon the particular host, the manner of expression, whether constitutive or induced, the desired markers, whether secretion is desired, or the like. (By vector is intended an intact replication system.) Numerous vectors are presently available which provide for the transcriptional and translational regulatory signals recognized either by mammalian hosts, e.g., tissue culture cells or by prokaryotic and eukaryotic microorganism hosts, e.g., *E. coli, B. subtilis, B. thermophilus, S. cerevisiae*, or the like.

The vectors will have a replication system recognized by the host, although in some instances, integration of a construct having transcriptional and translational regulatory signals and the cistron of interest into the host genome may be desirable. In those situations, the construct will usually be flanked by sequences homologous to sequences in the host genome.

The expression vectors which are employed will have transcriptional and translational signals recognized by the host. The transcriptional signals will include the promoter and terminator, as well as auxiliary signals such as one or more enhancers. In addition, regulation of transcription may be provided, by including operators, activators, genes providing for repression, or the like. Other sequences involved with transcription include capping, polyadenylation, etc. For translation, depending upon the host, there may be a ribosomal binding site, an initiation codon, stop codons, or the like.

Conveniently, non-coding 5'- and 3'-flanking regions will be employed from genes native to the host, so that the signals recognized by the host will be present in appropriate relationship. These flanking regions can be joined to the gene encoding for the Factor VIIIC precursor, subunit or fragment thereof, so that the gene is in reading frame with the initiation codon and either carries its own stop codon or is inserted immediately upstream from one or more stop codons.

A vector will normally have one or more markers which provide for selection and allow for continued selective pressure during growth of the host. These markers may include prototrophy in an auxotrophic host, antibiotic resistance, toxin resistance, etc.

Where a secretory leader and processing signals are provided, it will usually be necessary to provide an adapter. By providing for an appropriate restriction site at the terminus of the DNA sequence encoding secretory leader and processing signals or upstream therefrom, one can synthesize an oligonucleotide adapter, usually of from about 10-50 bp, which can be inserted between the secretory leader and processing signals or truncated portion thereof, and the gene of interest.

which has a 5'-terminus at the initial codon of the gene or downstream thereof, so that the adapter restores all of the necessary missing bases and provides for the gene being in reading frame with the initiation codon of the leader sequence.

The resulting constructs which include the desired gene may then be introduced into a host, capable of growth in culture, in accordance with conventional methods, e.g., transformation, conjugation, transfection, or the like. The host may then be grown in an appropriate nutrient medium and the product isolated in accordance with conventional ways. Where the product is retained intracellularly, the cells will be harvested and lysed; where secreted, the product will be isolated from the nutrient medium. The product may be purified by chromatography, e.g., affinity chromatography, electrophoresis, extraction, HPLC, or the like.

For expression in a mammalian cell a mammalian virus may be employed as the vector, e.g., SV-40, papilloma virus, Maloney murine sarcoma virus, adenovirus, or the like. These viruses have been modified for use as expression vectors in mammalian cell cultures. An illustrative system employs COS cells bearing an integrated SV-40 genome and producing the large T antigen required for SV-40 replication (Gluzman, *Cell* (1981) 23:175). A fragment spanning the HpaI site at 0.76 on the SV-40 map to the BamHI site at 0.14 on the SV-40 map may be used as a vector. The recombinant plasmid obtained by joining the Factor VIIIC gene or portion thereof with the SV-40 vector may be used to transfect monkey CV-1 cells.

In accordance with the subject invention, purified subunits and fragments of Factor VIIIC may be obtained and used to enhance clotting capability for individuals requiring the particular subunit. The Factor VIIIC may also be used in therapy. In addition, the polypeptides prepared according to this invention can be used for the production of monoclonal antibodies to Factor VIIIC, its subunits and fragments. Also, the subunits and fragments may be used as reagents, which may be labeled and in combination with the antibodies, employed in diagnostic assays for the presence of one or more subunits or degradation fragments thereof in physiological fluids, e.g., blood or serum.

The following examples are offered by way of illustration and not by way of limitation.

Whenever used hereinafter Ab intends antibody and Ag antigen.

EXPERIMENTAL

I. Purification of Factor VIIIC

Human Factor VIIIC was isolated from commercial cryoprecipitate preparations by a) immunosorbent chromatography using a polyclonal anti VIIIR-Sepharose column by a method first described by E. G. D. Tuddenham, N. C. Trabold, J. A. Collins, and L. W. Hoyer, *J. of Lab. Clinical Medicine* (1979) 93:40; and b) a chromatographic separation on aminohexyl-substituted agarose as was originally described by D. E. G. Austen, *British J. of Hematology* (1979) 43:669.

Details of the procedures are described below.

Goat anti-human Factor VIII Related Antigen (VIII:R) serum obtained from *Atlantic Antibody* (cat. no. 040-01), was treated with either a standard 0-50% ammonium sulfate cut followed by DEAE cellulose column chromatography, or a similar 0-33% cut without subsequent chromatography. These materials were then conjugated to CNBr-activated Sepharose CL2B or 4B, respectively, (Pharmacia, 17-0140-01 or 17-0430-01) and poured as a column (anti VIII:R-Sepharose column).

"HEMOFIL", a stable, dried preparation of antihemophilic factor (Factor VIII, AHF, AHG) in concentrated form prepared from fresh, normal human plasma, representing about a 40-fold enrichment for Factor VIIIC, was dissolved in the following buffer: 0.02M imidazole, 0.15M NaCl, 0.1M lysine-HCl, 0.02% $NaN_3$, pH 7.4.

After being dissolved, the Hemofil was applied to the above-described anti VIII:R-Sepharose column. Nonspecifically bound protein was eluted with the above buffer modified to 0.5M NaCl. Next, Factor VIIIC was eluted with the above buffer containing 0.35M $CaCl_2$, with the addition of 10% glycerol which stabilizes the Factor VIIIC activity. Active fractions from the immunosorbent column were pooled and dialyzed against buffer (0.02M imidazole, 0.15M NaCl, 0.1M lysine-HCl, 0.025M $CaCl_2$, 0.02% $NaN_3$, 10% glycerol, pH 7.4). An aliquot of the dialyzed fractions, which contained 1,100 units of Factor VIIIC, was applied to an aminohexyl-Sepharose 4B column (1×6 cm) equilibrated with dialysis buffer described above. Factor VIIIC activity was eluted with the same buffer containing either 0.35M $CaCl_2$ or 2M NaCl. The activity was found to be in a volume of 2 ml with 500 units of Factor VIIIC per ml. Subsequent experiments carried out in the same manner provided a recovery of 25% off the anti VIII:R column and a recovery of approximately 90% off the aminohexyl column. Alternatively, pooled, dialysed material eluted from the immunosorbent column is first applied to a dextran sulfate (Pharmacia) column (1.5×6 cm) equilibrated with the dialysis buffer above and eluted with the same buffer. Several minor contaminants, e.g., fibrinogen, fibronectin, IgG, are retained on the column while Factor VIIIC emerges in the flow-through which is collected and loaded on the aminohexyl-Sepharose column as before.

Both biological, i.e., clotting, and antigenic (cAg) activity were shown to be present in the purified Factor VIIIC, as demonstrated by the subsequent assays indicating a 5,000-fold purification over the 40-fold concentration in Hemofil. Using a standard commercially available three component kit from General Diagnostics, Inc. (APTT, Factor VIII deficient plasma, Verify Normal Citrate; Morris Plains, N.J.) a coagulation assay was carried out and indicated high levels of Factor VIIIC biological activity. (See generally, Hardisty, R., et al., "A One Stage Factor VIII Assay and Its Use on Venous and Capillary Plasma," *Thombosis et Diathesis Haemorrhagica* (1962) 7:215-299; and Owen, C., et al., *The Diagnosis of Bleeding Disorders*, 2d ed., Little, Brown & Co., Boston, 1974, both of which are incorporated herein by reference.)

Antibodies employed were derived from inhibitor patients, one with a low titer (LZ) as coating ab and one with a high titer (HZ) as the labeled ab. The antibodies were used in two different types of assays. In an RIA assay, the HZ ab is labeled with $I^{125}$, while in an ELISA assay the HZ ab is coupled to horseradish peroxidase. Labeling with $^{125}I$ of antibody HZ for the RIA was performed in accordance with Hunter, W. M., *In Radioimmunoassay*, Weir, D. M., ed., Handbook of Experimental Immunology, 3rd ed., vol. 1, Blackwell Scientific Publications, Oxford, 1978. HRP-HZ conjugation was in accordance with Wilson and Nakane, *In Immu-*

*nofluorescence and Related Staining Techniques*, Knapp et al., eds., Elsevier, North-Holland Biomedical Press, Amsterdam, 1978, pp. 215-224. LZ had an activity of 700 Bethesda Units/ml while HZ had an activity of 1,500 Bethesda Units/ml. Coating antibody (LZ) was diluted to 3.5 μg/ml in 0.1M NaHCO$_3$, pH 9.8 (RIA) or 0.05M imidazole, 0.1M NaCl, 0.01% Thimerosal, 0.05% Tween 20, 5% BSA (ELISA) or for either method PBS-CMF (for 1 liter: 200 mg KCl, 200 mg KH$_2$PO$_4$, 8.0 g NaCl, 1.15 g anhydrous Na$_2$HPO$_4$, pH 7.4) and 1 ml added to each tube (polystyrene) and incubated overnight at room temperature. This solution is removed by suction and the tubes washed 3× with 3-3.5 ml 0.15M NaCl or PBS-CMF containing 0.05% Tween 20. Samples or standards (General Diagnostics, Verify Normal Citrate, catalog #34112) are diluted and added to the tubes to a total volume of 0.9 ml per tube and incubated overnight at room temperature (dilutions were made in 0.02M Tris, 0.15M NaCl, 5% BSA, 0.05% Tween 20, 0.01% Thimerosal, pH 6.5 for RIA or 0.05M imidazole, 0.1M NaCl, 0.01% Thimerosal, 0.05% Tween 20, 5% BSA for ELISA or PBS-CMF for either method). Solutions were removed by suction and tubes washed as before. For RIA, 5×10$^5$ cpm of $^{125}$I-labeled antibody to Factor VIIIC (HZ) in 600 μl of RIA dilution buffer was added to each tube which was then incubated at 37° C. for 16-18 h; solutions were removed, the tubes washed as before and counted in a gamma counter. For ELISA, 0.9 ml peroxidase conjugated anti-Factor VIIIC (HZ) was added to each tube which was then incubated overnight at room temperature; solutions were removed and the tubes washed as before, then 0.9 ml OPD solution (for 100 ml: 0.73 g citric acid, 1.19 g disodium acid phosphate, 0.15 g o-phenylenediamine, pH 5.0 with 250 μl 10% H$_2$O$_2$ added immediately before use) added and incubated at room temperature for 30 min in the dark. To stop this reaction, 0.5 ml of 6N HCl (or 0.9 ml 1M H$_2$SO$_4$) was added to each tube and the OD$_{492}$ read.

II. Structure of the Factor VIIIC Complex

A. Immunoprecipitation Experiments

Gel filtration experiments were carried out with an AcA 44 column on the 1.actor VIIIC purified material under the following conditions: 0.1% insulin (as carrier protein for stabilization), 0.25M CaCl$_2$, 0.01% Thimerosal, 0.05M imidazole, pH 7.2. The Factor VIIIC coagulation and antigenic activities of the eluate were monitored. Two antigenic peaks were observed. One with Factor VIIIC coagulation activity behaved as a complex with an apparent molecular weight of about 460,000 under these conditions (native). The other peak (devoid of coagulation activity) eluted at an observed molecular weight slightly below 67,000.

When analyzed by standard analytical Laemmli SDS-gel electrophoresis (Laemmli, *Nature* (1970) 227:680-685), various protein species of 240, 160, 140, 115, 92.5, 80 and 77 kd were obtained. The relationship of these proteins to Factor VIIIC was determined by standard immunoprecipitation procedures. In the immunoprecipitation procedure, *S. aureus* protein A-Sepharose CL4B or polystyrene beads (⅛ in, Precision Plastic Ball Co.) coated with affinity purified second antibody (goat anti-mouse IgG or anti-human IgG) were employed to separate antigen-Ab complexes from free $^{125}$I-labeled Factor VIIIC.

The proteins eluted from the affinity column were iodinated and then reacted with antibodies specific for Factor VIIIC. The antibodies were human inhibitor antibodies isolated from hemophiliac patients and referred to as anti-Factor VIIIC (Z) and (E) or inhibitor antibody (Z) and (E).

The results indicated that both antibodies reacted with the 77/80 kd doublet. The "E" antibody also reacted strongly with the 240 kd band and gave weak precipitation of several bands (160, 140, 115, 92.5 kd) between the doublet and 240 kd species. The "Z" antibody also precipitated the 92.5 kd and 240 kd proteins. The strong reaction of the "E" antibody with the 240 kd species suggests that this species is a precursor of Factor VIIIC.

The antibody-column purified Factor VIIIC fraction was iodinated and reacted with the human inhibitor antibody in the presence and absence of EGTA (ethylene glycol bis(β-aminoethyl ether) N,N,N'.N'-tetracetic acid). This allows for an investigation of the role of divalent cations, particularly Ca$^{++}$, in the association of the Factor VIIIC polypeptides. It was observed that the inhibitor antibody (E) precipitates the 77/80 kd doublet, as well as higher molecular weight species of 160, 140, 115 and 92.5 kd. The doublet is always among the stronger bands. (This immunoprecipitation experiment was done with the polystyrene beads. This procedure results in lower backgrounds and the labeled IgG in the Factor VIIIC preparation is not precipitated). Inclusion of EGTA results in the loss of the higher molecular weight bands (92.5-160 kd) but has no effect on the amount of doublet precipitated. A similar experiment utilized Z antibody coupled to Sepharose as an immunosorbent: purified Factor VIIIC is applied to the column and after binding via 77/80 kd, the 92.5 kd polypeptide is selectively eluted with EDTA (ethylene diamine tetraacetic acid). The method is used preparatively to fractionate the 92.5 kd species. This immunosorbent column or a similar one are prepared with polyclonal antibodies to Factor VIIIC. When eluted with chaotropic or denaturing solvents, e.g., thiocyanate solutions or aqueous urea, respectively, rather than EGTA, Factor VIIIC is further purified. These results suggest that the 92.5 kd peptide may be associated noncovalently to the 77/80 kd doublet via a Ca$^{--}$ bridge. Inhibitor antibody appears to interact directly only with the doublet. The higher molecular weight bands (the 115 kd, 140 kd, 160 kd) are probably precursors of 92.5 kd, as indicated by the ability of the monoclonal antibody directed against the 92.5 kd polypeptide to cross-react with the 115 kd, 140 kd and 160 kd polypeptides.

The relationship of various protein species from the affinity column was demonstrated by immunoprecipitation of iodinated, purified Factor VIIIC with monoclonal antibodies prepared according to the method of G. Kohler and C. Milstein (*Eur. J. of Immunol.* (1975) 6:511). Balb/c mice were immunized with liquid phase immunoadsorbed Factor VIIIC. Spleen cells (10$^8$) were fused with 10$^7$ NSO or NSI mouse myeloma cells. The fusion products were plated into two 96-well microtiter trays. A spleen cell feeder layer was used at 10$^4$ cells/well. Colonies were microscopically visible from the fifth day and the supernatants assayed every few days using an ELISA assay. The following layers were employed: 1st, Factor VIIIC eluted from hexyl-Sepharose 4B column, as described in Section I above; 2nd, hybridoma cell supernatant; 3rd, horseradish peroxidase (HRP)-labeled goat anti-mouse IgG; 4th, HRP-substrate.

Several classes of monoclonal antibodies were identified, two of which inhibited Factor VIIIC coagulation activity: Class I antibodies reacted with the 80/77 kd doublet and 240 kd polypeptides; and Class III antibodies reacted with proteins of 240, 160, 140, 115, 92.5 kd. Immunoprecipitation of thrombin-digested Factor VIII with Class I monoclonal antibodies indicates that the 70/67 kd doublet produced is derived from 77/80 kd doublet (see below). Class III monoclonal antibodies indicate that the 160, 140 and 115 kd peptides are precursors of 92.5 kd peptide. The monoclonal antibodies of Class III further reacted with a 40 kd peptide produced by thrombin digestion of the purified Factor VIIIC material.

An experiment similar to that described above, using EGTA to investigate the role of $Ca^{++}$ ion in the Factor VIIIC complex, was also performed utilizing a monoclonal antibody based ELISA assay with the following layers: 1st, monospecific anti(mouse IgG); 2nd, Class III monoclonal antibody (anti-92.5 kd); 3rd, purified Factor VIIIC material; 4th, HRP-human inhibitor antibody to 77/80 kd. Addition of EGTA removed bound HRP activity present in the control without chelator. The fact that the Class I and III monoclonal antibodies directed to the 77/80 kd doublet and 92.5 kd proteins, respectively, are each inhibitory to Factor VIIIC coagulation activity implicates both as essential components of the Factor VIIIC complex.

B. Thrombin Activation of Factor VIIIC

Aminohexyl-concentrated, affinity-purified Factor VIIIC has been activated by thrombin (Boehringer, lot #1072302) using two different sets of pH conditions (6.8 and 7.4).

Aliquots were assayed for coagulation activity and, in addition, samples (about 2.5 units each) were TCA precipitated for gel analysis. In the first experiments, the VIIIC activity was initially 46 units/ml. This was diluted to a final concentration of 11.5 units/ml in Factor VIIIC buffer (20 mM imidazole, pH 6.8, 150 mM NaCl, 100 mM lysine, 25 mM $CaCl_2$ and 10% glycerol). The final concentration of thrombin was 0.12 unit/ml (about 1 unit of thrombin per 100 coagulation units of VIIIC). The results showed that the coagulation activity increases to about 180 units/ml then decreases to about 40 units/ml (essentially the starting value) coincidentally with a similar increase and decrease in the amount of 92.5 kd species. Thus the 92.5 kd species is implicated as part of the active Factor VIIIC complex.

Additional experiments with more concentrated Factor VIIIC preparations were carried out for the purpose of using thrombin activation in a preparative manner. To generate 92.5 kd polypeptide, thrombin was added to the purified Factor VIIIC material (pH 7.4) at a ratio of about 1000-2000 coagulation units of Factor VIIIC to 1 unit of thrombin activity and allowed to react for only a short period of time (5-15 min, depending on the Hemofil sample). The resulting product was then applied to a 7.5% preparative gel and peptides separated by electrophoresis, the gel bands cut out and electroeluted.

When thrombin digestion is carried out for a short time, the amount of 92.5 kd species can be doubled or tripled; at the same time, the 77/80 kd doublet is only partially converted to 67/70 kd species. To optimize conditions for isolation of the 67/70 kd doublet, a longer time course (greater than 1 h) thrombin digestion is carried out. In this case, the 92.5 kd species is further cleaved to produce smaller fragments. Two new peptides, 52.5 kd and 40 kd appear after thrombin treatment. The 40 kd peptide reacts with the monoclonal antibody directed against the 92.5 kd species and must therefore be a cleavage product. The 52.5 kd peptide is also derived from the 92.5 kd protein as demonstrated by a comparison of chemical and enzymatic cleavage patterns, i.e., both the 92.5 kd and 52.5 kd species when subjected to CNBr or endoproteinase lys C cleavage show a number of common fragments (by SDS-PAGE).

For endoproteinase lys C digestion, a weight ratio of lys C to protein of from about 1:1-100, usually 1:10, is used. In the subject digestion, 20 pmoles (4.8 μg) lys C was combined with 200 pmoles (14 μg) 70 kd polypeptide in about 100 μl 0.025M Tris-HCl, pH 7.7, 0.001M EDTA, 0.08% SDS and the mixture incubated at 37° C. for 6 h to overnight for complete digestion. Native polyacrylamide gels according to Orstein, *Ann. N.Y. Acad. Sci.* (1964) 121:321-349 were used for isolation of lys C digestion products.

C. Thrombin Digestion of Gel Isolated VIIIC-related Proteins

In order to confirm the precursor-product relationship of these peptides, a number of the bands were isolated by preparative SDS gel electrophoresis, electroeluted and subjected to thrombin digestion. The results were as follows:

1 The 240 kd protein produced multiple bands including 160, 140, 115, 92.5 kd but nothing smaller than 92.5 kd, i.e., no 77/80 kd or 67/70 kd doublet. In addition, a time course for digestion was carried out with the 240 kd fragment and analyzed for gel electrophoresis pattern, coagulation activity, and Factor VIIIC antigenic (Cag) activity. Gel results were the same as above and essentially no Cag or coagulation activity was recovered.

2. The 160 kd and 92.5 kd gel-isolated polypeptides do not appear to be substrates for thrombin after isolation from the gel.

3. Thrombin specifically cleaves gel isolated 77 kd and 80 kd species to produce new polypeptides of 67 kd and 70 kd, respectively. After thrombin treatment, monoclonal antibodies of Class I precipitate not only the 77/80 kd doublet, but also the new 67 and 70 kd species.

D. Amino Acid Sequence Analysis

Partial amino acid sequence information was obtained by standard procedures for the 67/70 kd peptides, the 77/80 kd peptides and the 52.5 kd peptide isolated by preparative SDS electrophoresis. The electrophoretic analysis, together with the amino acid sequence results, indicated that the gel-isolated 77/80 kd, 67/70 kd, 92.5 kd and 52.5 kd polypeptides were obtained at >95%, usually 98%, purity. The gel isolated peptides were applied to a gas phase protein sequencer (Applied Biosystems). The PTH-amino acids were applied to an HPLC column (IBM cyano, 25 cm) and the amino sequence determined from the resulting chromatograms.

The following sequence was determined for the 67/70 kd doublet at its amino terminus (indicated with a bar in Appendix B):

| 1 | 2 | 3 | 4 | 5 | 6 | 7 | 8 | 9 | 10 | 11 |
|---|---|---|---|---|---|---|---|---|----|----|
| ? | Phe | Gln | Lys | Lys | Thr | Arg | His | Tys | Phe | Ile |

```
12  13  14  15  16  17  18  19  20  21  22
Ala Ala Val Glu Arg Leu Trp Asp Tyr Gly Met
```

Using the information provided by the amino acid sequence of the N-terminal region of the 67/70 kd protein the following oligonucleotide probes were synthesized to be used to screen human genomic libraries. The phosphoramidite method as described by M. S. Urdea et al., *Proc. Natl. Acad. Sci. USA* (1983) 80:7461–7465 was used:

```
Probe 1: 3' GTA ATA AAA TAA CGX CGX CA 5'
              G   G   G   G
                          T
```

(X = G, C, A, T)

```
Probe 2: 3' AAA GTT TTC TTC TGX T CT GT 5'
              G   C   T   T        C
                                GCX
```

```
Probe 3: 5' GAA CGX TTA TGG GAT TAT GGX ATG 3'
              G AGA   G               C   C
              G CTX
```

```
Probe 4: 3' TCT GTA ATG AAA TAG CGA CGA CAC CTT
              C   G       G       G   G       C

TCT GAC ACC CTA ATG CCG TAC 5'
             C           G
```

A scheme showing regions of amino acid sequence from which each probe is derived is shown below:

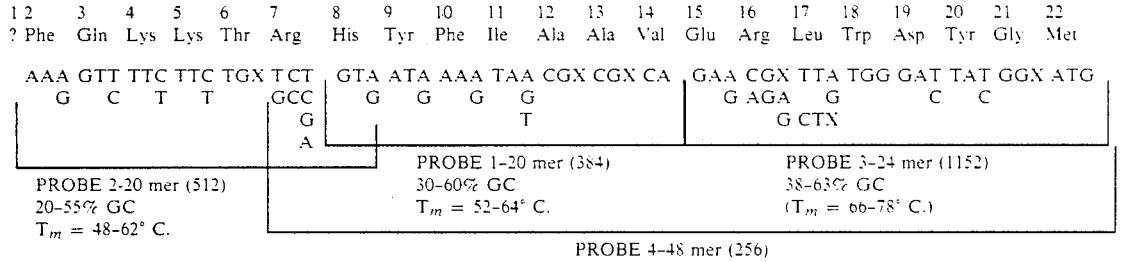

For the 52.5 kd protein, which, as shown below, is derived from the 92.5 kd protein, the following amino acid sequence at the N-terminus was determined:

```
 1   2   3   4   5   6   7   8   9  10  11  12  13
Ala Thr Arg Arg Tyr Tyr Leu Gly Ala Val Glu Leu Ser 14  15  16  17  18  19  20  21 22  23  24  25  26
Trp Asp Tyr Met Gln Ser Asp  ?  Gly Glu Leu Pro Val
```

Based on the amino acid sequence for the 52.5 kd peptide, a partially degenerate probe having the following nucleotide sequence (coding) was synthetized:

```
5'-GCA ACT AGA AGA TAT TAT TTG GGG
      A   G   G           A   A

GCA GTT GAA TTG TCA TGG GAT TAT-3'
     A           A   T
```

This probe is useful for screening both genomic and cDNA libraries.

The amino acid sequences of two peptides obtained by digestion of the 77–80 kd doublet with endoproteinase LysC (Boehringer-Mannheim) were determined. The digestion was performed as follows. The 77–80 kd doublet was electrophoresed on an acrylamide protein gel and bands corresponding to the doublet were electroeluted. The separated material was purified and digested with endoproteinase LsyC, and the resulting peptides were separated by reverse phase HPLC. The fractions corresponding to peaks of absorbance at 280 nm were sequenced using an automated sequencer (Applied Biosystels, Foster City, CA. Model A70A). The first sequence was as follows:

```
 1   2   3   4   5   6   7   8   9  10  11  12
Tyr Ala Ala Thr Ser Gln Val Leu Leu Pro Ser Lys
```

Based on this amino acid sequence, a partially degenerate probe having the following nucleotide sequence (non-coding) strand was synthesized:

```
3'-ATA CGT CGT TGA AGT GTT CAA AAC AAC GG-5'
           T   A       T       T   T
```

The second peptide had the following sequence:

```
 1   2   3   4   5   6   7   8   9  10
Val Thr Gly Val Thr Thr Gln Gly Val Lys
```

Based on this amino acid sequence, a partially degenerate probe having the following nucleotide sequence (non-coding) was prepared:

```
3'-CAA TGA CCT CAA TGA TGA GTT CCT CAA TTT-5'
       T   T       T   T           T
```

The 77/80 kd doublet was also digested with trypsin. The doublet material was purified as described for digestion with endoproteinase LysC, above, lysines were blocked by citraconylation to allow digestion only at arginines. Citraconylation was performed by suspending the proteins in a denaturing buffer, reducing and carboxymethylating the suspended proteins, and treating with citraconic anhydride while maintaining a pH between 8.5 and 9.0. After citraconylation, the proteins were digested with trypsin, and the resulting peptides separated by reverse phase HPLC. The fractions corresponding to peaks of absorbance at 280 nm were sequenced, as above. The sequence was as follows:

```
  1    2   3    4    5   6    7   8    9   10   11  12
 Met  Gly Val  Leu  Gly Cys  Glu Ala  Gln Asp  Leu Tyr
```

Based on this amino acid sequence, a partially degenerate probe having the following nucleotide sequence (non-coding) was synthesized:

```
3'-TAC CTT CAA AAC CCT ACG CTT CGT GTT CTA AAC ATA-5'
        T   T                                T
```

When procedures to determine the N-terminus sequences of the 80 and 77 Kd species were carried out, it was found that their amino termini were blocked. Therefore, the N-termini sequence was determined from material obtained by an alternative purification method which included immunoaffinity chromatography and ion exchange chromatography and precluded the use of preparative SDS-polyacrylamide gel electrophoresis. Purification of the 80/77 Kd doublet involved application of Factor VIIIC concentrate to a monoclonal antibody column followed by chromatography on a mono S cation exchanger. This material had an unblocked N-termini, indicating that the blockage detected in gel purified 80/77 Kd was an artifact resulting from the gel electrophoresis. The amino terminal sequence determined for both 80 and 77 Kd species is the following (indicated with a bar in Appendix B):

```
 1   2   3   4 5 6 7  8  9 10 11 12 13 14 15 16
Glu Ile Thr ? ? ? Leu Gln ? Asp Gln Glu Glu Ile Asp Tyr
```

E. Amino Acid Composition

The amino acid compositions for the 77/80 kd peptides were determined by standard methods to be as follows:

| Amino Acid | 80K | 77K |
|---|---|---|
| Asp | 58 | 54 |
| Glu | 74 | 76 |
| Cys | 12 | 14 |
| Ser | 47 | 44 |
| Gly | 51 | 46 |
| His | 8 | 12 |
| Arg | 32 | 29 |
| Thr | 35 | 29 |
| Ala | 35 | 33 |
| Pro | 33 | 30 |
| Tyr | 25 | 25 |
| Val | 46 | 44 |
| Met | 17 | 17 |
| Ile | 33 | 35 |
| Leu | 49 | 48 |
| Phe | 32 | 31 |
| Lys | 47 | 41 |
| Total No. Amino Acids | 634 | 608 |
| Calculated Molecular Weight: | 82K | 79K |

F. Preparation of Human 4X Genomic Library

Approximately 3 mg of DNA were prepared from cell culture lysates of GM1416 cells (human lymphoblastoid cell line containing 4 copies of the X chromosome).

This DNA was partially digested with the restriction enzyme Sau3A, and the digested DNA (400–500 μg) fractionated on 10%–40% sucrose gradients. Fractions in the size range 10–25 kilobases were pooled, dialyzed into Tris-EDTA and purified over Schliecher and Scheull Elutip-d sterile disposable columns. Aliquots of this DNA were ligated to EMBL-4 arms, obtained after digestion with BamHI and SalI and isolation on a gradient, and then packaged into bacteriophage lambda with an efficiency of $1 \times 10^6$ pfu/μg of insert DNA. The vector used, EMBL-4, is a modified form of bacteriophage lambda (see Karn et al., *Methods Enzymol.* (1983) 101:3–19). The total library consisted of $5 \times 10^6$ phage.

G. Plating and Screening of Human 4X Genomic Library

Bacteriophage were adsorbed to *E. coli* strain DP50 and 20 plates were plated at 50,000 pfu per plate. (150×15 mm size) to give $1 \times 10^6$ pfu total. (Details of techniques for plates, top agar, adsorption and plating are found in *Molecular Cloning, A Laboratory Manual*, by T. Maniatis, E. F. Fritsch and J. Sambrook; Cold Spring Harbor Lab, N.Y., 1982.)

Nitrocellulose filters were applied to the surface of each plate containing phage plaques (so that molecules of unpackaged phage DNA are transferred to the filters) in duplicate, and hybridized with $^{32}$P-labeled 256-fold degenerate 48-mer probe DNA (probe #4). (Details of the nitrocellulose transfer technique are found in Maniatis et al., supra) Pre-hybridization and hybridization were carried out in Wallace mix which contains in one liter: 310 ml of distilled $H_2O$, 200 ml 50% dextran sulfate, 180 ml 1M Tris-HCl, pH 8.0, 225 ml 4M NaCl, 20 ml 0.25M EDTA, 50 ml 100X Denhardt's solution, 5 ml 100% NP-40 and 10 ml 10% SDS.

The probe was labeled by enzymatic transfer of $^{32}PO_4$ from $\gamma$-$ATP^{32}$ to the 5' phosphate end of each probe DNA molecule, catalysed by T4 polynucleotide kinase. The hybridization conditions were as follows: 10 ml hybridization mix/filter × 5000 cpm of labeled probe #4/degeneracy/ml. Hybridization was carried out at 37° C. overnight. Filters were washed in 6XSSC, 1 mM EDTA at 50°–55° C., air dried and used to expose X-ray film.

H. Characterization of Positive Clones

Twenty-three plaques giving positive signals for the first round of screening were replated, phage DNA transferred to nitrocellulose and hybridized with freshly labeled probe #4 (secondaries). Eleven plaques giving positive signals were replated, phage DNA transferred to nitrocellulose and hybridized with freshly labeled probe #4 (tertiaries). Eight plaques giving positive signals were isolated and DNA prepared (100 ml liquid cultures for each). The DNA corresponding to each of these 8 clones was digested with EcoRI (to release inserted human genomic DNA from the lambda vector DNA) and the resulting fragments separated by size using electrophoresis on a 0.8% agarose gel, denatured and transferred to nitrocellulose. This was done in quadruplicate and each filter hybridized with $^{32}$P-labeled probe #'s 1, 2, 3 or 4. The filters were used to expose to X-ray film and a single band of about 4.4 kb in size was found to hybridize with all four probes for two clones. These two clones were identical except that one had more insert DNA than the other (clone designations are 23 D for the larger insert of 15.21 kb and 11 for the smaller insert of approximately 13 kb). The 4.4 kb gel isolated EcoRI fragment was subcloned in vectors M13 and pUC-9 (a derivative of pBR322). DNA sequencing by the dideoxy technique on M13 DNA using the synthetic probe #3 and its reverse complement as primers was carried out.

The 4.4 kb fragment was partially sequenced and has the following sequence encompassing the probe #4 sequence, indicated in parenthesis, and the partial amino acid sequence of the 67/70 kd fragment originally determined, indicated in brackets.

corresponds in part to the human Factor VIIIC complex.

Clone 23D was subcloned in phage M13 as EcoRI fragments, and the sequence corresponding to the inserted human DNA was determined. The complete 15.155 kb sequence of clone 23D sequence is set forth in Appendix A, attached hereto. The subclone designations are given at the right hand margin of the sequence, and refer to the EcoRI-EcoRI fragment extending in the 3'-direction. An open reading frame of 3.110 kb was found to exist from the 3'-end of the 70-3 fragment to the middle of the 4.4 kb fragment. The open reading frame thus comprises at least part of the coding region for the 77/80 kb doublet protein.

```
      1
      val  ser  phe  phe  arg  ala  gln  arg  glu  10
                                                arg  leu  ser  gly  asn
GG    GTC  TCC  TTC  TTC  AGG  GCT  CAG  AGG  GAG  CGA  TTA  AGT  GGC  AAC glu  ala  asn  arg  pro  20
                              gly  lys  leu  pro  phe  leu  arg  val  ala  thr
      GAA  GCA  AAC  AGG  CCT  GGA  AAA  CTT  CCC  TTT  CTG  AGA  GTA  GCA  ACA 30
glu   thr  leu  gln  arg  leu  pro  pro  ser  tyr  40
                                                trp  ile  leu  leu  leu
GAA   ACT  CTG  CAA  AGA  CTC  CCT  CCA  AGC  TAT  TGG  ATC  CTC  TTG  CTT gly  ile  pro  leu trp  tyr  50
                              ser  glu  tyr  gln  lys  lys  ser  gly  lys
      GGG  ATA  CCA  CTA  TGG  TAC  TCA  GAG  TAC  CAA  AAG  AAG  AGT  GGA  AAG 60
ser   gln  glu  lys  ser  pro  glu  lys  thr  ala  70
                                                phe  lys  lys  lys  asp
TCC   CAA  GAG  AAG  TCA  CCA  GAA  AAA  ACA  GCA  TTT  AAG  AAA  AAG  GAT thr   ile  leu  ser  leu  80
                        asn  ala  cys  glu  ser  asn  his  ala  ile  ala
ACC   ATT  TTG  TCC  CTG  AAC  GCT  TGT  GAA  AGC  AAT  CAT  GCA  ATA  GCA 90
ala   ile  asn  glu  gly  gln  asn  lys  pro  glu  100
                                                 ile  glu  val  thr  trp
GCA   ATA  AAT  GAG  GGA  CAA  AAT  AAG  CCC  GAA  ATA  GAA  GTC  ACC  TGG ala   lys  gln  asn  arg  110
                        thr  glu  arg  leu  cys  ser  gln  asn  pro  pro
GCA   AAG  CAA  AAT  AGG  ACT  GAA  AGG  CTG  TGC  TCT  CAA  AAC  CCA  CCA 120
val   leu  lys  arg  his  gln  arg  glu  ile  thr  130
                                                 arg  thr  thr  leu  gln
GTC   TTG  AAA  CGC  CAT  CAA  CGG  GAA  ATA  ACT  CGT  ACT  ACT  CTT  CAG ser   asp  gln  glu  glu  140
                        ile  asp  tyr  asp  asp  thr  ile  ser  val  glu
TCA   GAT  CAA  GAG  GAA  ATT  GAC  TAT  GAT  GAT  ACC  ATA  TCA  GTT  GAA 150
met   lys  lys  glu  asp  phe  asp  ile  tyr  asp  160
                                                 glu  asp  glu  asn  gln
ATG   AAG  AAG  GAA  GAT  TTT  GAC  ATT  TAT  GAT  GAG  GAT  GAA  AAT  CAG ser   pro  arg  ser  [phe  170
                        gln  lys  lys  thr  (arg  his  tyr  phe  ile  ala
AGC   CCC  CGC  AGC   TTT  CAA  AAG  AAA  ACA  CGA  CAC  TAT  TTT  ATT  GCT 180
ala   val  glu  arg  leu  trp  asp  tyr  gly  met)] 190
                                                 ser  ser  ser  pro  his
GCA   GTG  GAG  AGG  CTC  TGG  GAT  TAT  GGG  ATG  AGT  AGC  TCC  CCA  CAT val   leu  arg  asn  arg  200
                        tyr  glu  cys  ile  gly  tyr  ser  phe  ala  leu
GTT   CTA  AGA  AAC  AGG  TAT  GAA  TGC  ATT  GGT  TAT  TCC  TTT  GCT  CTG 210  211
      leu  leu  OP
      CTC  TTG  TGA  CATTTGACTTTACCAGATGATGACACCAACC
```

This clone thus corresponds to the gene for the 77/80 kd doublet protein, which, as it has been shown above,

I. Preparation of Full-length cDNA Clones

(1) Initial Constructions

Three cDNA clones encoding portions of Factor VIIIC were obtained as follows. Clone C1 was obtained by screening a human liver cDNA library with a probe constructed from the 4.4 kb EcoRI fragment of clone 23 D. Clone C2 was also obtained by screening a human liver cDNA library with the 4.4 kb probe. Clone 2-11 was obtained by screening a human kidney cDNA library with a synthetic 45-mer probe based on the DNA sequence found at the 3'-end of the open reading frame of clone 23 D (nucleotides 9391 to 9435 in Appendix A). The probe comprised the non-coding strand of the following sequence:

```
              Ser Pro Arg Ser Phe Gln Lys Lys
          5'-AGC CCC CGC AGC TTT CAA AAG AAA
Non-coding- 3'-TCG GGG GCG TCG AAA GTT TTG TTT
(probe)

Thr Arg His Tyr Phe Ile Ala
          ACA CGA CAC TAT TTT ATT GCT-3'
          TGT GCT GTG ATA AAA TAA CGA-5'
```

The clones were sequenced and their locations relative to the genomic DNA of clone 23 D determined by comparing the sequences. Clone C1, which is 304 kp in length, overlaps with the open reading frame from nucleotide 7773 to 8077, as numbered in Appendix A. Clone C2, which is 878 bp in length, partially overlaps with the 3'-end of the open reading frame beginning at nucleotide 9538 and extending beyond nucleotide 9497 which is at the 3'-end of the open reading frame. Clone 2-11, which is 572 bp in length, also overlaps the 3'-end of the open reading frame beginning at nucleotide 9190 and extends beyond its termination. These findings thus confirm that the open reading frame is transcribed.

The coding information derived from the 4.4 kb open reading frame may be combined with the additional coding information derived from clones 2-11 and C2 to provide a 3.854 kb coding sequence containing all but about 4 kb of the full coding sequence (See, Appendix B). The regions corresponding to the C1, C2 and 2-11 probes are boxed.

To prepare Factor VIIIC fragments, the DNA sequences from Clone 23 or Clone 11 are inserted into an SV-40 promoter as described by Laub et al., *J. Virology* (1983) 48:271, so as to be under the control of the SV-40 early promoter. The resulting recombinant plasmid may be transfected into COS cells (Guzman, supra.). Alternatively, the coding sequence can be inserted into a plasmid, e.g., pBR322, into which has been inserted the long terminal repeats of Maloney murine sarcoma virus, so that the Clone 23 or 11 sequences are under the transcriptional control of the viral regulatory system. The constructs may then be introduced into 3T3 mouse fibroblasts for efficient expression (see Perkins et al., *Molecular and Cellular Biology*, June 1983, Vol. 3, No. 6, p. 1123).

(2) Further 3' cDNA Region Construction

An oligo-dT-primed cDNA library was prepared from human kidney poly A+ RNA using the primer adapter method. Briefly, poly A+ RNA isolated from human kidney was primed at the 3' end of the mRNA using a primer (F-1) having the following sequence:

```
                XbaI        BglII     PstI    BamHI
5'     GCGTCTAGAAACCCTTTAGATCTGCTGCAGCG         3'
3' TTTTTTTTTTTTTTTTTCGCAGATCTTTGGGAAATCTAGACGACGTCGCCTAG5'
                                                    BamHI
``` single-stranded cDNA was synthesized and size-selected on denaturing agarose-methyl mercury gels to isolate fragments greater than 2 kb. The cDNA fragments were eluted, C-tailed, annealed to adapters and placed in a pUC9 vector (Pharmacia Fine Chemicals, Piscataway, N.Y.), ligated, repaired using T4 DNA polymerase and finally transformed into *E. coli* MC1061. Approximately 500,000 clones were obtained.

This library was divided into 20 pools and analyzed by Southern hybridization after digestion with PstI, using the 4.3 kb EcoRI genomic fragment described previously as a probe. In one of the pools, pool 1-7, a clone was found to contain fragments hybridizing to the genomic probe.

Further PstI digestion of the clone yielded two fragments of about 1350 and 600 bp that hybridized to the 4.3 kb EcoRI probe. Hybridization of a 600 bp fragment was expected based on the sequence of the 4.3 kb fragment. Upon probing with a piece of the 3' end of the C2-cDNA described previously, a new 1200 bp fragment was located by hybridization. However, only the 600 bp fragment hybridized to a separate piece from the 5' end of the C2-cDNA. Based on this information, it was believed that the 5 kb cDNA clone encompassed more than the entire 3' half of the human Factor VIIIC precursor protein coding region.

To minimize stability problems experienced after plating with high-efficiency rec+ bacteria on large inserts, DNA from pool 1-7 was digested with XmaI (which linearizes the positive plasmid), run on a low melting agarose gel, and one region corresponding to a molecular weight of about 7.5 kb was excised. This DNA was extracted from the agarose, recircularized with DNA ligase and subsequently used to transform bacteria. Approximately 25,000 colonies were plated and reanalyzed by colony hybridization to the 4.3 kb EcoRI fragment. Two positive colonies were obtained and, for high purity, isolated by two further cycles of plating hybridization. The resultant clone, designated pF8-100, contains an insert of about 5,000 bp, which after digestion with PstI gives five fragments of approximately 1600, 1350, 1200, 600 and 200 bp. Utilizing the M-13 dideoxy method, the 5 kb cDNA insert has been completely sequenced, as shown in FIG. 1. The insert contains the last 60% of the coding region and substantially all of the 3' untranslated region of the human kidney messenger RNA for Factor VIIIC.

(3) Further 5' cDNA Region Construction

To obtain the 5' region of human Factor VIIIC cDNA, approximately 1×10⁶ clones with an average insert size of about 3 kb were obtained from a total of four independent transformation experiments utilizing a cDNA library constructed as described previously using the F-1 primer, but in addition using a second primer (303) that has the following sequence located near a BglII site of the pF8-100 cDNA clone:

5' CCATTACTCAGTCTCCCTTATCAGATTGCCTTACGAGGAG 3'
3' TAGTCTAACGGAATGCTCCTCCTAG 5'.

For initial screening, the transformant pools were linearized with SmaI and produced a broad DNA band in the 5 to 7 kb region on the gels. For further screening, the library was divided into 16 pools and the DNA analyzed by Southern hybridization, probing with the 4.3 kb EcoRI fragment. Of the first four pools analyzed, two showed the presence of a hybridizing band in the 6.5 to 7 kb range, the size expected for the total of the base pairs in the vector plus the base pairs of the Factor VIIIC cDNA extending from the site of internal priming to the 5' end (about 4 kb).

To confirm that the positive pools contained the 5' end cDNA sequences coding for human Factor VIIIC cDNA, cDNA inserts from the pools was digested with SmaI and SacI, which should cut the cDNA into two pieces of approximately 1 and 3 kb. When the fragments were analyzed by Southern hybridization using the 4.3 kb EcoRI fragment as a probe, as expected, the two fragments hybridized—indicating that this insert contained the 5' region of the Factor VIIIC cDNA.

For isolation of a single cDNA clone, approximately 200,000 transformants from one of the positive pools were plated, lifted onto nitrocellulose filters and hybridized to nick-translated 4.3 kb EcoRI probes. Six double positive colonies were obtained, two of which were isolated as single colonies by replating. One of these clones was a 3.8 kb insert designated pF8-103, which contained the 3' end of the Factor VIIIC cDNA; while the other clone of about 4 kb, designated pF8-102, was isolated and subjected to further analysis.

The pF8-102 cDNA insert was digested with HindIII, PstI, SstI (SacI), EcoRI, BamHI, FpHI, BglII and SmaI. It was also cloned in M13. Sequence was obtained from the universal primer, as well as internally, using various specific synthetic primers. The sequence obtained is presented in FIG. 1, which together with the sequence for pF8-100, provide a cDNA encoding the entire human Factor VIIIC coding region.

(4) Full-length cDNA Assembly

Details of the assembly of a full-length cDNA for expression in mammalian cells is shown in FIG. 2. The lack of convenient restriction sites in the pF8-100 and pF8-102 overlap region required the use of DNA fragments derived from the 4.3 kb EcoRI genomic fragment as well. Plasmid pF8/4.5 contains the 4.3 kb EcoRI fragment clone in pUC9.

Briefly, pF8-100 was cut with SmaI and AbaI, and a 4.8 kb fragment was isolated by gel electrophoresis. Likewise, a 1.7 kb fragment was obtained from pF8/4.5 by digestion with AbaI and EcoRI. These two fragments were ligated into open pUC9 (cleaved with SmaI and EcoRI) to yield a plasmid designated pF8/6.5. Cutting this plasmid with SacI and SalI yielded a 6.5 kb fragment (Fragment 1). A second fragment (Fragment 2) was obtained by cutting pF8-102 with SacI, which upon gel isolation yielded a 3 kb piece. Fragments 1 and 2 were subsequently ligated into a modified vector pSV7d to yield expression plasmid pSVF8-200, which is capable of expressing human Factor VIIIC protein.

The plasmid pSV7d was constructed as follows: the 400 bp BamHI/HindIII fragment containing the SV40 origin of replication and early promoter was excised from pSVgtI (Mulligan, R. et al., *J. Mol. Cell Biol.* (1981) 1:854–864) and purified. The 240 bp SV40 BclI/BamHI fragment containing the SV40 poly A addition site was excised from pSV2/dhfr (Subramani et al., *J. Mol. Cell Biol.* (1981) 1:854–864) and purified. The fragments were fused through the following linker:

Stop Codons
1  2  3

5'-AGCTAGATCTCCCGGGTCTAGATAAGTAAT-3'
   TCTAGAGGGCCCAGATCTATTCATTACTAG

HindIII   BglII   SmaI   XbaI   BclI overhang.

This linker contains five restriction sites, as well as stop codons in all three reading frames. The resulting 670 bp fragment (containing the SV40 origin of replication, the SV40 early promoter, the polylinker with stop codons and the SV40 polyadenylation site) was cloned into the BamHI site of pML, a pBR322 derivative with about a 1.5 kb deletion (Lusky and Botchan, *Cell* (1984) 36:391), to yield pSV6. The EcoRI and EcoRV sites in the pML sequences of pSV6 were eliminated by digestion with EcoRI and EcoRV, treated with Bal31 nuclease to remove about 200 bp on each end, and finally religated to yield pSV7a. The Bal31 resection also eliminated one BamHI restriction site flanking the SV40 region, approximately 200 bp away from the EcoRV site. To eliminate the second BamHI site flanking the SV40 region, pSV7a was digested with NruI, which cuts in the pML sequence upstream from the origin of replication. This was recircularized by blunt end ligation to yield pSV7b.

pSV7c and pSV7d represent successive polylinker replacements. Firstly, pSV7b was digested with StuI and XbaI. Then, the following linker was ligated into the vector to yield pSV7c:

BglII   EcoRI   SmaI   KpnI   XbaI

5'-AGATCTCGAATTCCCCGGGGGTACCT
   TCTAGAGCTTAAGGGGCCCCCATGGAGATC

Thereafter, pSV7c was digested with BglII and XbaI, and then ligated with the following linker to yield pSV7d:

BglII   EcoRI   SmaI   XbaI   BamHI   SalI

5'-GATCTCGAATTCCCCGGGTCTAGAGGATCCGTCGAC
   AGCTTAAGGGGCCCAGATCTCCTAGGCACGTGATC

Plasmid pSV7d was digested with BamHI to cut in the polylinker region downstream of the SV40 early promoter. The following 49 bp BamHI-SacI linker adaptor, which codes for the last 30 bp of untranslated region and the first 15 bp of the human Factor VIIIC coding sequence, was chemically synthesized and ligated to pSV7d:

```
         -35     -30      -25     -20     -15     -10     -5       met  gln  ile     glu
      5' GATCC  TCTCC    AGTTG   AACAT   TTGTA   GCAAT   AAGTC    ATG  CAA  ATA    GAG  CT 3'
         BamHI3'G AGAGG  TCAAC   TTGTA   AACAT   CGTTA   TTCAG    TAC  GTT  TAT C SacI    5'
```

This ligated plasmid was subsequently digested with SacI to remove excess linkers and with SalI to provide a SalI overhang.

Fragment 1, the 2.9 kb SacI fragment from pF9-102 containing the 5' coding region of human Factor VIIIC, and Fragment 2, the 6.5 kb SacI-SalI fragment from pF8-6.5 which contains the 3' coding region of the factor, and pSV7d modified vector containing the linker adaptor were ligated together. This ligation mix was then used to transform *E. coli* HB101, and colonies were selected by resistance to ampicillin.

300 transformants were screened by colony filter hybridization using the BamHI-SacI 5' adaptor or the 2.9 kb SacI fragment as probes. Those colonies positive with both probes were then analyzed by restriction mapping. Plasmid pSVF8-200, which contains the entire coding region for the human Factor VIIIC gene and a 5' untranslated region properly fused in transcriptional orientation to the SV40 early promoter, was obtained.

(5) Transfections and Assays

Utilizing the chloroquine diphosphate transfection method (Luthman and Magnuson (1983) *Nucl. Acid. Res.*, 11:1295–1308), Cos-7 cells growing in 4 cm² slide wells were transfected with 0.5 micrograms of pSVF8-200 in the presence of calcium. At 40, 48 and 60 hours post-transfection, cell culture media was removed and tested for human factor VIIIC activity using the coagulation assay described previously (General Diagnostics, Inc.). The cells remaining on the slides were fixed with methanol for indirect immune fluorescense studies.

The fixed slides were stained with six different antibodies against human Factor VIIIC and a second antibody labeled with FITC (Cappel Labs). The partial results are shown in the following table:

TABLE I

| 1st Antibody | Goat 2nd Antibody Conjugation with FITC | Results | |
|---|---|---|---|
| 1. Hybritech monoclonal anti-FVIIIC | anti-mouse | (+/−) | All FVIII: C cells |
| 2. Synbiotic monoclonal anti-FVIIIC (80 kd specific) | anti-mouse | | looked slightly more positive |
| 3. Monoclonal #56 anti FVIIIC (Nordisk) | anti-mouse | | than negative controls |
| 4. Human polyclonal inhibitory serum (HZ) (Nordisk) | anti-human | (+) | Low background and bright FVIII: C positive cells |
| 5. Rabbit polyclonal against 92 kd (Chiron) | anti-rabbit | (−) | Both control and transfected cells show low fluorescence |
| 6. Rabbit polyclonal against 80 kd (Nordisk) | anti-rabbit | (+) | Clear FVIII:C positives seen with 48 hr. cells |

The human polyclonal showed positive immunofluorescent cells at 48 and 60 hours post-transfection. The 80 kd rabbit polyclonal showed positive cells at 48 hours post-transfection. All other antibodies gave high backgrounds, rendering accurate determinations impractical.

The production of active human Factor VIIIC by the transfected Cos cells was detected using the previously described commercially available kit coagulation assay (General Diagnostics, Inc.). However, it was found that Cos cell medium interfered with the coagulation assay by indicating apparent coagulation activity equal to about 0.05 units per ml. This apparent activity is probably caused by a serum component present in the medium. Cos cell conditioned medium gave about the same apparent activity as fresh medium, i.e., medium that had not been used for growing cells.

To correct for the apparent activity of the Cos cell medium, a revised standard curve was established using serial dilutions of a purified Factor VIIIC preparation (purified from cryoprecipitate, as previously described) diluted in Cos cell conditioned medium with serum. Supernatants from Cos cells transformed with the plasmid pSV8-200 were then assayed for clotting activity. As shown in Table II, samples taken at 40 hours post-transformation, and frozen immediately at −70° C. until assay, had about 0.045 units per ml activity, the 48 hour sample had about 0.055 units per ml activity, while the 60 hour sample had about 0.07 units per ml activity.

TABLE II

Detection of Coagulation Activity in COS Cells Transformed with Factor VIII:C Gene

| Sample | | Coagulation Time (sec.) | Activity (units/ml) |
|---|---|---|---|
| Purified FVIII preparation 1:5,000 dilution | | 35.9 | 0.23ˣ |
| Purified FVIII preparation 1:10,000 dilution | | 48.4 | 0.11ˣ |
| Purified FVIII preparation 1:20,000 dilution | | 55.9 | 0.058ˣ |
| Purified FVIII preparation 1:40,000 dilution | | 67.9 | 0.028ˣ |
| 40 hr sample | 2a | 58.9 | 0.049ʸ |
| | 2b | 61.9 | 0.041ʸ |
| 48 hr sample | 1a | 58.2 | 0.051ʸ |
| | 1b | 56.9 | 0.057ʸ |
| 60 hr sample | 1a | 52.4 | 0.086ʸ |

TABLE II-continued

Detection of Coagulation Activity in COS Cells Transformed with Factor VIII:C Gene

| Sample | Coagulation Time (sec.) | Activity (units/ml) |
|---|---|---|
| 1b | 56.4 | 0.060[y] |

[x] Activity calculated from normal standard curve using the same dilutions of FVIII in coagulation buffer rather than COS cell conditioned medium.
[y] Activity calculated from modified standard curve using COS cell conditioned medium as a diluent.

To confirm that the coagulation activity detected in the Cos cells/Factor VIIIC transfectant media was due to active Factor VIIIC protein sequences, the media was preincubated with an inhibitory human polyclonal anti-Factor VIIIC antibody (HZ antibody, Nordisk) known to specifically inhibit Factor VIIIC activity. The coagulation assay was performed essentially as detailed above, but each sample was pre-incubated with the antibodies for about 2 hr. at 37° C. The assay results are shown in Table III.

TABLE III

| Media | Preincubation[a] | Antibody | Dilution[b] | Coagulation Time (sec.) |
|---|---|---|---|---|
| COS cell | — | — | — | 108.9 |
| COS cell/pSVF8-200 | — | — | — | 83.4 |
| COS cell/pSVF8-200 | — | — | — | 84.4 |
| COS cell/pSVF8-200 | + | F3A/B | 1/100 | 81.9 |
| COS cell/pSVF8-200 | + | HZ IgG | 1/100 | 110 |
| COS cell/pSVF8-200 | + | HZ IgG | 1/500 | 105.4 |
| COS cell/pSVF8-200 | + | HZ IgG | 1/1,000 | 103.9 |
| COS cell/pSVF8-200 | + | HZ IgG | 1/10,000 | 98.4 |

[a] Incubation was for 2h at 37° C.
[b] Dilutions were made in coagulation buffer.

As shown in Table III, the COS cell/FVIII:C media clearly has an accelerated clotting time compared to the COS cell media alone. Preincubation of this media for 2 h at 37° C. did not prolong the clotting time nor did preincubation in the presence of a monoclonal antibody directed against a major herpes simplex glycoprotein (F3A/B). However, preincubation with various concentrations of human inhibitor serum (HZ IgG) clearly retarded the coagulation time, approximately equal to that of the control reaction. These results confirm that transfected COS cells produce and secrete active FVIIIC protein.

The above results also demonstrate that genomic DNA sequences have been isolated which code for portions of the Factor VIIIC protein. By use of this genomic DNA, the DNA may be further manipulated to provide for a sequence encoding for Factor VIIIC complex subunits. The DNA may then be used in an expression vector for production of the Factor VIIIC, which may be used in a variety of ways, for example, as reagents in diagnostic assays, as therapeutic agents, for the production of monoclonal or polyclonal antibodies, which may then be used for the purification of Factor VIIIC complex or other purposes. The genomic DNA sequences may also be used for isolation of mRNA encoding proFactor VIIIC to provide for the precursor protein. This protein may then be administered in vivo for various therapeutic purposes.

Although the foregoing invention has been described in some detail by way of illustration and example for purposes of clarity of understanding, it will be obvious that certain changes and modifications may be practiced within the scope of the appended claims.

APPENDIX A

```
  1 GAATTCCCCGGATCTCTTATATTCCATTGACTTATTGGTCTATCTTTGTACCAGTAACAT EcoRI #81
    CTTAAGGGGCCTAGAGAATATAAGGTAACTGAATAACCAGATAGAAACATGGTCATTGTA 1 ecorI, 10 binI, 61 ACTATCTTATAGTAAGTTTTAATATTTGTTAGTATAATTCCTCCAACTTTGCTCTCTTTG
    TGATAGAATATCATTCAAAATTATAAACAATCATATTAAGGAGGTTGAAACGAGAGAAAC 121 ATTTTTATATAAATTTTAGAATCATCTTGTCAATTTTATCAATAAAAATATCTTCTGAGG
    TAAAAATATATTTAAAATCTTAGTAGAACAGTTAAAATAGTTATTTTTATAGAAGACTCC 171 mboII, 181 TTTTGATAGGGATTACATTGATTCTGCAGATCAATTTGGGGGAGCATACCTCTTGACAAT
    AAAACTATCCCTAATGTAACTAAGACGTCTAGTTAAACCCCCTCGTATGGAGAACTGTTA 204 pstI, 241 ATTGAGTATTCCTGTCCATGAGCATGGTTTAGTTATTTATTTACATCTTTTAAATTTTCT
    TAACTCATAAGGACAGGTACTCGTACCAAATCAATAAATAAATGTAGAAAATTTAAAAGA 256 bstXI, 289 ahaIII, 301 CTTGGCAATGTTTTTGTAAAATTTTAGTGTACAGGTCTTGCACATTTTTGTAAAGTGTAT
    GAACCGTTACAAAAACATTTTAAAATCACATGTCCAGAACGTGTAAAAACATTTCACATA 361 TCTTTGGTATTTAATGCTATTATAATATTTTTTATGGTATCAGTTTTTGTCAATTGTGTT
    AGAAACCATAAATTACGATAATATTATAAAAAATACCATAGTCAAAAACAGTTAACACAA 421 TTTCTAGAAATATGTCCCTTTCATCTAAGTTGTTTAATTTACTTGAAGTAAGTTATTTGT
    AAAGATCTTTATACAGGGAAAGTAGATTCAACAAATTAAATGAACTTCATTCAATAAACA 423 xbaI, 481 AATGTTCTTTTATCATCCTTATAATGTCTGTACTGATGTCTCCGTTTTCATACCTGATAT
    TTACAAGAAAATAGTAGGAATATTACAGACATGACTACAGAGGCAAAAGTATGGACTATA 541 TGTTATTTATATTTTATCTATTTTAAGTTTATCGCCTGCACCCACTAACTCGTCATCTAG
    ACAATAAATATAAAATAGATAAAATTCAAATAGCGGACGTGGGTGATTGAGCAGTAGATC 601 CATTAGGTATATCTCCCAATGATATCCCTCGCCCCTCCCCCTAGTGCACATGTACCCTAA
    GTAATCCATATAGAGGGTTACTATAGGGAGCGGGGAGGGGGATCACGTGTACATGGGATT 621 ecoR5, 661 AACTTAAAGTATAATAAAAAAAAAAAAGTTTGTCGCCTTTGTTATAGGTTCATCAAATTTA
    TTGAATTTCATATTATTTTTTTTTTCAAACAGCGGAAACAATATCCAAGTAGTTTAAAT 721 CTAATCCTACCATAGGATCAAATTTTTGCTTTGTTCATCAGGTCATGGAATTAAAAAAAT
    GATTAGGATGGTATCCTAGTTTAAAAACGAAACAAGTAGTCCAGTACCTTAATTTTTTTA 735 binI, 781 TTTTTTGTTTTGTTTATTTTCTATGTTGAATTTTTATTTTTATTTGCTTTGCATTTCAT
    AAAAAACAAAACAAATAAAAGATACAACTTAAAAATAAAAATAAAACGAAACGTAAAGTA 841 TTATTTCTGGTCTTTTGTTATTATTCCAATACTTTCTCTGGATTCAGTTTTCTTTTTCTT
    AATAAAGACCAGAAAACAATAATAAGGTTATGAAAGAGACCTAAGTCAAAAGAAAAGAA 897 mboII, 901 CTTGACTTCTTGAGATTAAAACTTGGTTCATTGATTTTCAACATTTCTTACTTTTTAAAA
    GAACTGAAGAACTCTAATTTTGAACCAAGTAACTAAAAGTTGTAAAGAATGAAAAATTTT 954 ahaIII, 961 GTTCATACAAAGCATAAATTTCCCTTTATATACTGCTTTAACCCCATATCACAAATTTTG
    CAAGTATGTTTCGTATTTAAAGGGAAATATATGACGAAATTGGGGTATAGTGTTTAAAAC 1021 ATGAGTCATATTTTTATTATCATTGAGTTTAAAATATTTTATAAATTTTACGTTATTTCT
    TACTCAGTATAAAAATAATAGTAACTCAAATTTTATAAAATATTTAAAATGCAATAAAGA 1048 ahaIII, 1081 TGTTTTATTCATAGTTATTTTACAGTGTTTTACTTAATTTCCCAATATATGGCGATTTTC
    ACAAAATAAGTATCAATAAAATGTCACAAAATGAATTAAAGGGTTATATACCGCTAAAAG 1141 TGGCTCTCTCTCTGTTGCTGATTTATTTGTTTTACTGTGATCACATAACATACTCTATAT
    ACCGAGAGAGAGACAACGACTAAATAAACAAAATGACACTAGTGTATTGTATGAGATATA 1178 bclI, 1201 TATTTCAATCATTTGAAATTTGTTGAGACTTGCTATATGCCCAGTGAATAATTTAATTTG
    ATAAAGTTAGTAAACTTTAAACAACTCTGAACGATATACGGGTCACTTATTAAATTAAAC 1261 ATTAATGGCCCACTGCATTTGAAACAAATATGTCTTTGCTGTTATTGGGTAGAGTGTCAT
    TAATTACCGGGTGACGTAAACTTTGTTTTATACAGAAACGACAATAACCCATCTCACAGTA
```

```
1321 ATATTTGCCTATTATGTCAAGTTGCTTTATCATGTTTTTAAAATCCTTATAAACTTCCTG
     TATAAACGGATAATACAGTTCAACGAAATAGTACAAAAATTTTAGGAATATTTGAAGGAC 1357 aha111, 1381 ATATTTTATCTGTTTCTTACAGACATGGAGGAAACTGTGACATCTCTGTGATTGTTGAGT
     TATAAAATAGACAAAGAATGTCTGTACCTCCTTTGACACTGTAGAGACACTAACAACTCA 1441 TTGTTATTTTGATTTTTGTATTTGTTAGTAAGAATGTTTCAAAATAAATGAGGCAATATA
     AACAATAAAACTAAAAACATAAACAATCATTCTTACAAAGTTTTATTTACTCCGTTATAT 1501 AAATCAGGTGCTTACAACTTTAAGGTTGTATTCTTATTAAATCAATTCTTTCATCTTTGT
     TTTAGTCCACGAATGTTGAAATTCCAACATAAGAATAATTTAGTTAAGAAAGTAGAAACA 1561 GAAATGTCCTTTTTGTCTGAAGTAGTACTTGTTGCCTTAAACGTCTGCATTGTCTAAAAT
     CTTTACAGGAAAAACAGACTTCATCATGAACAACGGAATTTGCAGACGTAACAGATTTTA 1584 sca1, 1621 TTATACACCTGCACTATCATATTTATTTTGCTTAATGTTTGTGTGGTATATATTTCCCAT
     AATATGTGGACGTGATAGTATAAATAAAACGAATTACAAACACACCATATATAAAGGGTA 1681 TCTTTTCTTTTCAACCTATCTCTATCCTTATATTTACAGTGTGTCTTTTTAACATTTTC
     AGAAAAGAAAAGTTGGATAGAGATAGGAATATAAATGTCACACAGAAAAAATTGTAAAAG 1741 TGTAGTGCAAGTCTGTTGGTTAATTAATTTTGTCAGTTTTTGCTTCTCTGAAAAGTCTTT
     ACATCACGTTCAGACAACCAATTAATTAAAACAGTCAAAAACGAAGAGACTTTTCAGAAA 1801 ATTTCTGTTTTTGAATTATATCTTCACTGTGTATAGAATTCTGGGTTTGTGGTTGTTGTT    EcoRI #61
     TAAAGACAAAAACTTAATATAGAAGTGACACATATCTTAAGACCCAAACACCAACAACAA 1821 mbo11, 1836 ecor1, 1861 TTTGTTTTATTACATTTGTTTTATTGGTTTTTCCCTCAGCACTTTAAAAATGCCGCTCC
     AAACAAAATAATGTAAAACAAAATAACCAAAAAGGGAGTCGTGAAATTTTTACGGCGAGG 1904 aha111, 1921 ATTGTTTCTACTTGCATAGTTTTTCACAATAAGTTTGTTGTAATTCCCATTTGCATTCAA
     TAACAAAGATGAACGTATCAAAAAGTGTTATTCAAACAACATTAAGGGTAAACGTAAGTT 1981 CTGTACATAATGTATCTTTTTAAAAAAATCTGGATGGCTTCAAGCTCTTTACTTTGATTT
     GACATGTATTACATAGAAAAATTTTTTTAGACCTACCGAAGTTCGAGAAATGAAACTAAA 1999 aha111, 2041 TTGTGTGTGTGTGTGTGTGTGTGTGTGTGTGTGTGTGTGTGTTACTTTGGCATTCTCTAG
     AACACACACACACACACACACACACACACACACACACACAATGAAACCGTAAGAGATC 2101 GCTTATTCAATCTGTAATTTGGTATCATTAATTTTGAAAAATATTTATCATCTGTGTCTT
     CGAATAAGTTAGACATTAAACCATAGTAATTAAAACTTTTTATAAATAGTAGACACAGAA 2157 mbo11, 2161 CAAATATTGCTTCTAATTCTTTCTCTTCTTCTGGTATTGCATTTACATATATTATACTGT
     GTTTATAACGAAGATTAAGAAAGAGAAGAAGACCATAACGTAAATGTATATAATATGACA 2184 mbo11, 2187 mbo11, 2221 TCAATTTTGTCACACAGCTCTTGAATATGCTGTTCTAGTTTGTTTTCTAACTATTTTCC
     AGTTAAAACAGTGTGTCGAGAACTTATACGACAAGATCAAACAAAAGATTGATAAAAGG 2281 TTCTAGTTGTTCAGTTTTGTTGACATTTATTGACCTATTTTACTTCAGTAATTGTTTCC
     AAGATCAACAAGTCAAAACAACTGTAAATAACTGGATAAAAATGAAGTCATTAACAAAGG 2341 TGGGTTGTTGAGTTAATTGATGAACTCATAGATGACATACAATTTATCTTTTTATTCTTG
     ACCCAACAACTCAATTAACTACTTGAGTATCTACTGTATGTTAAAATGAAAAATAAGAAC 2401 TGTCACTTGTGCTTTTGATGTCACATCTAGGAAGGCTTTGTCTAGCCCAAGGCCACATTT
     ACAGTGAACACGAAAACTACAGTGTAGATCCTTCCGAAACAGATCGGGTTCCGGTGTAAA 2461 ACTTCCATATTTTCTTCTAAGAGTTTGATAGTTGTAGCTGTTACATATATGTCTATGATC
     TGAAGGTATAAAAGAAGATTCTCAAACTATCAACATCGACAATGTATATACAGATACTAG 2473 mbo11, 2521 TAGTTTGAATAAATTTTTGTGTATGGTGTGAAGAAGAGGTCTAACCTCTTTTTTATTTTT
     ATCAAACTTATTTAAAAACACATACCACACTTCTTCTCCAGATTGGAGAAAAAATAAAAA 2550 mbo11, 2553 mbo11, 2581 TGCATGTAAACATCCAGTTGTCCCGGCACCATTTGTTGAAAATATGATTCTTTTCCCATT
     ACGTACATTTGTAGGTCAACAGGGCCGTGGTAAACAACTTTTATACTAAGAAAAGGGTAA 2641 AAGTCATCTTGACACCCTTGTTGAAAATCAATTGACCATAAATGTGAGAGTTTATTTCTG
     TTCAGTAGAACTGTGGGAACAACTTTTAGTTAACTGGTATTTACACTCTCAAATAAAGAC 2701 AACTCTCCATTCTGTTCCATTGACCCATACGTCTTCTATAAATTCCTTATAGCTAATTCT
     TTGAGAGGTAAGACAAGGTAACTGGGTATGCAGAAGATATTTAAGGAATATCGATTAAGA 2732 mbo11,
```

```
2761  ACATTAGACTTTGGTTTTTTCAGATGTGGTCATCTCATTAGATTATGGTGATATGTTTGGT
      TGTAATCTGAAACCAAAAAGTCTACACCAGTAGAGTAATCTAATACCACTATACAAACCA

2821  TACAAGTTTTATCTTCTCCTTGGCAACATTTTTTTTATTACTGCTCTTCTTTTATTCGTT
      ATGTTCAAAATAGAAGAGGAACCGTTGTAAAAAAATAATGACGAGAAGAAAATAAGCAA 2832 mbo11,  2865 mbo11, 2881  TTTGTTGTTCCTTTCTCTTTTTGTGAGACAGGGTCTCACTCTGTTGCCCAGGGTGGAGTA
      AAACAACAAGGAAAGAGAAAAACACTCTGTCCCAGAGTGAGACAACGGGTCCCACCTCAT 2907 tthIII1, 2941  AGTGGTGTGATCATGGCTCACTGCAGCCTCAACCTCCTGGGCTCAAGCAATCCTCCCACC
      TCACCACACTAGTACCGAGTGACGTCGGAGTTGGAGGACCCGAGTTCGTTAGGAGGGTGG 2948 bcl1,  2961 pst1, 3001  TCAGCCTCCCAAGTAGTGGGACTACAGGCATGCACCATCATGCCAGGCTAACTTTTTTAT
      AGTCGGAGGGTTCATCACCCTGATGTCCGTACGTGGTAGTACGGTCCGATTGAAAAAATA 3028 sph1, 3061  TTTTTGTAGAGACAGGGTCTTGCTTTGTTGCCCAGGCTGGTCTTGAACTCCAAGCTCAAG
      AAAAACATCTCTGTCCCAGAACGAAACAACGGGTCCGACCAGAACTTGAGGTTCGAGTTC 3071 tthIII1, 3121  CAATCCTCCAACCTCAGCTTCCCAAAGTGCTGGGATTACCAGTATGAGCCACTGCACCTG
      GTTAGGAGGTTGGAGTCGAAGGGTTTCACGACCCTAATGGTCATACTCGGTGACGTGGAC 3142 bstXI, 3181  GCCTTGTTGTTCCTTTCTTCCTTTTATCTTGTAGTATCTTGATCCTTTTTGCTTATTATT
      CGGAACAACAAGGAAAGAAGGAAAATAGAACATCATAGAACTAGGAAAAACGAATAATAA 3196 mbo11, 3241  TATCATTGAGGTGAGTTTGTTCTAAATAAACTTTTCGCAGAAAGTTTATGTAGATATATT
      ATAGTAACTCCACTCAAACAAGATTTATTTGAAAAGCGTCTTTCAAATACATCTATATAA 3301  AATATCAATGAGGCATTAGGAGTGAGTTTTAGATTAGCAGGAATTCTCTTATGAAAGGTA    EcoRI #79
      TTATAGTTACTCCGTAATCCTCACTCAAAATCTAATCGTCCTTAAGAGAATACTTTCCAT 3341 ecor1, 3361  TTGATTGTATGTGTGAGTTTTCAGCCTTTACTTCTCTCCAGCCCATCAAGATCAAAGCTG
      AACTAACATACACACTCAAAAGTCGGAAATGAAGAGAGGTCGGGTAGTTCTAGTTTCGAC 3418 pst1, 3421  CAGAGTTGTTTACATTTCAGAATTTCTTTCCTCCCCTCCCCACCTTGCAAAACAGACTTA
      GTCTCAACAAATGTAAAGTCTTAAAGAAAGGAGGGGAGGGGTGGAACGTTTTGTCTGAAT 3481  CAGTGCAAAAATGACTTGTCAATGTGATTCTTTCTTCTGGTCCCATCTTTCCTACCTTTT
      GTCACGTTTTTACTGAACAGTTACACTAAGAAGAAGACCAGGGTAGAAAGGATGGAAAA 3513 mbo11, 3541  GAGACTTGTGTTGAAAGGAGTCCAGTAAAACCACCGATGCTAGCTTGTATACCCTGATCC
      CTCTGAACACAACTTTCCTCAGGTCATTTGGTGGCTACGATCGAACATATGGGACTAGG 3601  CATTGTTATAATGAATGACTGACTGTTTTTCATATCAAAGTATAATACTTGCACCTTGAT
      GTAACAATATTACTTACTGACTGACAAAAAGTATAGTTTCATATTATGAACGTGGAACTA 3661  AGAAGAAAGAAACAAGGCCAGGCACAGTGGTTCATGCCTGTAATCCCAGCACTTTGGGAG
      TCTTCTTTCTTTGTTCCGGTCCGTGTCACCAAGTACGGACATTAGGGTCGTGAAACCCTC 3662 mbo11,  3706 bstXI, 3721  GCTGAAGTAGGAGGAATAATTAGACTTTGATATTAAAAATGGGGAAGATATGGCGGTATA
      CGACTTCATCCTCCTTATTAATCTGAAACTATAATTTTTACCCCTTCTATACCGCCATAT 3764 mbo11, 3781  AGATATGAGGAAGTATGTCTTCTTGGACTTTTCTGAAATCTGCCAGCCATGAGCATCCAC
      TCTATACTCCTTCATACAGAAGAACCTGAAAAGACTTTAGACGGTCGGTACTCGTAGGTG 3798 mbo11, 3841  TCTTTTTTATCTTTTGATACCTGTTTTATATTAACTATACTTCTATTTTGTGGTTTCATGG
      AGAAAAATAGAAAACTATGGACAAAATATAATTGATATGAAGATAAAACACCAAAGTACC 3901  CTTCAGATATCTTCCAGCTTAATTGTACTCTGTCTTTAATTATTTGCAGCAATTTCTGAA
      GAAGTCTATAGAAGGTCGAATTAACATGAGACAGAAATTAATAAACGTCGTTAAAGACTT 3906 ecor5,  3910 mbo11, 3961  AGGAGCAAGAAGAAAGGCCAGCCCTTTCTTCACTACCTTAAAAACTGGTCATCTTTTGAA
      TCCTCGTTCTTCTTTCCGGTCGGGAAAGAAGTGATGGAATTTTTGACCAGTAGAAAACTT 3969 mbo11,  3987 mbo11,
```

```
4021 ACCCCATGAAAGGCACAGTGGGTGACCATCTACATCAGGAGTGGGCAAACTATGGCCCTT
     TGGGGTACTTTCCGTGTCACCCACTGGTAGATGTAGTCCTCACCCGTTTGATACCGGGAA 4041 bstE2, 4081 GGGTAGTCTGGTCTCTGTCCGTTTTTGTAAGGTTTTATTGGAACCCATACACACACAAAC
     CCCATCAGACCAGAGACAGGCAAAAACATTCCAAAATAACCTTGGGTATGTGTGTGTTTG 4141 TGATCATCTCTTGTTATGTGTTAAGTTTTCTTATAATTATTCTTTTCTATTTCATCCAGC
     ACTAGTAGAGAACAATACACAATTCAAAAGAATATTAATAAGAAAAGATAAAGTAGGTCG 4141 bcl1, 4197 pvu11, 4201 TGAATTACCATTTCACCTTGTGTATGCCCTTTCCAGTCTTAAATTATAGAAGCTATGTCT
     ACTTAATGGTAAAGTGGAACACATACGGGAAAGGTCAGAATTTAATATCTTCGATACAGA 4261 TTGTGGTTTTAAATTATGGAAGCTGTGCCTTCTTGTGTTTTAGTATGGCAAGATATTTGT
     AACACCAAAATTTAATACCTTCGACACGGAAGAACACAAAATCATACCGTTCTATAAACA 4268 aha111, 4321 TCTTACTTTTCCTCTAGAATCTGCAGTGGATTACTTTCAGAAGTAGGTATTGCCTCTAAG
     AGAATGAAAAGGAGATCTTAGACGTCACCTAATGAAAGTCTTCATCCATAACGGAGATTC 4333 xba1, 4341 pst1, 4381 TTTCCTGACTTCTGTTTCCTTCTCCCTGTTCTGTAGTATATTTATAGATTGCATGTTTTC
     AAAGGACTGAAGACAAAGGAAGAGGGACAAGACATCATATAAATATCTAACGTACAAAAG 4441 TCGTCCTTAAACAAGGTACAAATATGTTCTGATCAAGGTTTGCTAGCCGAGAGGATAAGT
     AGCAGGAATTTGTTCCATGTTTATACAAGACTAGTTCCAAACGATCGGCTCTCCTATTCA 4470 bcl1, 4501 GGCTTGCTCTTAGCCTAACTCTCTGTCTACTTAATGGATGTCGAATTCCCTTCTCAACTC      EcoRI #70-3
     CCGAACGAGAATCGGATTGAGAGACAGATGAATTACCTACAGCTTAAGGGAAGAGTTGAG 4561 AACAGCTAGTAACTAGTTCCAAGATCGGATAATAGCTTACAGAATTAATTAGTTCAGTGA
     TTGTCGATCATTGATCAAGGTTCTAGCCTATTATCGAATGTCTTAATTAATCAAGTCACT 4621 AAGCCCTGGTTTGATCACAGAGGCAGGAGACTGATCTATATATTTGTAGTGCTGACTAGA
     TTCGGGACCAAACTAGTGTCTCCGTCCTCTGACTAGATATATAAACATCACGACTGATCT 4632 bcl1, 4681 CCCCAACTTGGCCAGATAGCTTATACCTATGTCAGAAGTTGGAGGAGGAGATTGACAGCT
     GGGGTTGAACCGGTCTATCGAATATGGATACAGTCTTCAACCTCCTCCTCTAACTGTCGA 4689 bal1, 4736 pvu11, 4741 GAGGTGTCTCCAAGGGAATTACAATTATTTTCATTTTCTTTGTGTCTGTAATTATGTCTC
     CTCCACAGAGGTTCCCTTAATGTTAATAAAAGTAAAAGAAACACAGACATTAATACAGAG 4801 TTTTCTTACTTCAAATTTTGTATATGTGAAATTTCTTAATTTTTATTTGGTTATTTATTT
     AAAAGAATGAAGTTTAAAACATATACACTTTAAAGAATTAAAAATAAACCAATAAATAAA 4861 TATTGACTTTTTCATCAAACAACCAACTCTAAGTTCTTGGATTGAAATTTATGAATTAAT
     ATAACTGAAAAAGTAGTTTGTTGGTTGAGATTCAAGAACCTAACTTTAAATACTTAATTA 4921 TATAATGTTTTAAATTTACCATTAGTCACACATACAATACAAAAAGATATTTTCATTACA
     ATATTACAAAATTTAAATGGTAATCAGTGTGTATGTTATGTTTTTCTATAAAAGTAATGT 4929 aha111, 4981 AAATTTTAACCCAAGCCATTAAAACTAAACTCCAGCTTGGTCACCATTCCTAATACCAGG
     TTTAAAATTGGGTTCGGTAATTTTGATTTGAGGTCGAACCAGTGGTAAGGATTATGGTCC 5019 bstE2, 5041 CCCCTCTCAGAGGAGGGTAAATAAAAGTCCATTTTGGTAACTAGTTTGACGAGAATCTCT
     GGGGAGAGTCTCCTCCCATTTATTTTCAGGTAAAACCATTGATCAAACTGCTCTTAGAGA 5101 AATTGTTTCCCTGTTTTTCTTATAATGTCTGCCTTTGAATTATCCTCTTTTTTTCAAGAG
     TTAACAAAGGGACAAAAAGAATATTACAGACGGAAACTTAATAGGAGAAAAAAAGTTCTC 5161 TTCCATCATATAATGTATTCCTTTTTGCTTACAGATTGACCTCCTAGAGGCATGCATCCC
     AAGGTAGTATATTACATAAGGAAAAACGAATGTCTAACTGGAGGATCTCCGTACGTAGGG 5210 sph1, 5212 ava3, 5221 CCTGCTCCAGTCTGAGCTGGTTCTCTCTAGGCCTGAGGCTCAGTTATCAACTTGGGACTT
     GGACGAGGTCAGACTCGACCAAGAGAGATCCGGACTCCGAGTCAATAGTTGAACCCTGAA 5222 tthIII1, 5249 stu1, 5252 mstII, 5281 TTATTTACCCTCCCTCAGGATAGGTACCTGGTTCTTGGATACCAGGTCTTACTCTTGTTT
     AATAAATGGGAGGGAGTCCTATCCATGGACCAAGAACCTATGGTCCAGAATGAGAACAAA 5293 mstII, 5303 kpn1, 5341 GAGATACTCCTTTATTTTGGTGGCAAACATTCCATAATCACTTCCTGATAATGGTGACAT
     CTCTATGAGGAAATAAAACCACCGTTTGTAAGGTATTAGTGAAGGACTATTACCACTGTA 5401 TTGAGGTAGATTTTCTGAGTCTTTATATGTTAGAATATGTTTTTATTCTCCTTTGCCACT
     AACTCCATCTAAAAGACTCAGAAATATACAATCTTATACAAAAATAAGAGGAAACGGTGA
```

```
5461  TGATTGATAATTTGGCTGCACATAGAATGTAAGCATTCACAGGGCTTTTGGGAGCAGCTT
      ACTAACTATTAAACCGACGTGTATCTTACATTCGTAAGTGTCCCGAAAACCCTCGTCGAA

5521  CCCTTGAGAAGAAGGTGGATGCAGTTAAGATCTTCCCTGAAAAGACTGTGTGAAATGACA
      GGGAACTCTTCTTCCACCTACGTCAATTCTAGAAGGGACTTTTCTGACACACTTTACTGT 5528 mboII, 5548 bglII, 5551 mboII, 5581  AGGCTATTGAGGTACCCAACGGGTAGCTTGGTAAAGGTGTATCTTGTCTCTTATGTTTAT
      TCCGATAACTCCATGGGTTGCCCATCGAACCATTTCCACATAGAACAGAGAATACAAATA 5571 kpnI, 5639 ava3, 5641  GCATCTACTTTACCACCATGTAATTAGCCTATTATAACTTGTTGCATTCCTTCACTCAGC
      CGTAGATGAAATGGTGGTACATTAATCGGATAATATTGAACAACGTAAGGAAGTGAGTCG 5701  TAATCTTGTTCATGGTAGAAATTAATATTGCTAGTACCATGGTAGAATTTTATATTAGCT
      ATTAGAACAAGTACCATCTTTAATTATAACGATCATGGTACCATCTTAAAATATAATCGA 5737 ncoI, 5761  GGATCCTAGACCTAAATGCTCCTTCCTTGTGCTTACATATTCTGCAAGTGGGTGACAGTG
      CCTAGGATCTGGATTTACGAGGAAGGAACACGAATGTATAAGACGTTCACCCACTGTCAC 5761 bamhI binI, 5821  GATGCTAGGTATTGTGTTATGTGATTTCAATGTATTATATGATGGGGTAGATACTATTAG
      CTACGATCCATAACACAATACACTAAAGTTACATAATATACTACCCCATCTATGATAATC 5881  CCTCATTTGAAAATTAGAAACCTATTGTTCAGAAAGTTTAAGTGACTTTCTCAAAGTCAC
      GGAGTAAACTTTTAATCTTTGGATAACAAGTCTTTCAAATTCACTGAAAGAGTTTCAGTG 5941  ACAGCTGGTAAATGGTAGAACTGGGATTTGAATCCAGGCAATCTGATGGATTTAAGAGGA
      TGTCGACCATTTACCATCTTGACCCTAAACTTAGGTCCGTTAGACTACCTAAATTCTCCT 5942 pvuII, 6001  ACCTGTGCCACTATGTGATATAGCAATAACATCTAGCCAATATAAATACTTTCCTGAATT
      TGGACACGGTGATACACTATATCGTTATTGTAGATCGGTTATATTTATGAAAGGACTTAA 6061  AAATCACTGTCATATTCAGAGAGTTCTGTGTCACTATTAAGACCCTCCATTATTGTGTAT
      TTTAGTGACAGTATAAGTCTCTCAAGACACAGTGATAATTCTGGGAGGTAATAACACATA 6063 ecopDXI, 6121  ATTAATTACATTTCCCTATTTTAATCCCAATATCTATTCATTTTTATCACAGTCCTTTCT
      TAATTAATGTAAAGGGATAAAATTAGGGTTATAGATAAGTAAAAATAGTGTCAGGAAAGA 6181  TATGGTCACAAACAGGCATAGTACAACAGCAGCAATGCAAAAACCACTTTTATATTACAT
      ATACCAGTGTTTGTCCGTATCATGTTGTCGTCGTTACGTTTTTGGTGAAAATATAATGTA 6241  GTTCCAGGGATTTAACCCAATGACCTGTGATATAATGATACTGACTAGTATTTTTTCATT
      CAAGGTCCCTAAATTGGGTTACTGGACACTATATTACTATGACTGATCATAAAAAAGTAA 6301  TATCTGGGAATGGGAGAGAACCTCTAACAGAACGTTTTAGAATCTGTGTTATGAGTAACC
      ATAGACCCTTACCCTCTCTTGGAGATTGTCTTGCAAAATCTTAGACACAATACTCATTGG 6361  AGAGTCTTAGTTCTTCCTCATCTCCAGGTCTATGGATTCTGGGGTGCCACAACTCAGACT
      TCTCAGAATCAAGAAGGAGTAGAGGTCCAGATACCTAAGACCCCACGGTGTTGAGTCTGA 6372 mboII, 6384 bstXI, 6421  TTCGGAAGCAGAGGCATGACCGCCTTACTGAAGGTTTCTAGTTGTGACAAGAACACTGGT
      AAGCCTTCGTCTCCGTACTGGCGGAATGACTTCCAAAGATCAACACTGTTCTTGTGACCA 6481  GATTATTACGAGGACAGTTATGAAGATATTTCAGCATACTTGCTGAGTAAAAACAATGCC
      CTAATAATGCTCCTGTCAATACTTCTATAAAGTCGTATGAACGACTCATTTTTGTTACGG 6502 mboII, 6541  ATTGAACCAAGAAGCTTCTCCCAGAATTCAAGACACCCTAGCACTAGGCAAAAGCAATTT    4.3kbEcoRI
      TAACTTGGTTCTTCGAAGAGGGTCTTAAGTTCTGTGGGATCGTGATCCGTTTTCGTTAAA 6552 hindIII, 6564 ecorI, 6601  AATGCCACCACAATTCCAGAAAATGACATAGAGAAGACTGACCCTTGGTTTGCACACAGA
      TTACGGTGGTGTTAAGGTCTTTTACTGTATCTCTTCTGACTGGGAACCAAACGTGTGTCT 6633 mboII, 6661  ACACCTATGCCTAAAATACAAAATGTCTCCTCTAGTGATTTGTTGATGCTCTTGCGACAG
      TGTGGATACGGATTTTATGTTTTACAGAGGAGATCACTAAACAACTACGAGAACGCTGTC 6716 tthIII1, 6721  AGTCCTACTCCACATGGGCTATCCTTATCTGATCTCCAAGAAGCCAAATATGAGACTTTT
      TCAGGATGAGGTGTACCCGATAGGAATAGACTAGAGGTTCTTCGGTTTATACTCTGAAAA 6781  TCTGATGATCCATCACCTGGAGCAATAGACAGTAATAACAGCCTGTCTGAAATGACACAC
      AGACTACTAGGTAGTGGACCTCGTTATCTGTCATTATTGTCGGACAGACTTTACTGTGTG
```

6841 TTCAGGCCACAGCTCCATCACAGTGGGGACATGGTATTTACCCCTGAGTCAGGCCTCCAA
     AAGTCCGGTGTCGAGGTAGTGTCACCCCTGTACCATAAATGGGGACTCAGTCCGGAGGTT 6855 bstXI, 6884 tthIII1, 6891 stu1, 6901 TTAAGATTAAATGAGAAACTGGGGACAACTGCAGCAACAGAGTTGAAGAAACTTGATTTC
     AATTCTAATTTACTCTTTGACCCCTGTTGACGTCGTTGTCTCAACTTCTTTGAACTAAAG 6929 pst1, 6945 mbo11, 6961 AAAGTTTCTAGTACATCAAATAATCTGATTTCAACAATTCCATCAGACAATTTGGCAGCA
     TTTCAAAGATCATGTAGTTTATTAGACTAAAGTTGTTAAGGTAGTCTGTTAAACCGTCGT 7021 GGTACTGATAATACAAGTTCCTTAGGACCCCCAAGTATGCCAGTTCATTATGATAGTCAA
     CCATGACTATTATGTTCAAGGAATCCTGGGGGTTCATACGGTCAAGTAATACTATCAGTT 7040 mstII, 7081 TTAGATACCACTCTATTTGGCAAAAAGTCATCTCCCCTTACTGAGTCTGGTGGACCTCTG
     AATCTATGGTGAGATAAACCGTTTTTCAGTAGAGGGGAATGACTCAGACCACCTGGAGAC 7141 AGCTTGAGTGAAGAAAATAATGATTCAAAGTTGTTAGAATCAGGTTTAATGAATAGCCAA
     TCGAACTCACTTCTTTTATTACTAAGTTTCAACAATCTTAGTCCAAATTACTTATCGGTT 7150 mbo11, 7201 GAAAGTTCATGGGGAAAAAATGTATCGTCAACAGAGAGTGGTAGGTTATTTAAAGGGAAA
     CTTTCAAGTACCCCTTTTTTACATAGCAGTTGTCTCTCACCATCCAATAAATTTCCCTTT 7249 aha111, 7261 AGAGCTCATGGACCTGCTTTGTTGACTAAAGATAATGCCTTATTCAAAGTTAGCATCTCT
     TCTCGAGTACCTGGACGAAACAACTGATTTCTATTACGGAATAAGTTTCAATCGTAGAGA 7262 sac1, 7321 TTGTTAAAGACAAACAAAACTTCCAATAATTCAGCAACTAATAGAAAGACTCACATTGAT
     AACAATTTCTGTTTGTTTTGAAGGTTATTAAGTCGTTGATTATCTTTCTGAGTGTAACTA 7381 GGCCCATCATTATTAATTGAGAATAGTCCATCAGTCTGGCAAAATATATTAGAAAGTGAC
     CCGGGTAGTAATAATTAACTCTTATCAGGTAGTCAGACCGTTTTATATAATCTTTCACTG 7408 bstXI, 7441 ACTGAGTTTAAAAAAGTGACACCTTTGATTCATGACAGAATGCTTATGGACAAAAATGCT
     TGACTCAAATTTTTTCACTGTGGAAACTAAGTACTGTCTTACGAATACCTGTTTTTACGA 7447 aha111, 7501 ACAGCTTTGAGGCTAAATCATATGTCAAATAAAACTACTTCATCAAAAAACATGGAAATG
     TGTCGAAACTCCGATTTAGTATACAGTTTATTTTGATGAAGTAGTTTTTTGTACCTTTAC 7519 nde1, 7561 GTCCAACAGAAAAAAGAGGGCCCCATTCCACCAGATGCACAAAATCCAGATATGTCGTTC
     CAGGTTGTCTTTTTTCTCCCGGGGTAAGGTGGTCTACGTGTTTTAGGTCTATACAGCAAG 7578 apa1, 7621 TTTAAGATGCTATTCTTGCCAGAATCAGCAAGGTGGATACAAAGGACTCATGGAAAGAAC
     AAATTCTACGATAAGAACGGTCTTAGTCGTTCCACCTATGTTTCCTGAGTACCTTTCTTG 7681 TCTCTGAACTCTGGGCAAGGCCCCAGTCCAAAGCAATTAGTATCCTTAGGACCAGAAAAA
     AGAGACTTGAGACCCGTTCCGGGGTCAGGTTTCGTTAATCATAGGAATCCTGGTCTTTTT 7724 mstII, 7741 TCTGTGGAAGGTCAGAATTTCTTGTCTGAGAAAAACAAAGTGGTAGTAGGAAAGGGTGAA
     AGACACCTTCCAGTCTTAAAGAACAGACTCTTTTTGTTTCACCATCATCCTTTCCCACTT 7801 TTTACAAAGGACGTAGGACTCAAAGAGATGGTTTTTCCAAGCAGCAGAAACCTATTTCTT
     AAATGTTTCCTGCATCCTGAGTTTCTCTACCAAAAAGGTTCGTCGTCTTTGGATAAAGAA 7861 ACTAACTTGGATAATTTACATGAAAATAATACACACAATCAAGAAAAAAAAATTCAGGAA
     TGATTGAACCTATTAAATGTACTTTTATTATGTGTGTTAGTTCTTTTTTTTTAAGTCCTT 7918 mbo11, 7921 GAAATAGAAAAGAAGGAAACATTAATCCAAGAGAATGTAGTTTTGCCTCAGATACATACA
     CTTTATCTTTTCTTCCTTTGTAATTAGGTTCTCTTACATCAAAACGGAGTCTATGTATGT 7981 GTGACTGGCACTAAGAATTTCATGAAGAACCTTTTCTTACTGAGCACTAGGCAAAATGTA
     CACTGACCGTGATTCTTAAAGTACTTCTTGGAAAAGAATGACTCGTGATCCGTTTTACAT 8004 mbo11, 8007 xmn1, 8041 TAAGGTTCATATGACGGGGCATATGCTCCAGTACTTCAAGATTTTAGGTCATTAAATGAT
     ATTCCAAGTATACTGCCCCGTATACGAGGTCATGAAGTTCTAAAATCCAGTAATTTACTA 8048 nde1, 8060 nde1, 8070 sca1,

```
8101 TCAACAAATAGAACAAAGAAACACACAGCTCATTTCTCAAAAAAAGGGGAGGAAGAAAAC
     AGTTGTTTATCTTGTTTCTTTGTGTGTCGAGTAAAGAGTTTTTTTCCCCTCCTTCTTTTG 8152 mbo11, 8161 TTGGAAGGCTTGGGAAATCAAACCAAGCAAATTGTAGAGAAATATGCATGCACCACAAGG
     AACCTTCCGAACCCTTTAGTTTGGTTCGTTTAACATCTCTTTATACGTACGTGGTGTTCC 8204 ava3, 8206 sph1, 8220 ecor5, 8221 ATATCTCCTAATACAAGCCAGCAGAATTTTGTCACGCAACGTAGTAAGAGAGCTTTGAAA
     TATAGAGGATTATGTTCGGTCGTCTTAAAACAGTGCGTTGCATCATTCTCTCGAAACTTT 8277 xmn1, 8281 CAATTCAGACTCCCACTAGAAGAAACAGAACTTGAAAAAAGGATAATTGTGGATGACACC
     GTTAAGTCTGAGGGTGATCTTCTTTGTCTTGAACTTTTTTCCTATTAACACCTACTGTGG 8299 mbo11, 8341 TCAACCCAGTGGTCCAAAAACATGAAACATTTGACCCCGAGCACCCTCACACAGATAGAC
     AGTTGGGTCACCAGGTTTTTGTACTTTGTAAACTGGGGCTCGTGGGAGTGTGTCTATCTG 8376 ava1, 8401 TACAATGAGAAGGAGAAAGGGGCCATTACTCAGTCTCCCTTATCAGATTGCCTTACGAGG
     ATGTTACTCTTCCTCTTTCCCCGGTAATGAGTCAGAGGGAATAGTCTAACGGAATGCTCC 8461 AGTCATAGCATCCCTCAAGCAAATAGATCTCCATTACCCATTGCAAAGGTATCATCATTT
     TCAGTATCGTAGGGAGTTCGTTTATCTAGAGGTAATGGGTAACGTTTCCATAGTAGTAAA 8485 bgl11, 8521 CCATCTATTAGACCTATATATCTGACCAGGGTCCTATTCCAAGACAACTCTTCTCATCTT
     GGTAGATAATCTGGATATATAGACTGGTCCCAGGATAAGGTTCTGTTGAGAAGAGTAGAA 8569 mbo11, 8577 mbo11, 8581 CCAGCAGCATCTTATAGAAAGAAAGATTCTGGGGTCCAAGAAAGCAGTCATTTCTTACAA
     GGTCGTCGTAGAATATCTTTCTTTCTAAGACCCCAGGTTCTTTCGTCAGTAAAGAATGTT 8641 GGAGCCAAAAAAAATAACCTTTCTTTAGCCATTCTAACCTTGGAGATGACTGGTGATCAA
     CCTCGGTTTTTTTATTGGAAAGAAATCGGTAAGATTGGAACCTCTACTGACCACTAGTT 8694 bcl1, 8701 AGAGAGGTTGGCTCCCTGGGGACAAGTGCCACAAATTCAGTCACATACAAGAAAGTTGAG
     TCTCTCCAACCGAGGGACCCCTGTTCACGGTGTTTAAGTCAGTGTATGTTCTTTCAACTC 8761 AACACTGTTCTCCCGAAACCAGACTTGCCCAAAACATCTGGCAAAGTTGAATTGCTTCCA
     TTGTGACAAGAGGGCTTTGGTCTGAACGGGTTTTGTAGACCGTTTCAACTTAACGAAGGT 8809 xmn1, 8821 AAAGTTCACATTTATCAGAAGGACCTATTCCCTACGGAAACTAGCAATGGGTCTCCTGGC
     TTTCAAGTGTAAATAGTCTTCCTGGATAAGGGATGCCTTTGATCGTTACCCAGAGGACCG 8877 bal1, 8881 CATCTGGATCTCGTGGAAGGGAGCCTTCTTCAGGGAACAGAGGGAGCGATTAAGTGGAAT
     GTAGACCTAGAGCACCTTCCCTCGGAAGAAGTCCCTTGTCTCCCTCGCTAATTCACCTTA 8886 binI, 8907 mbo11, 8941 GAAGCAAACAGACCTGGAAAAGTTCCCTTTCTGAGAGTAGCAACAGAAAGCTCTGCAAAG
     CTTCGTTTGTCTGGACCTTTTCAAGGGAAAGACTCTCATCGTTGTCTTTCGAGACGTTTC 9001 ACTCCCTCCAAGCTATTGGATCCTCTTGCTTGGGATAACCACTATGGTACTCAGATACCA
     TGAGGGAGGTTCGATAACCTAGGAGAACGAACCCTATTGGTGATACCATGAGTCTATGGT 9008 bstXI, 9018 bamh1 binI, 9061 AAAGAAGAGTGGAAATCCCAAGAGAAGTCACCAGAAAAAACAGCTTTTAAGAAAAAGGAT
     TTTCTTCTCACCTTTAGGGTTCTCTTCAGTGGTCTTTTTTGTCGAAAATTCTTTTTCCTA 9064 mbo11, 9121 ACCATTTTGTCCCTGAACGCTTGTGAAAAGCAATCATGCAATAGCAGCAATAAATGAGGCA
     TGGTAAAACAGGGACTTGCGAACACTTTCGTTAGTACGTTATCGTCGTTATTTACTCCCT 9181 CAAAATAAGCCCGAAATAGAAGTCACCTGGGCAAAGCAAGGTAGGACTGAAAGGCTGTGC
     GTTTTATTCGGGCTTTATCTTCAGTGGACCCGTTTCGTTCCATCCTGACTTTCCGACACG 9241 TCTCAAAACCCACCAGTCTTGAAACGCCATCAACGGGAAATAACTCGTACTACTCTTCAG
     AGAGTTTTGGGTGGTCAGAACTTTGCGGTAGTTGCCCTTTATTGAGCATGATGAGAAGTC 9294 mbo11, 9301 TCAGATCAAGAGGAAATTGACTATGATGATACCATATCAGTTGAAATGAAGAAGGAAGAT
     AGTCTAGTTCTCCTTTAACTGATACTACTATGGTATAGTCAACTTTACTTCTTCCTTCTA 9348 mbo11, 9355 mbo11, 9361 TTTGACATTTATGATGAGGATGAAAATCAGAGCCCCCGCAGCTTTTCAAAAGAAAACACGA
     AAACTGTAAATACTACTCCTACTTTTAGTCTCGGGGGCGTCGAAAGTTTTCTTTTGTGCT
```

```
10861  CTCCAAAGAAGCTTTTATCTCTATTATTTCATAAGAACTACATTTTCAAGGTCATTATTG
       GAGGTTTCTTCGAAAATAGAGATAATAAAGTATTCTTGATGTAAAAGTTCCAGTAATAAC 10869 hind111, 10921  ATCTTTACATTACTGATTACTAGCCCTCATCTTATTTGAATTCTCAGTAGTATTTGAGAG    EcoRI #76
       TAGAAATGTAATGACTAATGATCGGGAGTAGAATAAACTTAAGAGTCATCATAAACTCTC 10958 ecor1, 10981  GTGATTACTCCATCGTTGATACAGGTTCTCACTTGGTTTCTCTAACACCACTTTTCTTCA
       CACTAATGAGGTAGCAACTATGTCCAAGAGTGAACCAAAGAGATTGTGGTGAAAAGAAGT 11035 mbo11, 11041  CTTTTCTACTAAACTTACTGCCAATCTTTGTCAACTTTGCGAGTCCTTCTTCATCCCCCT
       GAAAAGATGATTTGAATGACGGTTAGAAACAGTTGAAACGCTCAGGAAGAAGTAGGGGGA 11088 mbo11, 11101  AATCTTTAAAGGTTAGAGTGCTCCAGGGATTAGTTCTCCAACTTCTTCTTTATTCTATTT
       TTAGAAATTTCCAATCTCACGAGGTCCCTAATCAAGAGGTTGAAGAAGAAATAAGATAAA 11105 aha111, 11144 mbo11, 11161  ATACTCACTCTGTGACGACATTGTTTAGCCTCATGATTTTAAGTACTATCTATCTGCAGA
       TATGAGTGAGACACTGCTGTAACAAATCGGAGTACTAAAATTCATGATAGATAGACGTCT 11202 sca1, 11214 pst1, 11221  TAATTCCAGTTGAATATCTGGAGATATTCTCAGATCTCTCTCCTGAAGTCAAAATTTACA
       ATTAAGGTCAACTTATAGACCTCTATAAGAGTCTAGAGAGAGGACTTCAGTTTTAAATGT 11252 bgl11, 11281  TATCAACTCCCTACCTTAACATGCACACAATTAGACTCTTAATTCCTGCCCCTTCCCAAA
       ATAGTTGAGGGATGGAATTGTACGTGTGTTAATCTGAGAATTAAGGACGGGGAAGGGTTT 11341  ACCTGCTGATTGCTCAGCCTTCTCCATGGCAATCAAAAACCATTCCTGGCCGGGCATGGT
       TGGACGACTAACGAGTCGGAAGAGGTACCGTTAGTTTTTGGTAAGGACCGGCCCGTACCA 11364 nco1, 11401  GGCTCACTCCTGTAACCCCAGCACTTGGGGAAGCTGAGGCAGGTGGATTGGTTGAGCCCC
       CCGAGTGAGGACATTGGGGTCGTGAACCCCTTCGACTCCGTCCACCTAACCAACTCGGGG 11434 tth111, 11461  AGAGTTCAAGATCAGCCTGGGCAACATGGCAAAACCTCATCTCTATTAAAAATACAAAAA
       TCTCAAGTTCTAGTCGGACCCGTTGTACCGTTTTGGAGTAGAGATAATTTTTATGTTTTT 11521  TTAGCCAGGCGTGGTGGTGCACACCTGCAGTCCCAGCTACTCAGGAGGCTGAGGCACGAG
       AATCGGTCCGCACCACCACGTGTGGACGTCAGGGTCGATGAGTCCTCCGACTCCGTGCTC 11545 pst1, 11581  AATCGCTTGAACTGGGGAGACGGAGGTTGCAGTGAGCTGAGATGGCCTCACTGCACTCCA
       TTAGCGAACTTGACCCCTCTGCCTCCAACGTCACTCGACTCTACCGGAGTGACGTGAGGT 11641  GCCTGGGCAACAGAGTCAGACTTGATCTCAAAAAAATAAATAAGTAAAACCATTCCCTAT
       CGGACCCGTTGTCTCAGTCTGAACTAGAGTTTTTTTATTTATTCATTTTGGTAAGGGATA 11701  TTCAGTTATTCAGTCACAGATCTTGAAGTTTTCCAACTCTTTTTTTCTTACATTAACATC
       AAGTCAATAAGTCAGTGTCTAGAACTTCAAAAGGTTGAGAAAAAAGAATGTAATTGTAG 11718 bgl11, 11761  TAATCTGTAAAGGATCCTGTATTAGTCCATTTTCACACTGCTAATAAAGACATACCTGAG
       ATTAGACATTTCCTAGGACATAATCAGGTAAAAGTGTGACGATTATTTCTGTATGGACTC 11772 bamh1 bin1, 11821  ACTGGGCAATTTACAAAAGAAAGAAGTTTAATGGACTCACAGTTCCACATGGCTGGGGAG
       TGACCCGTTAAATGTTTTCTTTCTTCAAATTACCTGAGTGTCAAGGTGTACCGACCCCTC 11865 bstXI, 11879 stu1, 11881  GCCTCACAATCATGGCAGAAGGCAGGGAGGAGCAAGTTATATCTCACATGATGGCACAGG
       CGGAGTGTTAGTACCGTCTTCCGTCCCTCCTCGTTCAATATAGAGTGTACTACCGTGTCC 11941  CAAAGAGAGAGAGCTTGTGCAGGGAAACTCCTCTTTTTAAAACCATCAGATCTTGTGAGA
       GTTTCTCTCTCTCGAACACGTCCCTTTGAGGAGAAAAATTTTGGTAGTCTAGAACACTCT 11976 aha111, 11988 bgl11, 12001  CTTATTCACTATCATGAGAACAGCAAGGGAAGGACCTACTGCCATGATTCAGTTACCTCC
       GAATAAGTGATAGTACTCTTGTCGTTCCCTTCCTGGATGACGGTACTAAGTCAATGGAGG 12061  TATCAGGTCCCTCCCACAGAACATGGGAATTCAAGATGAGATTTGGGTAGGGACACAGCC    EcoRI #17
       ATAGTCCAGGGAGGGTGTCTTGTACCCTTAAGTTCTACTCTAAACCCATCCCTGTGTCGG 12087 ecor1,
```

```
12121  AAACCATATCATTCCACCCCATCCCCTCCCAAATCTCGTGTCCTCACATTTCAAAACCAA
       TTTGGTATAGTAAGGTGGGGTAGGGGAGGGTTTAGAGCACAGGAGTGTAAAGTTTTGGTT

12181  TCATGCCTTCCCAACAGTCCCCCAAAGTCATAACACATTTCAGCATTAACTCAAAAGTCC
       AGTACGGAAGGGTTGTCAGGGGGTTTCAGTATTGTGTAAAGTCGTAATTGAGTTTTCAGG

12241  ACAGTCCAATGTCTCATCTAAGACAAGGCAAGTCCCTTCCACCTATGAGCATGTAAAGTC
       TGTCAGGTTACAGAGTAGATTCTGTTCCGTTCAGGGAAGGTGGATACTCGTACATTTCAG

12301  AAAAGCAAGTTAGTTACTTCCTAGATACAATGGGGTATAGGCATTGGGTAAATACAGCCA
       TTTTCGTTCAATCAATGAAGGATCTATGTTACCCCATATCCGTAACCCATTTATGTCGGT

12361  TTCCAAATGGGAGAAATTGGCCAAAACAAAGGGCCTACAGGCCCCATGCAAGTCTGAAAT
       AAGGTTTACCCTCTTTAACCGGTTTTGTTTCCCGGATGTCCGGGGTACGTTCAGACTTTA 12378 bal1, 12421  TCTACGGGGCAGTCAAATCTTAAATCTCTAAAGTGATCTCCTTTGACTCCATGTCTTGCA
       AGATGCCCCGTCAGTTTAGAATTTAGAGATTTCACTAGAGGAAACTGAGGTACAGAACGT 12481  TCTGAGTCATGCTGATGCAAGAGGTGGGTGCCCATGGTCTTGGGCAGCTCCACCCCTGTG
       AGACTCAGTACGACTACGTTCTCCACCCACGGGTACCAGAACCCGTCGAGGTGGGGACAC 12512 bstXI ncoI, 12530 bstXI, 12541  GCTTTGCAGGGTACAGCCTCCCTTGTGTCTGCCTTCATGGGCTGGCATTTTCTGTAGCTT
       CGAAACGTCCCATGTCGGAGGGAACACAGACGGAAGTACCCGACCGTAAAAGACATCGAA 12601  TTCCAGATGCTGGTGCAAGTTTCTGATGGATCTACCATTCCGGGGTCTGGAGGACGGTGG
       AAGGTCTACGACCACGTTCAAAGACTACCTAGATGGTAAGGCCCCAGACCTCCTGCCACC 12628 binI, 12661  CCCTCTTCTCACAGCTCCACTAGGTGGTACCCCAGTAGGGACTCTGTGTGGGTGCCCTGA
       GGGAGAAGAGTGTCGAGGTGATCCACCATGGGGTCATCCCTGAGACACACCCACGGGACT 12664 mboII, 12686 kpnI, 12721  GCCCACATTTCCCTTCTGCACTGCCCTAGCAGAGTTTCTACATGAAGGCCCACCCCCGCA
       CGGGTGTAAAGGGAAGACGTGACGGGATCGTCTCAAAGATGTACTTCCGGGTGGGGGCGT 12781  GCAAACTTCTGCCTGGGCATCCAGGCACTTCCATTAATTTCTAAACAACAAAGCATTCAA
       CGTTTGAAGACGGACCCGTAGGTCCGTGAAGGTAATTAAAGATTTGTTGTTTCGTAAGTT 12841  GAGGCGACTTGGGTGCTATTAAGGGCATTCAGTTTCATAAGGGAAGCAGAGCATAAAAGT
       CTCCGCTGAACCCACGATAATTCCCGTAAGTCAAAGTATTCCCTTCGTCTCGTATTTTCA 12901  TTGGAAAATTTGCAGCCTGATAATGTTAGAGAAAAGCAAATCCCATTTTCTGAGGAGAAA
       AACCTTTTAAACGTCGGACTATTACAATCTCTTTTCGTTTAGGGTAAAAGACTCCTCTTT 12961  TTCAAGCAGGCTGCAGAAATTTGCATAAGTAATGAGGAGCCGAATGTTAATCCCAAGACA
       AAGTTCGTCCGACGTCTTTAAACGTATTCATTACTCCTCGGCTTACAATTAGGGTTCTGT 12971 pst1, 13013 bstXI, 13021  ATGGGGAAAATGTCTCCAGGGCATGTCAGAGGTCTTCACACCAGCCCCTCCCATCACCGG
       TACCCCTTTTACAGAGGTCCCGTACAGTCTCCAGAAGTGTGGTCGGGGAGGGTAGTGGCC 13053 mboII, 13081  CCCAGAGGCCTAAGAGGAAAAAGTTGTTTCATGGGCTGGGCCCAGGATCCCCATGCTGTG
       GGGTCTCCGGATTCTCCTTTTTCAACAAAGTACCCGACCCGGGTCCTAGGGGTACGACAC 13086 stuI, 13118 apa1, 13125 bamh1 binI, 13141  TGCAGCCTAGGGAGTCGGTGCCTTGTGTCCCAGCCGCTACAGCCATGGCTGAAAGGGGTC
       ACGTCGGATCCCTCAGCCACGGAACACAGGGTCGGCGATGTCGGTACCGACTTTCCCCAG 13146 avr2, 13183 ncoI, 13201  AATGTAGAGCTCAGGCTGTGGCTTCATAGGGTACAAGTCCCAAGCCTTGGCAGCTTCCAC
       TTACATCTCGAGTCCGACACCGAAGTATCCCATGTTCAGGGTTCGGAACCGTCGAAGGTG 13207 sacI, 13261  ATGATGTTGAGCCTGCGAGTGCACAGAAGTCAAGAACTGGGGTTTGGGAACTTCCGCCTA
       TACTACAACTCGGACGCTCACGTGTCTTCAGTTCTTGACCCCAAACCCTTGAAGGCGGAT 13321  GATTTCAGAAGATGTATGAAAACACCTGGATGCCTAGGCAGAAGTTTGCTGCGGGGGTGG
       CTAAAGTCTTCTACATACTTTTGTGGACCTACGGATCCGTCTTCAAACGACGCCCCCACC 13328 mboII, 13353 avr2, 13379 apa1, 13381  GCCCTCATGGAGAACCTCTGCTAGGGCAGTGCAGAAGGGAAATGTGGGCTCAGAGCACAC
       CGGGAGTACCTCTTGGAGACGATCCCGTCACGTCTTCCCTTTACACCCGAGTCTCGTGTG 13441  ACACAGAGTCCCTGCTGGGGTACCACCTAGTGGAGCTGTGAGAAGAGGACCACCGTCCTC
       TGTGTCTCAGGGACGACCCCATGGTGGATCACCTCGACACTCTTCTCCTGGTGGCAGGAG 13459 kpn1, 13482 mboII, 13501  CAGGCCCCAGAATGGTAGATACCCTAAATCATCTCTTTTCAAATTCGAAGTTCCACAAATC
       GTCCGGGGTCTTACCATCTATGGGATTTAGTAGAGAAAGTTTAAGCTTCAAGGTGTTTAG
```

```
13561  TCTAGGACAGGAGCAAAATGCCACCAGTATCTTTGCTAAAACATAACAAGAGTTACCTTT
       AGATCCTGTCCTCGTTTTACGGTGGTCATAGAAACGATTTTGTATTGTTCTCAATGGAAA

13621  GCTCCAGTTCCCAACAAGTTCCTCATCTCTATCTGAGACCACCTCAGCCTGGATTTCATT
       CGAGGTCAAGGGTTGTTCAAGGAGTAGAGATAGACTCTGGTGGAGTCGGACCTAAAGTAA

13681  GTCCATATCATTATCAGCCTTTTGGTCAAAGCCATTCAACAAGTCTCTAGAGAGTTCCAA
       CAGGTATAGTAATAGTCGGAAAACCAGTTTCGGTAAGTTGTTCAGAGATCTCTCAAGGTT 13726 xba1, 13741  ACTTTCCACATTTTCCTGTCGTCTTCTGAGCCCTCCAAACTGTTCCAACCTCTGCCTGTT
       TGAAAGGTGTAAAAGGACAGCAGAAGACTCGGGAGGTTTGACAAGGTTGGAGACGGACAA 13762 mbo11, 13801  ACCCAGTTCCAAAGTCGCTTCCACATTTTTGGGTATCTTTTCAGCAGCACCCCACTCTAC
       TGGGTCAAGGTTTCAGCGAAGGTGTAAAAACCCATAGAAAAGTCGTCGTGGGGTGAGATG 13821 bstXI, 13852 bstXI, 13861  TGGTACCAACTTACTGTATTAGTCTGTTCTCACACTGCTGATAAAGATATACCTGAGACT
       ACCATGGTTGAATGACATAATCAGACAAGAGTGTGACGACTATTTCTATATGGACTCTGA 13862 kpn1, 13921  GGGAAATTTACAAAGGAAAGAGGTTTTATGGACTTACTGTTCCACATGGCTGGGGAGGCC
       CCCTTTAAATGTTTCCTTTCTCCAAAATACCTGAATGACAAGGTGTACCGACCCCTCCGG 13962 bstXI, 13976 stu1, 13981  TCAAAATCATGGCAGAAGGCAAGGAGGAGCAAGTCTTGTCTTACATGGATGGCAGCAGGC
       AGTTTTAGTACCGTCTTCCGTTCCTCCTCGTTCAGAACAGAATGTACCTACCGTCGTCCG 14041  AAAGAAAGAAAGCTTGTGCAGGAAAACTCTTTTTTTTCTTTTCTTCTTTTTAGACAGAGA
       TTTCTTTCTTTCGAACACGTCCTTTTGAGAAAAAAAGAAAAGAAGAAAAATCTGTCTCT 14050 hind111, 14082 mbo11, 14098 bgl11, 14101  TCTTGCTCTGTCACGCAGCCTGGAGTCAGTGGCGTGAGTCTTGGCTCACTGCAACCTCCA
       AGAACGAGACAGTGCGTCCGACCTCAGTCACCGCACTCAGAACCGAGTGACGTTGGAGGT 14161  CCTCCCGGGTTCAAGTGATTCTCCTGCCTCAGCCTTCCAAGTAGCTGGTACTACAGGCAT
       GGAGGGCCCAAGTTCACTAAGAGGACGGAGTCGGAAGGTTCATCGACCATGATGTCCGTA 14164 aval smal xma1, 14184 tth111l, 14197 bstXI, 14221  GTGCCACCACATGAGATGAGATTTTGGTAGGGACACAGCCAAACCATATCATTCCCCCTG
       CACGGTGGTGTACTCTACTCTAAAACCATCCCTGTGTCGGTTTGGTATAGTAAGGGGGAC 14281  TCCCCTCCCAAATCTCATGTCCTCACATTTCAAAACCAATCATGCCTTCCCAACAGTCCC
       AGGGGAGGGTTTAGAGTACAGGAGTGTAAAGTTTTGGTTAGTACGGAAGGGTTGTCAGGG 14341  CCAAAGTCATAACTCATTTCAGCATTAACTCAAAAGTCCACAGTATTTTAGTAGAGATG
       GGTTTCAGTATTGAGTAAAGTCGTAATTGAGTTTTCAGGTGTCATAAAAATCATCTCTAC 14401  GGGTTTCACCATATTGGCCAGACTGGTCTCTAACTCCTGACCTTATGATCCGCCCGCCTT
       CCCAAAGTGGTATAACCGGTCTGACCAGAGATTGAGGACTGGAATACTAGGCGGGCGGAA 14415 bul1, 14461  GGCCTCCCAAAGCACTGGGATTACAGGTGTGAGCCACCATGCCCAGCCAAAAACTCTTCT
       CCGGAGGGTTTCGTGACCCTAATGTCCACACTCGGTGGTACGGGTCGGTTTTTGAGAAGA 14467 bstXI, 14515 mbo11, 14521  TTTTAAAACCATCAGTTCTCGATGAGACTTATTCACTATCACAAGAACAGCATAGGAAAG
       AAAATTTTGGTAGTCAAGAGCTACTCTGAATAAGTGATAGTGTTCTTGTCGTATCCTTTC 14522 aha111, 14579 bgl11, 14581  ATCTGCCCCCATGATTCAATTACCTCCCACCAGGTCCCTCCCACAACACATGGGAATTCA    EcoRI #55
       TAGACGGGGGTACTAAGTTAATGGAGGGTGGTCCAGGGAGGGTGTTGTGTACCCTTAAGT 14634 ecor1, 14641  CGATGAGATTTGGGTGGGGATCCTCTTGGCTATCATTTCAAAAAATAGTCAGGGTTGATT
       GCTACTCTAAACCCACCCCTAGGAGAACCGATAGTAAAGTTTTTTATCAGTCCCAACTAA 14658 bamh1 binI, 14701  ATGGACTTAGTATTGAATAAGATGAAAATGTACTGAAATGGAACGATGAAGATAATTGAC
       TACCTGAATCATAACTTATTCTACTTTTACATGACTTTACCTTGCTACTTCTATTAACTG 14748 mbo11, 14761  CAGGGAAAGCAGGTTACAAGCCAAGAGAGGATACAGTGTCACTTCAGATGCTATAAAAGT
       GTCCCTTTCGTCCAATGTTCGGTTCTCTCCTATGTCACAGTGAAGTCTACGATATTTTCA 14821  GATGTTTTTATTTTTGAATGTTATTTGGCTATATTTTCAAATTATCTGCACTGCATATG
       CTACAAAAATAAAAAACTTACAATAAACCGATATAAAAGTTTAATAGACGTGACGTATAC 14875 nde1,
```

14881 CACTGCTTCTGTAATAATAAAAGGGTATTAAAATAATAAAATCAAGTCTATAAATCACAC
      GTGACGAAGACATTATTATTTTCCCATAATTTTATTATTTTAGTTCAGATATTTAGTGTG

14941 ACACACACCCCAGCCTCTTCTCTACACCTCAGTGACTACCAACCACATCTAAATTATCAT
      TGTGTGTGGGGTCGGAGAAGAGATGTGGAGTCACTGATGGTTGGTGTAGATTTAATAGTA 14956 mbo11, 15001 CATTTCTCATCTGAATTATTGCAAGAAGCCATTGCAATAATTCAGATGAGAGTTGATACA
      GTAAAGAGTAGACTTAATAACGTTCTTCGGTAACGTTATTAAGTCTACTCTCAACTATGT 15061 AAGCCTTCCTGTTTCCAACCTTACCCTCATATAGTCTTTTCCCAACATTGCATCTAAAGT
      TTCGGAAGGACAAAGGTTGGAATGGGAGTATATCAGAAAAGGGTTGTAACGTAGATTTCA 15121 AATTTTTCAAATTGCAATTCTGATCCGGGGAATTC
      TTAAAAAGTTTAACGTTAAGACTAGGCCCCTTAAG 15150 ecor1,

```
              ValTyrGlyPheTrpGlyAlaThrThrGlnThrPheGlySerArgGlyMetThrAlaLeu
  1           GTCTATGGATTCTGGGGTGCCACAACTCAGACTTTCGGAAGCAGAGGCATGACCGCCTTA
              CAGATACCTAAGACCCCACGGTGTTGAGTCTGAAAGCCTTCGTCTCCGTACTGGCGGAAT

LeuLysValSerSerCysAspLysAsnThrGlyAspTyrTyrGluAspSerTyrGluAsp
 61           CTGAAGGTTTCTAGTTGTGACAAGAACACTGGTGATTATTACGAGGACAGTTATGAAGAT
              GACTTCCAAAGATCAACACTGTTCTTGTGACCACTAATAATGCTCCTGTCAATACTTCTA 115 mbo11, IleSerAlaTyrLeuLeuSerLysAsnAsnAlaIleGluProArgSerPheSerGlnAsn
121           ATTTCAGCATACTTGCTGAGTAAAAACAATGCCATTGAACCAAGAAGCTTCTCCCAGAAT
              TAAAGTCGTATGAACGACTCATTTTTGTTACGGTAACTTGGTTCTTCGAAGAGGGTCTTA 165 hind111, 177 ecor1, SerArgHisProSerThrArgGlnLysGlnPheAsnAlaThrThrIleProGluAsnAsp
181           TCAAGACACCCTAGCACTAGGCAAAAGCAATTTAATGCCACCACAATTCCAGAAAATGAC
              AGTTCTGTGGGATCGTGATCCGTTTTCGTTAAATTACGGTGGTGTTAAGGTCTTTTACTG IleGluLysThrAspProTrpPheAlaHisArgThrProMetProLysIleGlnAsnVal
241           ATAGAGAAGACTGACCCTTGGTTTGCACACAGAACACCTATGCCTAAAATACAAAATGTC
              TATCTCTTCTGACTGGGAACCAAACGTGTGTCTTGTGGATACGGATTTTATGTTTTACAG 246 mbo11, SerSerSerAspLeuLeuMetLeuLeuArgGlnSerProThrProHisGlyLeuSerLeu
301           TCCTCTAGTGATTTGTTGATGCTCTTGCGACAGAGTCCTACTCCACATGGGCTATCCTTA
              AGGAGATCACTAAACAACTACGAGAACGCTGTCTCAGGATGAGGTGTACCCGATAGGAAT 329 tthIII1, SerAspLeuGlnGluAlaLysTyrGluThrPheSerAspAspProSerProGlyAlaIle
361           TCTGATCTCCAAGAAGCCAAATATGAGACTTTTTCTGATGATCCATCACCTGGAGCAATA
              AGACTAGAGGTTCTTCGGTTTATACTCTGAAAAAGACTACTAGGTAGTGGACCTCGTTAT AspSerAsnAsnSerLeuSerGluMetThrHisPheArgProGlnLeuHisHisSerGly
421           GACAGTAATAACAGCCTGTCTGAAATGACACACTTCAGGCCACAGCTCCATCACAGTGGG
              CTGTCATTATTGTCGGACAGACTTTACTGTGTGAAGTCCGGTGTCGAGGTAGTGTCACCC 468 bstXI, AspMetValPheThrProGluSerGlyLeuGlnLeuArgLeuAsnGluLysLeuGlyThr
481           GACATGGTATTTACCCCTGAGTCAGGCCTCCAATTAAGATTAAATGAGAAACTGGGGACA
              CTGTACCATAAATGGGGACTCAGTCCGGAGGTTAATTCTAATTTACTCTTTGACCCCTGT 497 tthIII1, 504 stu1, ThrAlaAlaThrGluLeuLysLysLeuAspPheLysValSerSerThrSerAsnAsnLeu
541           ACTGCAGCAACAGAGTTGAAGAAACTTGATTTCAAAGTTTCTAGTACATCAAATAATCTG
              TGACGTCGTTGTCTCAACTTCTTTGAACTAAAGTTTCAAAGATCATGTAGTTTATTAGAC 542 pst1, 558 mbo11, IleSerThrIleProSerAspAsnLeuAlaAlaGlyThrAspAsnThrSerSerLeuGly
601           ATTTCAACAATTCCATCAGACAATTTGGCAGCAGGTACTGATAATACAAGTTCCTTAGGA
              TAAAGTTGTTAAGGTAGTCTGTTAAACCGTCGTCCATGACTATTATGTTCAAGGAATCCT 653 mstII, ProProSerMetProValHisTyrAspSerGlnLeuAspThrThrLeuPheGlyLysLys
661           CCCCCAAGTATGCCAGTTCATTATGATAGTCAATTAGATACCACTCTATTTGGCAAAAAG
              GGGGGTTCATACGGTCAAGTAATACTATCAGTTAATCTATGGTGAGATAAACCGTTTTTC SerSerProLeuThrGluSerGlyGlyProLeuSerLeuSerGluGluAsnAsnAspSer
721           TCATCTCCCCTTACTGAGTCTGGTGGACCTCTGAGCTTGAGTGAAGAAAATAATGATTCA
              AGTAGAGGGGAATGACTCAGACCACCTGGAGACTCGAACTCACTTCTTTTATTACTAAGT 763 mbo11, LysLeuLeuGluSerGlyLeuMetAsnSerGlnGluSerSerTrpGlyLysAsnValSer
781           AAGTTGTTAGAATCAGGTTTAATGAATAGCCAAGAAAGTTCATGGGGAAAAAATGTATCG
              TTCAACAATCTTAGTCCAAATTACTTATCGGTTCTTTCAAGTACCCCTTTTTTACATAGC
```

```
     SerThrGluSerGlyArgLeuPheLysGlyLysArgAlaHisGlyProAlaLeuLeuThr
841  TCAACAGAGAGTGGTAGGTTATTTAAAGGGAAAAGAGCTCATGGACCTGCTTTGTTGACT
     AGTTGTCTCTCACCATCCAATAAATTTCCCTTTTCTCGAGTACCTGGACGAAACAACTGA 862 aha111, 875 sac1, LysAspAsnAlaLeuPheLysValSerIleSerLeuLeuLysThrAsnLysThrSerAsn
901  AAAGATAATGCCTTATTCAAAGTTAGCATCTCTTTGTTAAAGACAAACAAAACTTCCAAT
     TTTCTATTACGGAATAAGTTTCAATCGTAGAGAAACAATTTCTGTTTGTTTTGAAGGTTA AsnSerAlaThrAsnArgLysThrHisIleAspGlyProSerLeuLeuIleGluAsnSer
961  AATTCAGCAACTAATAGAAAGACTCACATTGATGGCCCATCATTATTAATTGAGAATAGT
     TTAAGTCGTTGATTATCTTTCTGAGTGTAACTACCGGGTAGTAATAATTAACTCTTATCA ProSerValTrpGlnAsnIleLeuGluSerAspThrGluPheLysLysValThrProLeu
1021 CCATCAGTCTGGCAAAATATATTAGAAAGTGACACTGAGTTTAAAAAAGTGACACCTTTG
     GGTAGTCAGACCGTTTTATATAATCTTTCACTGTGACTCAAATTTTTTCACTGTGGAAAC 1021 bstXI, 1060 aha111, IleHisAspArgMetLeuMetAspLysAsnAlaThrAlaLeuArgLeuAsnHisMetSer
1081 ATTCATGACAGAATGCTTATGGACAAAAATGCTACAGCTTTGAGGCTAAATCATATGTCA
     TAAGTACTGTCTTACGAATACCTGTTTTTACGATGTCGAAACTCCGATTTAGTATACAGT 1132 nde1, AsnLysThrThrSerSerLysAsnMetGluMetValGlnGlnLysLysGluGlyProIle
1141 AATAAAACTACTTCATCAAAAAACATGGAAATGGTCCAACAGAAAAAGAGGGCCCCATT
     TTATTTTGATGAAGTAGTTTTTTGTACCTTTACCAGGTTGTCTTTTTTCTCCCGGGGTAA 1191 apa1, ProProAsp AlaGlnAsnProAspMetSerPhePheLysMetLeuPheLeuProGluSer
1201 CCACCAGA TGCACAAAATCCAGATATGTCGTTCTTTAAGATGCTATTCTTGCCAGAATCA
     GGTGGTCT ACGTGTTTTAGGTCTATACAGCAAGAAATTCTACGATAAGAACGGTCTTAGT AlaArgTrpIleGlnArgThrHisGlyLysAsnSerLeuAsnSerGlyGlnGlyProSer
1261 GCAAGGTGGATACAAAGGACTCATGGAAAGAACTCTCTGAACTCTGGGCAAGGCCCAGT
     CGTTCCACCTATGTTTCCTGAGTACCTTTCTTGAGAGACTTGAGACCCGTTCCGGGTCA ProLysGlnLeuValSerLeuGlyProGluLysSerValGluGlyGlnAsnPheLeuSer
1321 CCAAAGCAATTAGTATCCTTAGGACCAGAAAAATCTGTGGAAGGTCAGAATTTCTTGTCT    cDNA clone
     GGTTTCGTTAATCATAGGAATCCTGGTCTTTTTAGACACCTTCCAGTCTTAAAGAACAGA    C1

1337 mstII,

GluLysAsnLysValValValGlyLysGlyGluPheThrLysAspValGlyLeuLysGlu
1381 GAGAAAAACAAAGTGGTAGTAGGAAAGGGTGAATTTACAAAGGACGTAGGACTCAAAGAG
     CTCTTTTTGTTTCACCATCATCCTTTCCCACTTAAATGTTTCCTGCATCCTGAGTTTCTC

MetValPheProSerSerArgAsnLeuPheLeuThrAsnLeuAspAsnLeuHisGluAsn
1441 ATGGTTTTTCCAAGCAGCAGAAACCTATTTCTTACTAACTTGGATAATTTACATGAAAAT
     TACCAAAAAGGTTCGTCGTCTTTGGATAAAGAATGATTGAACCTATTAAATGTACTTTTA

AsnThrHisAsnGlnGluLysLysIleGlnGluGluIleGluLysLysGluThrLeuIle
1501 AATACACACAATCAAGAAAAAAAAATTCAGGAAGAATAGAAAAGAAGGAAACATTAATC
     TTATGTGTGTTAGTTCTTTTTTTTTAAGTCCTTCTTTATCTTTTCTTCCTTTGTAATTAG 1531 mbo11, GlnGluAsnValValLeuProGlnIleHisThrValThrGlyThrLysAsnPheMetLys
1561 CAAGAGAATGTAGTTTTGCCTCAGATACATACAGTGACTGGCACTAAGAATTTCATGAAG
     GTTCTCTTACATCAAAACGGAGTCTATGTATGTCACTGACCGTGATTCTTAAAGTACTTC 1617 mbo11, 1620 xmn1, AsnLeuPheLeuLeuSerThrArgGlnAsnValGluGlySerTyrAspGlyAlaTyrAla
1621 AACCTTTTCTTACTGAGCACTAGGCAAAATGTAGAAGGTTCATATGACGGGGCATATGCT
     TTGGAAAAGAATGACTCGTGATCCGTTTTACATCTTCCAAGTATACTGCCCCGTATACGA 1661 nde1, 1673 nde1, ProValLeuGlnAspPheArgSerLeuAsnAspSerThrAsnArgThrLysLysHisThr
1681 CCAGTACTTCAAGATTTTAGGTCATTAAATGATTCAACAAATAGAACAAAGAAACACACA
     GGTCATGAAGTTCTAAAATCCAGTAATTTACTAAGTTGTTTATCTTGTTTCTTTGTGTGT 1683 sca1, AlaHisPheSerLysLysGlyGluGluGluAsnLeuGluGlyLeuGlyAsnGlnThrLys
1741 GCTCATTTCTCAAAAAAAGGGGAGGAAGAAAACTTGGAAGGCTTGGGAAATCAAACCAAG
     CGAGTAAAGAGTTTTTTTCCCCTCCTTCTTTTGAACCTTCCGAACCCTTTAGTTTGGTTC 1765 mbo11, GlnIleValGluLysTyrAlaCysThrThrArgIleSerProAsnThrSerGlnGlnAsn
1801 CAAATTGTAGAGAAATATGCATGCACCACAAGGATATCTCCTAATACAAGCCAGCAGAAT
     GTTTAACATCTCTTTATACGTACGTGGTGTTCCTATAGAGGATTATGTTCGGTCGTCTTA 1817 ava3, 1819 sph1, 1833 ecor5, PheValThrGlnArgSerLysArgAlaLeuLysGlnPheArgLeuProLeuGluGluThr
1861 TTTGTCACGCAACGTAGTAAGAGAGCTTTGAAACAATTCAGACTCCCACTAGAAGAAACA
     AAACAGTGCGTTGCATCATTCTCTCGAAACTTTGTTAAGTCTGAGGGTGATCTTCTTTGT 1890 xmn1, 1912 mbo11,
```

```
     GluLeuGluLysArgIleIleValAspAspThrSerThrGlnTrpSerLysAsnMetLys
1921 GAACTTGAAAAAAGGATAATTGTGGATGACACCTCAACCCAGTGGTCCAAAAACATGAAA
     CTTGAACTTTTTTCCTATTAACACCTACTGTGGAGTTGGGTCACCAGGTTTTTGTACTTT

HisLeuThrProSerThrLeuThrGlnIleAspTyrAsnGluLysGluLysGlyAlaIle
1981 CATTTGACCCCGAGCACCCTCACACAGATAGACTACAATGAGAAGGAGAAAGGGGCCATT
     GTAAACTGGGGCTCGTGGGAGTGTGTCTATCTGATGTTACTCTTCCTCTTTCCCCGGTAA 1989 aval, ThrGlnSerProLeuSerAspCysLeuThrArgSerHisSerIleProGlnAlaAsnArg
2041 ACTCAGTCTCCCTTATCAGATTGCCTTACGAGGAGTCATAGCATCCCTCAAGCAAATAGA
     TGAGTCAGAGGGAATAGTCTAACGGAATGCTCCTCAGTATCGTAGGGAGTTCGTTTATCT 2098 bglII, SerProLeuProIleAlaLysValSerSerPheProSerIleArgProIleTyrLeuThr
2101 TCTCCATTACCCATTGCAAAGGTATCATCATTTCCATCTATAGACCTATATATCTGACC
     AGAGGTAATGGGTAACGTTTCCATAGTAGTAAAGGTAGATAATCTGGATATATAGACTGG ArgValLeuPheGlnAspAsnSerSerHisLeuProAlaAlaSerTyrArgLysLysAsp
2161 AGGGTCCTATTCCAAGACAACTCTTCTCATCTTCCAGCAGCATCTTATAGAAAGAAAGAT
     TCCCAGGATAAGGTTCTGTTGAGAAGAGTAGAAGGTCGTCGTAGAATATCTTTCTTTCTA 2182 mboII, 2190 mboII, SerGlyValGlnGluSerSerHisPheLeuGlnGlyAlaLysLysAsnAsnLeuSerLeu
2221 TCTGGGGTCCAAGAAAGCAGTCATTTCTTACAAGGAGCAAAGAAGAATAACCTTTCTTTA
     AGACCCCAGGTTCTTTCGTCAGTAAAGAATGTTCCTCGGTTTTTTTATTGGAAAGAAAT AlaIleLeuThrLeuGluMetThrGlyAspGlnArgGluValGlySerLeuGlyThrSer
2281 GCCATTCTAACCTTGGAGATGACTGGTGATCAAAGAGAGGTTGGCTCCCTGGGGACAAGT
     CGGTAAGATTGGAACCTCTACTGACCACTAGTTTCTCTCCAACCGAGGGACCCCTGTTCA 2307 boII, AlaThrAsnSerValThrTyrLysLysValGluAsnThrValLeuProLysProAspLeu
2341 GCCACAAATTCAGTCACATACAAGAAAGTTGAGAACACTGTTCTCCCGAAACCAGACTTG
     CGGTGTTTAAGTCAGTGTATGTTCTTTCAACTCTTGTGACAAGAGGGCTTTGGTCTGAAC ProLysThrSerGlyLysValGluLeuLeuProLysValHisIleTyrGlnLysAspLeu
2401 CCCAAAACATCTGGCAAAGTTGAATTGCTTCCAAAAGTTCACATTTATCAGAAGGACCTA
     GGGTTTTGTAGACCGTTTCAACTTAACGAAGGTTTTCAAGTGTAAATAGTCTTCCTGGAT 2422 xmnI, PheProThrGluThrSerAsnGlySerProGlyHisLeuAspLeuValGluGlySerLeu
2461 TTCCCTACGGAAACTAGCAATGGGTCTCCTGGCCATCTGGATCTCGTGGAAGGGAGCCTT
     AAGGGATGCCTTTGATCGTTACCCAGAGGACCGGTAGACCTAGAGCACCTTCCCTCGGAA 2490 balI, 2499 binI, 2520 mboII, LeuGlnGlyThrGluGlyAlaIleLysTrpAsnGluAlaAsnArgProGlyLysValPro
2521 CTTCAGGGAACAGAGGGAGCGATTAAGTGGAATGAAGCAAACAGACCTGGAAAAGTTCCC
     GAAGTCCCTTGTCTCCCTCGCTAATTCACCTTACTTCGTTTGTCTGGACCTTTTCAAGGG PheLeuArgValAlaThrGluSerSerAlaLysThrProSerLysLeuLeuAsp|ProLeu|
2581 TTTCTGAGAGTAGCAACAGAAAGCTCTGCAAAGACTCCCTCCAAGCTATTGGAT|CCTCTT|
     AAAGACTCTCATCGTTGTCTTTCGAGACGTTTCTGAGGGAGGTTCGATAACCTA|GGAGAA|

2621 bstXI, 2631 bamh1 binI,

|AlaTrpAspAsnHisTyrGlyThrGlnIleProLysGluGluTrpLysSerGlnGluLys|
2641 |GCTTGGGATAACCACTATGGTACTCAGATACCAAAAGAAGAGTGGAAATCCCAAGAGAAG|
     |CGAACCCTATTGGTGATACCATGAGTCTATGGTTTTCTTCTCACCTTTAGGGTTCTCTTC|                                                                 cDNA clone
                                                                                                                                  2-11
     |2677 mboII,

|SerProGluLysThrAlaPheLysLysLysAspThrIleLeuSerLeuAsnAlaCysGlu|
2701 |TCACCAGAAAAAACAGCTTTTAAGAAAAAGGATACCATTTTGTCCCTGAACGCTTGTGAA|
     |AGTGGTCTTTTTTGTCGAAAATTCTTTTTCCTATGGTAAAACAGGGACTTGCGAACACTT|

|SerAsnHisAlaIleAlaAlaIleAsnGluGlyGlnAsnLysProGluIleGluValThr|
2761 |AGCAATCATGCAATAGCAGCAATAAATGAGGGACAAAATAAGCCCGAAATAGAAGTCACC|
     |TCGTTAGTACGTTATCGTCGTTATTTACTCCCTGTTTTATTCGGGCTTTATCTTCAGTGG|

|TrpAlaLysGlnGlyArgThrGluArgLeuCysSerGlnAsnProProValLeuLysArg|
2821 |TGGGCAAAGCAAGGTAGGACTGAAAGGCTGTGCTCTCAAAACCCACCAGTCTTGAAACGC|
     |ACCCGTTTCGTTCCATCCTGACTTTCCGACACGAGAGTTTTGGGTGGTCAGAACTTTGCG|
          N-termini 80/77Kd

|HisGlnAsnGlyGluIleThrArgThrThrLeuGlnSerAspGlnGluGluIleAspTyrAsp|
2881 |CATCAACGGGAAATAACTCGTACTACTCTTCAGTCAGATCAAGAGGAAATTGACTATGAT|
     |GTAGTTGCCCTTTATTGAGCATGATGAGAAGTCAGTCTAGTTCCTTTAACTGATACTA|

|2907 mboII,

|AspThrIleSerValGluMetLysLysGluAsp|PheAspIleTyrAspGluAspGluAsn|
2941 |GATACCATATCAGTTGAAATGAAGAAGGAAGAT|TTTGACATTTATGATGAGGATGAAAAT|
     |CTATGGTATAGTCAACTTTACTTCTTCCTTCTA|AAACTGTAAATACTACTCCTACTTTTA|
```

```
       2961 mboII, 2968 mboII 70/67Kd
        |            N-termini
       ┌─────────────────────────────────────────────────────────────┐
       │GlnSerProArgSerPheGlnLysLysThrArgHisTyrPheIleAlaAlaValGluArg │
3001   │CAGAGCCCCCGCAGCTTTCAAAAGAAAACACGACACTATTTTATTGCTGCAGTGGAGAGG │
       │GTCTCGGGGGCGTCGAAAGTTTTCTTTTGTGCTGTGATAAAATAACGACGTCACCTCTCC │
       │                                                             │
       │ 3047 pst1,                                                  │
       │                                                             │
       │LeuTrpAspTyrGlyMetSerSerSerProHisValLeuArgAsnArgAlaGlnSerGly │
3061   │CTCTGGGATTATGGGATGAGTAGCTCCCCACATGTTCTAAGAAACAGGGCTCAGAGTGGC │
       │GAGACCCTAATACCCTACTCATCGAGGGGTGTACAAGATTCTTTGTCCCGAGTCTCACCG │
       │                                                             │
       │SerValProGlnPheLysLysValValPheGlnGluPheThrAspGlySerPheThrGln │
3121   │AGTGTCCCTCAGTTCAAGAAAGTTGTTTTCCAGGAATTTACTGATGGCTCCTTTACTCAG │
       │TCACAGGGAGTCAAGTTCTTTCAACAAAAGGTCCTTAAATGACTACCGAGGAAATGAGTC │
       │                                                             │
       │ProLeuTyrArgGlyGluLeuAsnGluHisLeuGlyLeuLeuGlyProTyrIleArgAla │
3181   │CCCTTATACCGTGGAGAACTAAATGAACATTTGGGACTCCTGGGGCCATATATAAGAGCA │
       │GGGAATATGGCACCTCTTGATTTACTTGTAAACCCTGAGGACCCCGGTATATATTCTCGT │
       └─────────────────────────────────────────────────────────────┘
        GluValGluAspAsnIleMetValThrPheArgAsnGlnAlaSerArgProTyrSerPhe
3241    GAAGTTGAAGATAATATCATGGTAACTTTCAGAAATCAGGCCTCTCGTCCCTATTCCTTC
        CTTCAACTTCTATTATAGTACCATTGAAAGTCTTTAGTCCGGAGAGCAGGGATAAGGAAG 3247 mboII, 3278 stu1, TyrSerSerLeuIleSerTyrGluGluAspGlnArgGlnGlyAlaGluProArgLysAsn
3301    TATTCTAGCCTTATTTCTTATGAGGAAGATCAGAGGCAAGGAGCAGAACCTAGAAAAAAC
        ATAAGATCGGAATAAAGAATACTCCTTCTAGTCTCCGTTCCTCGTCTTGGATCTTTTTTG 3325 mboII, PheValLysProAsnGluThrLysThrTyrPheTrpLysValGlnHisHisMetAlaPro
3361    TTTGTCAAGCCTAATGAAACCAAAACTTACTTTTGGAAAGTGCAACATCATATGGCACCC
        AAACAGTTCGGATTACTTTGGTTTTGAATGAAAACCTTTCACGTTGTAGTATACCGTGGG 3409 nde1, ThrLysAspGluPheAspCysLysAlaTrpAlaTyrPheSerAspValAspLeuGluLys
3421    ACTAAAGATGAGTTTGACTGCAAAGCCTGGGCTTATTTCTCTGATGTTGACCTGGAAAAA
        TGATTTCTACTCAAACTGACGTTTCGGACCCGAATAAAGAGACTACAACTGGACCTTTTT AspValHisSerGlyLeuIleGlyProLeuLeuValCysHisThrAsnThrLeuAsnPro
3481    GATGTGCACTCAGGCCTGATTGGACCCCTTCTGGTCTGCCACACTAACACACTGAACCCT
        CTACACGTGAGTCCGGACTAACCTGGGGAAGACCAGACGGTGTGATTGTGTGACTTGGGA 3492 stu1, AlaHisGlyArgGlnValThrValGlnGluPheAlaLeuPhePheThrIlePheAspGlu
3541    GCTCATGGGAGACAAGTGACAGTACAGGAATTTGCTCTGTTTTTTCACCATCTTTGATGAG
        CGAGTACCCTCTGTTCACTGTCATGTCCTTAAACGAGACAAAAAGTGGTAGAAACTACTC ThrLysSerTrpTyrPheThrGluAsnMetGluArgAsnCysArgAlaProCysAsnIle
3601    ACCAAAAGCTGGTACTTCACTGAAAATATGGAAAGAAACTGCAGGGCTCCCTGCAATATC
        TGGTTTTCGACCATGAAGTGACTTTTATACCTTTCTTTGACGTCCCGAGGGACGTTATAG 3639 pst1, GlnMetGluAspProThrPheLysGluAsnTyrArgPheHisAlaIleAsnGlyTyrIle
3661    CAGATGGAAGATCCCACTTTTAAAGAGAATTATCGCTTCCATGCAATCAATGGCTACATA
        GTCTACCTTCTAGGGTGAAAATTTCTCTTAATAGCGAAGGTACGTTAGTTACCGATGTAT 3667 mboII, 3679 aha111, MetAspThrLeuProGlyLeuValMetAlaGlnAspGlnArgIleArgTrpTyrLeuLeu
3721    ATGGATACACTACCTGGCTTAGTAATGGCTCAGGATCAAAGGATTCGATGGTATCTGCTC
        TACCTATGTGATGGACCGAATCATTACCGAGTCCTAGTTTCCTAAGCTACCATAGACGAG 3753 binI, SerMetGlySerAsnGluAsnIleHisSerIleHisPheSerGlyHisValPheThrVal
3781    AGCATGGGCAGCAATGAAAACATCCATTCTATTCATTTCAGTGGACATGTGTTCACTGTA
        TCGTACCCGTCGTTACTTTTGTAGGTAAGATAAGTAAAGTCACCTGTACACAAGTGACAT ArgLysLysGlu
3841    CGAAAAAAGAG
        GCTTTTTTCTC
``` cDNA clone C2

What is claimed is:

1. An introl-free DNA molecule comprising a coding sequence for the 92.5 kd peptide subunit of human Factor VIII:C wherein said peptide subunit is (i) cleavable by thromobin to yield the 52.5 kd and 40 kd peptide subunits of human Factor VIII:C, and (ii) capable of forming a $Ca^{++}$-bridged complex with the 77/80 kd peptide subunit of human Factor VIII:C, said complex having coagulation activity; and wherein said coding sequence is flanked by 5' and 3' sequences which are not derived from human Factor VIII:C.

2. A DNA molecule according to claim 1, wherein said DNA molecule is an extrachromosomal element.

3. A DNA molecule according to claim 1 wherein said extrachromosomal element is pSVF8-200.

4. A composition comprising host cells containing heterologous DNA substantially free of cells that do not comprise said heterologous DNA, wherein said heterologous DNA comprises an intron-free DNA molecule comprising a coding sequence for the 92.5 kd peptide subunit of human Factor VIII:C wherein said peptide subunit is (i) cleavable by thrombin to yield the 52.5 kd and 40 kd peptide subunits of human Factor VIII:C, and (ii) capable of forming a $Ca^{++}$-bridged complex with the 77/80 kd peptide subunit of human Factor VIII:C, said complex having coagulation activity; and wherein said coding sequence is flanked by 5' and 3' sequences which are not derived from human Factor VIII:C.

5. A composition according to claim 4 wherein said cells are mammalian cells.

6. A composition according to claim 5 wherein said mammalian cells are COS cells.

7. A process for preparing a recombinant human Factor VIII:C polypeptide, said process comprising:
    (a) providing a population of host cells produced by introducing into a host cell an exogenous DNA molecule comprising (1) an intron-free sequence coding for the 92.5 kd peptide subunit of human Factor VIII:C wherein said peptide subunit is (i) cleavable by thrombin to yield the 52.5 kd and 40 kd peptide subunits of human Factor VIII:C, and (ii) capable of forming a $Ca^{++}$-bridged complex with the 77/80 kd peptide subunit of human Factor VIII:C, said complex having coagulation activity; wherein said intron-free sequence is flanked by 5' and 3' sequences which are not derived from human Factor VIII:C; and (2) transcriptional and translational signals recognized by said host cell that will provide for expression of said intron-free sequence; and
    (b) growing said population of host cells under conditions whereby said intron-free sequence is expressed.

8. A process according to claim 7 wherein said host cell is a mammalian cell.

9. A process according to claim 7 wherein said polynucleotide is part of an extrachromosomal element having a plasmid or viral origin of replication and said host cell is a mammalian cell transformed or transfected by said extrachromosomal element.

10. A process according to claim 8 wherein said recombinant human Factor VIII:C polypeptide is glycosylated.

11. A process according to claim 8 wherein said transcriptional and translational signals comprise a mammalian viral promoter sequence.

12. A process according to claim 11 wherein said transcriptional and translational signals comprise an SV40 virus early region promoter and a SV40 virus late region polyadenylation sequence.

13. A process according to claim 7 wherein said polynucleotide sequence further encodes a leader sequence that will provide for secretion of said recombinant human Factor VIII:C polypeptide.

14. A DNA molecule according to claim 1 further comprising transcriptional and translational control signals that are compatible with a selected cellular host and that will provide for the expression of said coding sequence in said selected cellular host, said transcriptional and translational control sequences being heterologous to said coding sequence.

15. A DNA molecule according to claim 14 wherein said selected cellular host is a mammalian cell.

16. A microorganism or mammalian cell comprising the DNA molecule of claim 15.

* * * * *